(12) United States Patent
Kranias et al.

(10) Patent No.: US 8,524,683 B2
(45) Date of Patent: Sep. 3, 2013

(54) METHOD FOR DECREASING CARDIAC USING A NUCLEIC ACID MOLECULE ENCODING A VARIANT PHOSPHATASE INHIBITOR-1

(75) Inventors: Evangelia Kranias, Cincinnati, OH (US); Patricia Rodriguez, Madrid (ES); Bryan Mitton, Los Angeles, CA (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 13/196,450

(22) Filed: Aug. 2, 2011

(65) Prior Publication Data

US 2012/0053125 A1   Mar. 1, 2012

Related U.S. Application Data

(62) Division of application No. 12/162,499, filed as application No. PCT/US2007/003470 on Feb. 9, 2007, now Pat. No. 7,989,606.

(60) Provisional application No. 60/772,327, filed on Feb. 10, 2006.

(51) Int. Cl.
*C12N 15/15* (2006.01)

(52) U.S. Cl.
USPC .......................................................... 514/44

(58) Field of Classification Search
None
See application file for complete search history.

(56) References Cited

U.S. PATENT DOCUMENTS
2002/0159978 A1  10/2002  Allen
2004/0214760 A1  10/2004  Gupta et al.

OTHER PUBLICATIONS

Yue et al, Microdystrophin Gene Therapy of Cardiomyopathy Restores Dystrophin-Glycoprotein Complex and Improves Sarcolemma Integrity in the Mdx Mouse Heart. Circulation. Sep. 30, 2003; 108(13): 1626-1632.*
EP Form, EP, Apr. 6, 2009, European Search Report for 07750317.
PCT/ISA/210, WO, May 23, 2008, ISR for WO/07/100465.
PCT/ISA/237, WO, May 23, 2008, Written Opinion for WO/07/100465.
EP Forum, EP, Apr. 6, 2009, Supplemental European Search Report for 07750317.5.
Bibb, J.A. et al., "Phosphorylation of Protein Phosphatase Inhibitor-1 by Cdk5", The Journal of Biological Chemistry, 278(17): 14490-14497 (Apr. 27, 2001).
Braz, J.C., et al., "PKC-a Regulates Cardiac Contractility and Propensity Toward Heart Failure", Nature Medicine 10 (3): 248-254 (Mar. 2004)
Huang, K. "Ser 67—Phosphorylated Inhibitor 1 is a Potent Protein Phosphatase 1 Inhibitor", PNAS 97(11): 5824-5829 (May 23, 2000).
Rodriguez, P., et al., "Identification of a Novel Phosphorylation Site in Proein Phosphatase Inhibitor—1 as a Negatve Regulator of Cardiac Function", Journal of Biological Chemistry 281(50): 38599-38608 (Dec. 15, 2006).
Rodriquez, P., et al., "Phosphorylation of Human Inhibitor-1 at Ser 67 and/or Thr75 Attenuates Stimulaory Effects of Protein Kinase A Signaling in Cardiac Myocytes", Am. J. Physiol. Heart Circ. Physiol. 293: H762-H769 (2007).

* cited by examiner

*Primary Examiner* — Sheridan Swope
(74) *Attorney, Agent, or Firm* — Edwards Wildman Palmer LLP; Peter C. Lauro, Esq.; Melissa Hunter-Ensor, Esq.

(57) ABSTRACT

The present invention relates to novel nucleic acids which encode novel mutant forms of Inhibitor Protein-1 (I-1). In particular, the I-1 mutant forms comprise altered phosphorylation sites of PKC-α. In addition, the present invention relates to methods of regulating cardiac contractility and function, and for treatment of cardio myopathy and heart failure, which employ the novel nucleic acids and polypeptides. Vectors comprising the novel nucleic acids, Antibodies to the novel proteins, and diagnostic and screening methods associated therewith, are also provided.

1 Claim, 25 Drawing Sheets

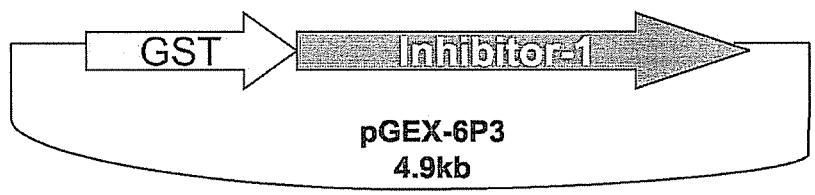

FIG. 1A

```
GCA ATG TCT CCA CGG CAA CGG AAG  AAG ATG ACA AGG ATC    I-1 WT
GCA ATG GCA CCA CGG CAA CGG AAG  AAG ATG ACA AGG ATC    I-1 (S67A)
GCA ATG TCT CCA CGG CAA CGG AAG  AAG ATG GCA AGG ATC    I-1 (T75A)
GCA ATG GCA CCA CGG CAA CGG AAG  AAG ATG GCA AGG ATC    I-1 (S67A/T75A)
GCA ATG TCT CCA CGG CAA CGG AAG  AAG ATG GAC AGG ATC    I-1 (T75D)
      Ser-67                              Thr-75
```

FIG. 1B

```
GCA ATG TCT CCA CGG CAA CGG AAG  AAG ATG ACA AGG ATC    I-1 WT
GCA ATG GAC CCA CGG CAA CGG AAG  AAG ATG ACA AGG ATC    I-1 (S67D)
GCA ATG TCT CCA CGG CAA CGG AAG  AAG ATG GAC AGG ATC    I-1 (T75D)
GCA ATG GAC CCA CGG CAA CGG AAG  AAG ATG GAC AGG ATC    I-1 (S67D/T75D)
      Ser-67                              Thr-75
```

METHOD FOR DECREASING CARDIAC USING A NUCLEIC ACID MOLECULE ENCODING A VARIANT PHOSPHATASE INHIBITOR-1

RELATED APPLICATIONS/PATENTS & INCORPORATION BY REFERENCE

This application is a divisional of U.S. Ser. No. 12/162,499, now U.S. Pat. No. 7,989,606, which is the U.S. national phase, pursuant to 35 U.S.C. §371, of PCT international application Ser. No. PCT/US2007/003470, filed Feb. 9, 2007, designating the United States and published in English on Sep. 7, 2007 as publication no. WO 2007/100465 A2, which claims priority to U.S. Provisional Application Ser. No. 60/772,327, filed Feb. 10, 2006. The entire contents of the aforementioned patent applications are incorporated herein by this reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF GOVERNMENT SUPPORT

The following invention was developed, in part, using funds from United States government agency grants. Therefore, the U.S. government has certain rights in the invention. The grants sponsoring entity is the National Institutes of Health, and the grants were awarded under contract numbers HL-64018, HL-26057, and HL-77101.

BACKGROUND OF THE INVENTION

It has been previously established (U.S. Patent App. Pub. No. 20050066381) that Protein Kinase C alpha ("PKC-α") activity is increased in the pathological state of heart failure. Phosphatase Inhibitor Protein-1 (I-1) is a key regulator of cardiac contractility. I-1 is known to regulate cardiac contractility by inhibiting the activity of Protein Phosphatase-1 ("PP-1"). I-1's ability to inhibit PP-1 is further known to be regulated by phosphorylation. When threonine 35 of I-1 is phosphorylated by Protein Kinase A (PKA), PP-1 activity is inhibited, cardiac contractility is enhanced (Pathak, A., et al. 2005 *Circ. Res* 15:756'-66). It was previously shown that serine 67 (S67) is a PKC alpha phosphorylation site, and that a S67 I-1 mutant (for example, S67A) that mimics a constitutively unphosphorylated state, shows reduced phosphorylation relative to the wild type I-1. However, in vitro testing conditions failed to reveal any inhibition of PP-1 activity.

Heart failure, also called congestive heart failure, is a disorder in which the contractility of the heart muscle decreases, and the heart loses its ability to pump blood efficiently. It is estimated to affect over 10 million Americans, alone. Heart failure is almost always a chronic, long-term condition, and consumes an inordinate amount of medical intervention and human resource dollars. In particular, the consequences of heart failure to the rest of the body organs can be devastating both in terms of the overall reduction in productive life of the patient, and the expense of treatment. The condition may affect the right side, the left side, or both sides of the heart. As the pumping action of the heart is compromised, blood begins backing up into other areas of the body. Many organs and organ systems begin to suffer cumulative damage from lack of oxygen and nutrients.

There may be many underlying causes, and heart failure becomes more common with advancing age. Problematically, some patients with heart failure have no obviously noticeable symptoms, permitting serious peripheral conditions to manifest without the benefit of early intervention to ward off or abate the rate of serious organ damage. Regular screening and early detection will enable a patient to elect life style and dietary changes that will slow progress of the disease. Methods for large-scale screening, and early and accurate detection, as well as capability to prognose the development of heart failure, before significant organ damage is incurred, are clearly needed. In addition, particularly with elderly patients, there is a need for additional long-lasting treatment options that do not depend entirely on compliance with drug product ingestion schedules.

SUMMARY OF THE INVENTION

Accordingly, the instant invention provides novel nucleotide sequences which encode polypeptides comprising novel forms of phophatase inhibitor protein-1, and functional fragments thereof, that may be employed in methods of modulating cardiac contractility in animals, including humans. The nucleotide sequences may be introduced into cardiac cells, and expression conditions may be triggered, using technology known in the art. The introduction of genetic material may be for purposes of incorporation into host genetic material for long-term expression capability, or for purposes of shorter, transient expression needs. In addition, the expression product itself, in the form of novel polypeptides comprising novel forms of I-1 may be administered, directly or indirectly, as the modulating agent, particularly in more acute onset instances.

In one aspect, the invention provides an isolated nucleic acid molecule that encodes a constitutively unphosphorylated phosphatase inhibitor-1 protein comprising the amino acid sequence of SEQ ID NO: 5, or a constitutively unphosphorylated fragment thereof. In one embodiment of the invention, the isolated nucleic acid molecule comprises SEQ ID NO: 3.

In yet another aspect, the invention provides an isolated nucleic acid molecule that encodes a constitutively unphosphorylated phosphatase inhibitor-1 protein, wherein the nucleic acid molecule encodes an amino acid sequence having at least 90% identity (e.g., 91%, 92%, 93%, 94%, 95%, 96%, 97%, 98%, 99% or 100% identity) to the amino acid sequence of SEQ ID NO: 5, or a constitutively unphosphorylated fragment thereof, and wherein the nucleic acid molecule encodes a constitutively unphosphorylated amino acid at position 75. In one embodiment of the invention, the isolated nucleic acid molecule comprises SEQ ID NO: 3 or a nucleotide molecule which is at least 90% identical to the nucleotide sequence of SEQ ID NO: 3.

In another aspect, the invention provides an isolated nucleic acid molecule that encodes a constitutively unphosphorylated phosphatase inhibitor-1 protein comprising the amino acid sequence of SEQ ID NO: 6, or a constitutively unphosphorylated fragment thereof. In one embodiment of the invention, the isolated nucleic acid molecule comprises SEQ ID NO: 4.

In another aspect, the invention provides an isolated nucleic acid molecule that encodes a constitutively unphosphorylated phosphatase inhibitor-1 protein, wherein the nucleic acid molecule encodes an amino acid sequence having at least 90% identity to the amino acid sequence of SEQ ID NO:6, (e.g., 91%, 92%, 93%, 94%, 95%, 96%, 97%, 98%, 99% or 100% identity) or a constitutively unphosphorylated fragment thereof, and wherein the nucleic acid molecule encodes a constitutively unphosphorylated amino acid at position 75. In one embodiment of the invention, the isolated nucleic acid molecule comprises SEQ ID NO: 4 or a nucleotide molecule which is at least 90% identical to the nucleotide sequence of SEQ ID NO: 4.

In yet another aspect, the invention provides an isolated polypeptide comprising the amino acid sequence of SEQ ID NO: 5, or a constitutively unphosphorylated fragment thereof.

In yet another aspect, the invention provides an isolated polypeptide comprising the amino acid sequence of SEQ ID NO: 6, or a constitutively unphosphorylated fragment thereof.

In another aspect, the invention provides an isolated nucleic acid molecule that encodes a constitutively unphosphorylated phosphatase inhibitor-1 protein comprising the amino acid sequence of SEQ ID NO: 12, or a constitutively unphosphorylated fragment thereof. In one embodiment of the invention, the isolated nucleic acid molecule comprises SEQ ID NO: 10.

In yet another aspect, the invention provides an isolated nucleic acid molecule that encodes a constitutively unphosphorylated phosphatase inhibitor-1 protein, wherein the nucleic acid molecule encodes an amino acid sequence having at least 90% identity (e.g., 91%, 92%, 93%, 94%, 95%, 96%, 97%, 98%, 99% or 100% identity) to the amino acid sequence of SEQ ID NO: 12, or a constitutively unphosphorylated fragment thereof, and wherein the nucleic acid molecule encodes a constitutively unphosphorylated amino acid at position 75. In one embodiment of the invention, the isolated nucleic acid molecule comprises SEQ ID NO: 10 or a nucleotide molecule which is at least 90% identical to the nucleotide sequence of SEQ ID NO: 10.

In another aspect, the invention provides an isolated nucleic acid molecule that encodes a constitutively unphosphorylated phosphatase inhibitor-1 protein comprising the amino acid sequence of SEQ ID NO: 16, or a constitutively unphosphorylated fragment thereof. In one embodiment of the invention, the isolated nucleic acid molecule comprises SEQ ID NO: 15.

In yet another aspect, the invention provides an isolated nucleic acid molecule that encodes a constitutively unphosphorylated phosphatase inhibitor-1 protein, wherein the nucleic acid molecule encodes an amino acid sequence having at least 90% identity (e.g., 91%, 92%, 93%, 94%, 95%, 96%, 97%, 98%, 99% or 100% identity) to the amino acid sequence of SEQ ID NO: 16, or a constitutively unphosphorylated fragment thereof, and wherein the nucleic acid molecule encodes a constitutively unphosphorylated amino acid at position 67 and 75. In one embodiment of the invention, the isolated nucleic acid molecule comprises SEQ ID NO: 15 or a nucleotide molecule which is at least 90% identical to the nucleotide sequence of SEQ ID NO: 15.

In another aspect, the invention provides an isolated nucleic acid molecule that encodes a constitutively unphosphorylated phosphatase inhibitor-1 protein comprising the amino acid sequence of SEQ ID NO: 18, or a constitutively unphosphorylated fragment thereof. In one embodiment of the invention, the isolated nucleic acid molecule comprises SEQ ID NO: 17.

In yet another aspect, the invention provides an isolated nucleic acid molecule that encodes a constitutively unphosphorylated phosphatase inhibitor-1 protein, wherein the nucleic acid molecule encodes an amino acid sequence having at least 90% identity (e.g., 91%, 92%, 93%, 94%, 95%, 96%, 97%, 98%, 99% or 100% identity) to the amino acid sequence of SEQ ID NO:18, or a constitutively unphosphorylated fragment thereof, and wherein the nucleic acid molecule encodes a constitutively unphosphorylated amino acid at position 67 and 75. In one embodiment of the invention, the isolated nucleic acid molecule comprises SEQ ID NO: 17 or a nucleotide molecule which is at least 90% identical to the nucleotide sequence of SEQ ID NO: 17.

In another aspect, the invention provides a method of decreasing cardiac contractility in a subject, the method comprising introducing, into heart cells of the subject, an effective amount of an isolated nucleic acid molecule that encodes a constitutively unphosphorylated phosphatase inhibitor-1 protein comprising the amino acid sequence of SEQ ID NO: 5 or SEQ ID NO: 6, or a constitutively unphosphorylated fragment thereof, thereby decreasing cardiac contractility in the subject.

In another aspect, the invention provides a method of decreasing cardiac contractility in a subject, the method comprising administering an effective amount of an isolated polypeptide comprising the amino acid sequence of SEQ ID NO: 5 or SEQ ID NO: 6, or a constitutively unphosphorylated fragment thereof, thereby decreasing cardiac contractility in the subject.

In another aspect, the invention provides a method of treating a subject having heart failure, the method comprising: introducing into heart cells of the subject, a nucleic acid molecule that comprises a sequence encoding a mutant form of phosphatase inhibitor-1 protein in an amount effective to decrease phosphatase activity, wherein the mutant form comprises at least one constitutively unphosphorylated amino acid at a position that is a PKC-α phosphorylation site in the wild type phosphatase inhibitor-1 protein, thereby treating the subject having heart failure. In another embodiment, the at least one constitutively unphosphorylated amino acid is A (alanine), D (aspartic acid), or C (cysteine) at position 67 or A, D, or C at position 75 in said mutant form of phosphatase inhibitor-1 protein. In yet another embodiment, the nucleic acid molecule has at least 90% identity to a nucleic acid molecule comprising the sequence selected from the group consisting of SEQ ID NO: 3, 4, 9, 10, 15, and 17, and wherein the nucleic acid molecule encodes a constitutively unphosphorylated amino acid at position 67 or 75. In yet another embodiment, the mutant form of phosphatase inhibitor-1 protein comprises an amino acid sequence selected from the group consisting of SEQ ID NO: 5. 6, 11, 12, 16, and 18. The nucleic acid molecule encoding the mutant form of the protein may be selected from the group consisting of SEQ ID NO: 3, 4, 9, 10, 15, and 17. The mutant form of phosphatase inhibitor-1 protein may be a full length protein or a constitutively unphosphorylated fragment thereof. In another embodiment, the method further comprises obtaining the nucleic acid.

In another embodiment, the method according to the invention further comprises introducing a nucleic acid molecule that comprises a sequence encoding a mutant form of phosphatase inhibitor-1 protein in an amount effective to decrease phosphatase activity, wherein the mutant form comprises at least one constitutively phosphorylated amino acid at a position that is a PKA phosphorylation site in the wild type phosphatase inhibitor-1 protein, thereby treating the subject having heart failure. In yet another aspect, the at least one constitutively phosphorylated amino acid is D (aspartic acid, GAC, although GAT is likewise contemplated) or E (glutamic acid, GAG, although GAA is likewise contemplated) at position 35 in said mutant form of phosphatase inhibitor-1 protein. In yet another embodiment, the nucleic acid molecule has at least 90% identity to a nucleic acid molecule comprising SEQ ID NO: 19, and the nucleic acid molecule encodes a constitutively phosphorylated amino acid at position 35. In yet another embodiment, the mutant form of phosphatase inhibitor-1 protein comprises the amino acid sequence of SEQ ID NO: 20. The nucleic acid molecule encoding the mutant form of the protein may comprise SEQ ID NO: 19. The mutant form of phosphatase inhibitor protein may be a full length protein or a constitutively phosphorylated fragment thereof.

In another aspect, the invention provides a method of treating a subject having heart failure, the method comprising: introducing into heart cells of the subject, a nucleic acid molecule encoding a polypeptide comprising the amino acid sequence of SEQ ID NO: 21 or a fragment thereof, in an amount effective to decrease phosphatase activity, thereby treating the subject having heart failure. In another embodiment, the nucleic acid molecule comprises a sequence encoding a polypeptide comprising at least amino acid positions 1-65 of SEQ ID NO: 21, wherein said polypeptide is truncated at a position that is a PKC-α phosphorylation site in SEQ ID NO: 21. The polypeptide may, in yet another embodiment, be truncated at position 67 or 75 of SEQ ID NO: 21. These truncated forms of I-1 retain their functionality with respect to inhibiting PP-1.

In another embodiment of the invention, the nucleic acid molecule further comprises a promoter operably linked to the coding sequence. In yet another embodiment, the promoter is a constitutive promoter. In still another embodiment, the promoter is expressed in multiple tissues, wherein one of said tissues is a cardiac muscle tissue. The promoter may comprise regulatory sequences from any member of the group consisting of: Cytomegalovirus (CMV), cardiac specific troponin T, myosin heavy chain, and myosin light chain.

In another embodiment of a method according to the invention, the nucleic acid molecule is introduced by administering a viral delivery system comprising a viral particle. In yet another embodiment, the viral particle comprises a lentiviral particle or an adeno-associated viral (AAV) particle.

In another embodiment of a method according to the invention, the nucleic acid molecule is introduced in an amount effective to result in a condition selected from the group consisting of myocyte shortening, lowering of the time constant for relaxation, and accelerating calcium signal decay, and combinations thereof. In yet another embodiment, the nucleic acid molecule is introduced in an amount effective to improve the end-systolic pressure dimension relationship.

In another embodiment of a method according to the invention, the subject having heart failure has a condition selected from the group consisting of ischemia, arrhythmia, myocardial infarction, abnormal heart contractility, and abnormal Ca2+ metabolism, and combinations thereof, in addition to heart failure. In yet another embodiment, the subject is human.

In another embodiment of a method according to the invention, flow of blood through coronary vessels of the heart of the subject is restricted, and the nucleic acid molecule is introduced into the lumen of a coronary artery in the subject. In yet another embodiment, the heart is pumping while coronary vein outflow is restricted. In yet another embodiment, flow of blood through the coronary vessels is completely restricted. The restricted coronary vessels may comprise, without limitation: the left anterior descending artery (LAD), the distal circumflex artery (LCX), the great coronary vein (GCV), the middle cardiac vein (MCV), or the anterior interventricular vein (AIV). In yet another embodiment, the introduction of the nucleic acid molecule occurs after ischemic preconditioning of the coronary vessels. In still another embodiment, the nucleic acid molecule is injected into the heart of the subject while aortic flow of blood out of the heart is restricted, thereby allowing the nucleic acid molecule to flow into the heart.

In another embodiment of a method according to the invention, the administering comprises the steps of: restricting aortic flow of blood out of the heart, such that blood flow is re-directed to coronary arteries; injecting the nucleic acid molecule into the lumen of the heart, aorta, or coronary ostia to provide the nucleic acid molecule to a coronary artery; pumping the heart while the aortic flow of blood out of the heart is restricted; and reestablishing the aortic flow of blood. In yet another embodiment, the nucleic acid molecule is injected into the heart with a catheter. In still another embodiment, the nucleic acid molecule is directly injected into a muscle of the heart. In still another embodiment, the method further comprises evaluating a parameter of heart function in the subject. The parameter of heart function may, without limitation, be one or more of: heart rate, cardiac metabolism, heart contractility, ventricular function, Ca2+ metabolism, and sarcoplasmic reticulum Ca2+ ATPase activity.

In another aspect, the invention provides a method of diagnosing or prognosing heart failure in a subject comprising: obtaining a sample of cardiac phosphatase inhibitor-1 protein from the subject; and detecting the presence of at least one phosphorylated PKC-α phosphorylation site, thereby diagnosing or prognosing heart failure in the subject. In another embodiment, the at least one phosphorylated PKC-α phosphorylation site is a T residue at position 75 or a S residue at position 67 of the cardiac phosphatase inhibitor-1 protein.

In another aspect, the invention provides a recombinant vector comprising an isolated nucleic acid molecule that encodes a constitutively unphosphorylated phosphatase inhibitor-1 protein comprising the amino acid sequence of SEQ ID NO: 5, or a constitutively unphosphorylated fragment thereof. In yet another aspect, the invention provides a recombinant vector comprising an isolated nucleic acid molecule that encodes a constitutively unphosphorylated phosphatase inhibitor-1 protein comprising the amino acid sequence of SEQ ID NO: 6, or a constitutively unphosphorylated fragment thereof.

In another aspect, the invention provides a pharmaceutical composition comprising an isolated polypeptide comprising the amino acid sequence of SEQ ID NO: 5, or a constitutively unphosphorylated fragment thereof and a pharmaceutically acceptable carrier, excipient, or diluent. In yet another aspect, the invention provides a pharmaceutical composition comprising an isolated polypeptide comprising the amino acid sequence of SEQ ID NO: 6, or a constitutively unphosphorylated fragment thereof and a pharmaceutically acceptable carrier, excipient, or diluent.

In another aspect, the invention provides a pharmaceutical composition comprising an isolated nucleic acid molecule that encodes a constitutively unphosphorylated phosphatase inhibitor-1 protein comprising the amino acid sequence of SEQ ID NO: 5, or a constitutively unphosphorylated fragment thereof, and a pharmaceutically acceptable carrier, excipient, or diluent. In yet another aspect, the invention provides a pharmaceutical composition comprising an isolated nucleic acid molecule that encodes a constitutively unphosphorylated phosphatase inhibitor-1 protein comprising the amino acid sequence of SEQ ID NO: 6 or a constitutively unphosphorylated fragment thereof, and a pharmaceutically acceptable carrier, excipient, or diluent. In a further embodiment, the nucleic acid molecule is present in a viral vector selected from the group consisting of: recombinant retrovirus, adenovirus, adeno-associated virus, lentivirus, and herpes simplex virus-1.

In another aspect, the invention provides an antibody raised against an isolated polypeptide comprising the amino acid sequence of SEQ ID NO: 5, or a constitutively unphosphorylated fragment thereof. In another aspect, the invention provides an antibody raised against an isolated polypeptide comprising the amino acid sequence of SEQ ID NO: 6, or a constitutively unphosphorylated fragment thereof. In still another aspect, the invention provides a diagnostic reagent comprising such an antibody.

In another aspect, the invention provides a kit for treating a subject having heart failure comprising an isolated nucleic acid molecule that encodes a constitutively unphosphorylated phosphatase inhibitor-1 protein comprising the amino acid sequence of SEQ ID NO: 5 or SEQ ID NO: 6, or a constitutively unphosphorylated fragment thereof, and instructions for use in accordance with the methods of the invention. The kit can further comprise an isolated nucleic acid molecule that encodes a mutant form of phosphatase inhibitor-1 protein comprising the amino acid sequence of SEQ ID NO: 20.

In another aspect, the invention provides a kit for treating a subject having heart failure comprising an isolated nucleic acid molecule that comprises a sequence encoding a polypeptide comprising the amino acid sequence of SEQ ID NO: 21 or a fragment thereof, and instructions for treating the subject having heart failure in accordance with the methods of the invention.

Other aspects of the invention are described in the following disclosure, and are within the ambit of the invention.

BRIEF DESCRIPTION OF THE FIGURES

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 1. Recombinant I-1 Proteins—(A) Schematic diagram of I-1 recombinant proteins. The human I-1 cDNA was cloned into the pGEX-6P3 vector for expression as a GST-fusion protein. (B) SEQ ID Nos: 34-38, respectively, in order of appearance, and (C) SEQ ID Nos: 34, 39, 38, and 40, respectively, in order of appearance. (B) and (C) show sequence alignments showing I-1 wild-type in alignment with the recombinant mutants (S67A, T75A, S67A/T75A, S67D, T75D, and S67D/T75D).

DETAILED DESCRIPTION OF THE INVENTION

Definitions

Figure 2:
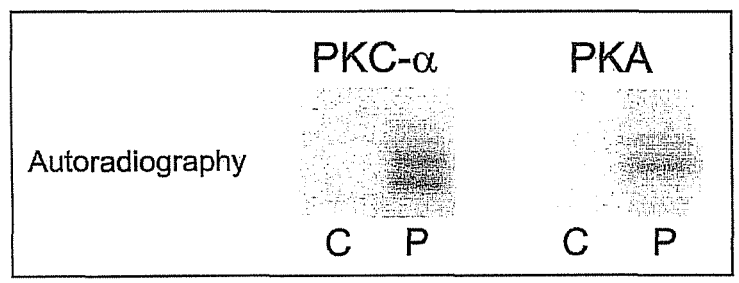
FIG. 2. Phosphorylation of Recombinant Human Inhibitor-1 by PKC-α and PKA—Autoradiographs depicting phosphorylation of I-1 by PKC-α or by PKA (i.e., radiolabeled phosphoproteins). For the PKC-α assay, the control sample (C) lacks PKC-α, $Ca^{2+}$ (EGTA present), 1,2-diacyl-sn-glycero-3-phospho-L-serine, and phosphatidylserine, but contains all other components of the assay. For the PKA assay, the control sample (C) lacks PKA and cAMP, but contains all other components of the assay. The reactions were initiated by the addition of 0.25 mM [$\gamma^{32}$P] ATP (0.4 mCi/nmol).

As used herein, the term "nucleic acid molecule" or "nucleic acid sequence" is intended to refer to polynucleotides that include an open reading frame encoding a polypeptide, and can further include non-coding sequences, such as introns and desirable regulatory sequences (e.g., promoters, enhancers, transcriptional terminators and the like).

Nucleic acid sequences of the invention can encode a specific gene for a selected purpose. The gene can be endogenous to the host cell or can be recombinantly introduced into the host cell, e.g., as a plasmid maintained episomally or a plasmid (or fragment thereof) that is stably integrated into the genome.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. Isolated nucleic acids include sequences inserted into plasmids, cosmids, artificial chromosomes, and the like. Thus, a recombinant nucleic acid may constitute an isolated nucleic acid. An isolated protein may be associated with other proteins or nucleic acids, or both, with which it associates in the cell, or with cellular membranes if it is a membrane-associated protein. An isolated material may be, but need not be, purified.

As used herein, the term "complement" of a nucleic acid (nucleotide) sequence refers to a sequence of bases that can form a double-stranded structure by matching base pairs. The complementary sequence to G-T-A-C, for instance, is C-A-T-G.

As used herein, a "phosphatase inhibitor-1 protein" or "I-1 protein" is a protein, described, for example, by GenBank Accession No. NM_006741, that regulates cardiac contractility by inhibiting the activity of Protein Phosphatase-1.

In the context of the phosphatase inhibitor-1 protein or I-1 protein, the term "wild-type" refers to the nucleotide sequence of SEQ ID NO: 7 encoding Phosphotase Inhibitor Protein-1 (I-1), subunit 1A, and the polypeptide sequence of SEQ ID NO: 8, and any other nucleotide sequence that encodes an I-1 protein (having the same functional properties and binding affinities as the aforementioned polypeptide sequences), such as allelic variants.

Wild-type I-1 includes so-called "functional derivatives" of the protein. By "functional derivative" is meant a "chemical derivative," "fragment," "polymorph" or "variant" of the polypeptide or nucleic acid of the invention. A functional derivative retains at least a portion of the function of the protein, which permits its utility in accordance with the invention. It is well known in the art that, due to the degeneracy of the genetic code, numerous different nucleic acid sequence can code for the same amino acid sequence. It is also well known in the art that conservative changes in amino acid can be made to arrive at a protein or polypeptide that retains the functionality of the original. In both cases, all permutations are intended to be covered by this disclosure.

Included within the scope of this invention are the functional equivalents of the herein-described isolated nucleic acid molecules. The degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end, provided that its addition, deletion or substitution does not alter the amino acid sequence described herein, which is encoded by the nucleotide sequence. For example, the nucleic acid molecule of the present invention may have restriction endonuclease recognition sites added to its 5'-end and/or 3'-end.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules that give rise to their production, even though the differences between the nucleic acid molecules are not related to the degeneracy of the genetic code.

A "chemical derivative" of I-1 contains additional chemical moieties not normally a part of the protein. Covalent modifications of the protein or peptides may be introduced into the molecule by reacting targeted amino acid residues of the peptide with an organic derivatizing agent that is capable of reacting with selected side chains or terminal residues.

The term "fragment" is used to indicate a polypeptide derived from the amino acid sequence of I-1 having a length less than the full-length polypeptide from which it has been derived. Such a fragment may, for example, be produced by proteolytic cleavage of the full-length protein. Such a fragment may also be obtained recombinantly by appropriately modifying the DNA sequence encoding the proteins to delete one or more amino acids at one or more sites of the C-terminus, N-terminus, and/or within the native sequence. Such fragments retain the functional portion of the native I-1.

Another functional derivative intended to be within the scope of the present invention is a "variant" polypeptide, which either lacks one or more amino acids or contains additional or substituted amino acids relative to the native polypeptide. Such variants having added, substituted and/or additional amino acids retain the functional portion of the native I-1. A functional derivative of a protein with deleted, inserted and/or substituted amino acid residues may be prepared using standard techniques well-known to those of ordinary skill in the art (for example, using site-directed mutagenesis (Adelman et al., 1983, DNA 2:183). Alternatively, proteins with amino acid deletions, insertions and/or substitutions may be conveniently prepared by direct chemical synthesis, using methods well-known in the art.

As used herein, the term "mutant" refers to an I-1 polypeptide translated from a gene containing a genetic mutation that results in an amino acid sequence that is altered in comparison to the wild-type sequence and results in an altered function of the I-1 polypeptide.

As used herein, the term "phosphatase activity" refers to the activity of phosphatase on the commonly used model protein substrate, MyBP. Herein, Myelin Basic Protein (MyBP) is employed (labeled with $^{32}$P) as a substrate (binding partner) in measuring change in protein phosphatase activity.

As used herein, the phrase "constitutively unphosphorylated", as in a "constitutively unphosphorylated phosphatase inhibitor I-1 protein" or a "constitutively unphosphorylated fragment of phosphatase inhibitor I-1 protein" refers to the phosphatase inhibitor-1 protein, or a fragment thereof, as continuously unphosphorylated in at least one specific amino acid position under all physiological conditions. In a specific embodiment, the fragment retains at least one of the amino acid positions 67 or 75 or both, and contains a mutation that removes or replaces the phosphorylatable hydroxyl groups at that particular residue. A "constitutively unphosphorylated amino acid of phosphatase inhibitor-1 protein" refers to an amino acid within the polypeptide chain of I-1 protein, or a fragment thereof, that is unphosphorylated under all physiological conditions, i.e., through a mutation of the amino acid residue that removes or replaces the phosphorylatable hydroxyl groups at that particular residue.

As used herein, the term "PKC-α phosphorylation site" refers to a specific amino acid that is phosphorylated by Protein Kinase C, isoform alpha (PKC-α). Like PKA, PKC is a serine/threonine-specific protein kinase. It phosphorylates serine or threonine residues in its substrate (specifically, it phosphorylates the OH group in the residue).

As used herein, the term "PKA phosphorylation site" refers to a specific amino acid that is phosphorylated by Protein Kinase A (PKA, also known as cAMP-dependent protein kinase). Each PKA is a holoenzyme that consists of two regulatory and two catalytic subunits. Under low levels of cAMP, the holoenzyme remains intact and is catalytically inactive. When the concentration of cAMP rises (e.g. activation of adenylate cyclases by certain G protein-coupled receptors, inhibition of phosphodiesterases which degrade cAMP), cAMP binds to the two binding sites on the regulatory subunits, which then undergo a conformational change that releases the catalytic subunits. The free catalytic subunits can then catalyze the transfer of ATP terminal phosphates to protein substrates at serine or threonine residues.

As used herein, the term "treating" refers to administering an agent in amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject. For example, the mode of administration can include delivery by a virus or virus-like particle. By preventing progression of a disorder, a treatment can prevent deterioration of a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "heart failure" refers to any disorder in which the heart has a defect in its ability to pump adequately to meet the body's needs. In many cases, heart failure is the result of one or more abnormalities at the cellular level in the various steps of excitation-contraction coupling of the cardiac cells. It is most frequently due to a defect in myocardial contraction, which can occur for many reasons, the most common of which include: ischemic damage to the myocardium, excessive mechanical resistance to the outflow of blood from the heart, overloading of the cardiac chambers due to defective valve function, infection or inflammation of the myocardium, or congenitally poor myocardial contractile function. (Braunwald, E. 2001 *Harrison's Principles of Internal Medicine*, 15th ed., pp 1318-29).

As used herein, the term "cardiomyopathy" refers to a deterioration of function of the myocardium (i.e., heart muscle). Cardiomyopathy can be extrinsic (e.g., wherein the primary pathology resides outside of the myocardium itself, for example, caused by ischemia) or intrinsic (e.g., wherein the weakness in the heart muscle is not due to an identifiable external cause).

As used herein, the term "contractility" (as in myocardial contractility) refers to the performance of cardiac muscle. It is often defined as: the intrinsic ability of a cardiac muscle fibre to contract at a given fibre length.

As used herein, the term "end-systolic pressure dimension relationship" (also known as end-systolic pressure-volume relationship) refers to the following linear relationship (Grossman, W., et al. 1977 *Circulation* 56:845-52):

$$P_{ES}=mV_{ES}+b,$$

wherein $P_{ES}$ and $V_{ES}$ are the end-systolic pressure and volume, respectively, m is the slope of the line describing their relations, and b is the pressure at $V_{ES}=0$. The equation can also be expressed as:

$$P_{ES}=m(V_{ES}-V_0),$$

wherein $V_0=-b/m$, the volume at $P_{ES}=0$. End-systolic pressure-dimension relationship is generally considered a powerful index of ventricular contractility in humans.

As used herein, the term "heart cell" refers to a cell which can be: (a) part of a heart present in a subject, (b) part of a heart which is maintained ex vivo, (c) part of a heart tissue, or (d) a cell which is isolated from the heart of a subject. For example, the cell can be a muscle cell, such as a cardiac myocyte (cardiomyocyte) or smooth muscle cell. Heart cells of the invention can also include endothelial cells within the heart, for example, cells of a capillary, artery, or other vessel.

As used herein, the term "heart" refers to the heart organ present in a subject or to a heart organ that is maintained ex vivo, outside a subject.

As used herein, the term "heart tissue" refers to tissue that is derived from the heart of a subject.

As used herein, the term "restricting blood flow" refers to substantially blocking the flow of blood through a vessel, e.g., flow of blood into the distal aorta and its branches. For example, at least about 50% of the blood flowing out of the heart is restricted, preferably about 75% and more preferably about 80, 90, or 100% of the blood is restricted from flowing out of the heart. The blood flow can be restricted by obstructing the aorta and the pulmonary artery, e.g., with clamps.

As used herein, the term "obtaining" refers to synthesizing, purchasing, or otherwise acquiring (the nucleic acid or protein).

As used herein, the term "viral delivery system" refers to a viral particle, e.g., virus or virus like particle that can introduce a nucleic acid that includes a non-viral sequence into a mammalian cell. The viral delivery system itself may or may not be competent for viral replication.

Other definitions appear in context throughout this disclosure.

Additional Embodiments of the Invention

Phosphatase Inhibitor-1 and Mutants Thereof

A fine-tuned regulation of protein kinase and protein phosphatase activities is essential in the control of the phosphorylation state of various key phosphoprotein substrates, which modulate glycogen metabolism, protein synthesis, cell division, neuronal signaling and muscle contraction. A cross-talk between the second messenger cAMP-dependent protein kinase (PKA) and the type-1 phosphatase (PP1) occurs at the level of an endogenous phosphoprotein, inhibitor-1 (I-1), allowing amplification of the cAMP-signaling cascade.

I-1 was first identified in rabbit skeletal muscle, but is widely expressed in mammalian tissues and highly conserved across species. This thermostable protein (Mr 18,700), upon phosphorylation by PKA at Thr-35, becomes active and potently inhibits PP1, enhancing PKA-mediated protein phosphorylation. Thr-35 on inhibitor-1 is dephosphorylated by $Ca^{2+}$/calmodulin-dependent protein 2B (PP-2B, calcineurin) and protein phosphatase 2A (PP-2A), but PP-2B plays a predominant role in the presence of $Ca^{2+}$. This reversible phosphorylation of inhibitor-1, which is reciprocally regulated by cAMP and calcium, connects the actions of the two major second messengers, resulting in modulation of a large number of intracellular processes.

In cardiac muscle, the regulation of PP1 by I-1 has been shown to play a role in both basal contractility as well as in the heart's responses to β-adrenergic stimulation. The positive inotropic effect of the β-adrenergic agonist, isoproterenol, is accompanied by I-1 phosphorylation resulting in inhibition of PP1 activity enhances cardiac contractility by preventing the dephosphorylation of important proteins involved in the contractile state of the heart. Intriguingly, a constitutively activated form of I-1 (T35D; AA1-65) not only protected the heart from developing hypertrophy induced by pressure-overload, but also rescued cardiac function in the setting of pre-existing heart failure, suggesting that I-1 may be a promising candidate in the treatment of heart failure.

In addition to Thr-35 phosphorylation on I-1, Ser-67 was also found to be substantially phosphorylated in vitro. It was discovered that the proline-directed kinase, Cdk5, in striatal brain tissue and the neuronal cdc2-like protein kinase, NCLK were both capable of phosphorylating Ser-67 on I-1. Cdk5-mediated phosphorylation had no effect on I-1 activity, while NCLK enhanced inhibitory activity. More recently it was found that PKC-α, the major isozyme expressed in the mouse and rabbit heart, also phosphorylates Ser-67, and this may reduce the ability of I-1 to interact with PP1 by 50%, increasing PP1 activity.

Given that both PKC-α and PP1 activities are significantly increased in human and experimental heart failure, the present invention is based, in part, on the discovery that human I-1 is phosphorylated at an additional site (Thr-75) by PKC-α. Data presented herein demonstrates that this kinase phosphorylates Thr-75 to the same extent that it phosphorylates Ser-67; moreover, both residues are phosphorylated independently of each other. Extensive kinetic analyses indicate that neither of these PKC-α sites inhibits the activity of the catalytic subunit of PP1. Furthermore, neither of these phosphorylated sites interferes with the PKA-mediated inhibitory function of I-1. The discovery of this novel phosphorylation site provides new agents and therapies to treat heart failure, and, in particular, new approaches to therapy based on the interplay between increased PP1, PKA, and PKC-α activity under pathophysiological conditions.

Thus, a method of treating a subject having heart failure is contemplated comprising inhibiting the phosphorylation activity of PKC-α. Further contemplated is enhancing the phosphorylation activity of PKA in addition to inhibiting phosphorylation activity of PKC alpha.

A method of treatment according to an embodiment of the present invention comprises introduction into the heart cells of the subject, a nucleic acid that comprises a sequence encoding a mutant form of phosphatase inhibitor-1 protein, wherein the mutant form comprises at least one amino acid at a position that is a PKC-α phosphorylation site in the wild type, wherein the at least one amino acid is constitutively unphosphorylated or mimics an unphosphorylated state in the mutant form.

In a more specific embodiment, the mutant form comprises a mutation that removes or replaces the phosphorylatable hydroxyl groups found on the residue in question (for example, S67 and/or T75). In more specific embodiments, the T75 and/or S67 residue may be substituted or deleted.

For example, the mutant form may comprise at least one amino acid at a position that is a PKC-α phosphorylation site in the wild type protein, wherein the at least one amino acid is constitutively unphosphorylated. In a specific embodiment, the at least one amino acid is alanine (A), aspartic acid (D), or cysteine (C) at position 65 or alanine (A), aspartic acid (D), or cysteine (C) at position 75 in said mutant form of phosphatase protein. The amino acid substitutions may be selected based on similar charge (no charge), opting for conservative substitutions, and based on size (lack of bulk).

In another specific embodiment, the mutant form comprises at least one amino acid at a position that is a PKA phosphorylation site in the wild type protein, wherein the at least one amino acid is constitutively phosphorylated. For example, the at least one amino acid may be aspartic acid (D) or glutamic acid (E) at position 35 in said mutant form of phosphatase inhibitor-1 protein. Again, the amino acid substitutions may be selected based on similar charge (negative), as well as on size (lack of bulk).

In embodiments where it is desirable for a residue to mimic the phosphorylated state, such as with the use of a T35 mutant, mutations comprising the substitution of the residue for glutamic acid or aspartic acid are contemplated.

Nucleic Acid Molecules

Nucleic acid molecules of the invention include DNA molecules (e.g., linear, circular, cDNA or chromosomal DNA) and RNA molecules (e.g., tRNA, rRNA, mRNA) and analogs of the DNA or RNA generated using nucleotide analogs. The nucleic acid molecule can be single-stranded or double-stranded, but advantageously is double-stranded DNA. The nucleic acid molecule of the invention includes a nucleic acid molecule that is free of sequences that naturally flank the nucleic acid molecule (i.e., sequences located at the 5' and 3' ends of the nucleic acid molecule) in the chromosomal DNA of the organism from which the nucleic acid is derived. Moreover, an isolated nucleic acid molecule, such as a cDNA molecule, can be substantially free of other cellular materials when produced by recombinant techniques, or substantially free of chemical precursors or other chemicals when chemically synthesized.

A nucleic acid molecule of the present invention (for example, a nucleic acid molecule having the nucleotide sequence of SEQ ID NO: 3, 4, 9, 10, 15, and 17 can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*; Cold Spring Harbor Laboratory Press, Cold Spring Harbor, N.Y., (1989)) or can be isolated by the polymerase chain reaction using synthetic oligonucleotide primers designed based upon the sequence of, for example, SEQ ID NO: 3, 4, 9, 10, 15, and 17. A nucleic acid of the invention can be amplified using cDNA, mRNA or alternatively, genomic DNA, as a template and appropriate oligonucleotide primers according to standard PCR amplification techniques. In another embodiment, an isolated nucleic acid molecule of the invention comprises a nucleic acid molecule that is a complement of the nucleotide sequence shown, for example, in SEQ ID NO: 3, 4, 9, 10, 15, and 17.

The present invention may likewise feature recombinant nucleic acid molecules (e.g., recombinant DNA molecules) that include nucleic acid molecules described herein.

Polypeptides

Another aspect of the present invention features polypeptides.

It is well understood that one of skill in the art can mutate (e.g., substitute) nucleic acids that, due to the degeneracy of the genetic code, encode for an identical amino acid as that encoded by the naturally-occurring gene. This may be desirable in order to improve the codon usage of a nucleic acid to be expressed in a particular organism. Moreover, it is well understood that one of skill in the art can mutate (e.g., substitute) nucleic acids that encode for conservative amino acid substitutions. It is further well understood that one of skill in the art can substitute, add or delete amino acids to a certain degree without substantially affecting the function of a gene product as compared with a naturally-occurring gene product, each instance of which is intended to be included within the scope of the present invention.

In an embodiment, a polypeptide of the present invention has an amino acid sequence shown in SEQ ID NO: 5, 6, 11, 12, 16, and 18.

Sequence Identity

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

Gene Transfer/Delivery

Introduction is contemplated to be via any technology either known or currently unknown, that achieves the result of the desired introduction. The nucleic acids described herein can be incorporated into a gene construct to be used as a part of a gene therapy protocol. Methods for gene transfer in vivo are known in the art. Approaches include insertion of the subject gene in viral vectors including recombinant retroviruses, adenovirus (e.g., replication deficient, first generation, or gutted, second generation, adenovirus), adeno-associated virus (e.g., the viral capsid may be an AAV capsid such as AAV1, AAV2, AAV3, AAV4, AAV5, AAV6, AAV7, AAV8, AAV9, AAV10, or AAV11 capsid; one skilled in the art would know that there are, likely, other variants not yet identified that perform the same or similar function; or may include components from two or more AAV capsids, as described in U.S. Pat. No. 6,491,907), lentivirus, and herpes simplex virus-1, or recombinant bacterial or eukaryotic plasmids. To produce a lentiviral particle and other viral particles, the nucleic acid that encodes the agent of interest is operably linked to a packaging signal. The nucleic acid is packaged in cells that express viral structural proteins. For example, the cells can include nucleic acids that encode the viral structural proteins, but that lack a packaging signal.

Adeno-associated virus is a nonpathogenic human parvovirus, capable of site-specific integration into chromosome 19 (Fisher et al., *Nature Medicine* (1997). Replication of the virus, however, requires a helper virus, such as an adenovirus (Fisher et al., *Nature Medicine* (1997). An AAV coding region can be replaced with nonviral genes, and the modified virus can be used to infect both dividing and non-dividing cells (Xiao et al., *J. Virol.* (1996); Kaplitt et al., *Ann. Thorac. Surg.* (1996)). Exemplary methods for the preparation and use of AAVs are described in Fisher et al., *Nature Medicine* (1997) Xiao et al., *J. Virol.* (1996), Kaplitt et al., *Ann. Thorac. Surg.* (1996).

Different recombinant AAV genome structures are described in WO 01/092551, including duplexed parvovirus vectors—a parvovirus particle comprising a parvovirus capsid (e.g., an AAV capsid) and a vector genome encoding a heterologous nucleotide sequence, where the vector genome is self-complementary, i.e., the vector genome is a dimeric inverted repeat.

Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO.sub.4 precipitation carried out in vivo.

Gene transfer into cardiovascular tissue, for example, has been successful using adenovirus (Ad) vectors with strong, non-tissue specific gene expression cassettes driven by cytomegalovirus (CMV) or Rous sarcoma virus (RSV) promoters. Clinical trials involving transduction of cardiac cells with viral vectors to deliver angiogenic factors such as vascular endothelial cell growth factor (VEGF), fibroblast growth factor (FGF) and hepatocyte growth factor (HGF) have been ongoing. Intra-aorta or intracoronary injection of virus has been used in viva in animal models. As is known from studies on cystic fibrosis, transduction of all cells in a tissue is not required for improved function.

Tissue specific promoters have been used to increase specificity of myocardial gene expression (Rothmann, et al., *Gene Ther.* (1996)). Another strategy to restrict expression of transferred genes to the heart has involved direct injection of a viral vector into the myocardium (Gutzman, et al., *Cric. Res.* (1993); French, et al., (1994), *Circulation.* (1994)). Another attempt involved intrapericardial virus vector injection combined with proteinase treatment (Fromes, et al., *Gene Ther.*

(1999)). These manipulations achieved local gene delivery, although with some drawbacks, due to a lack of intense viral vector diffusion.

The efficiency of cardiomyocyte gene delivery by an adeno-associated virus (AAV) vector was documented in vitro using cultured rat neonatal cells, as well as in an ex vivo system using rat papillary muscle immersion (Maeda, et al., *J. Mol. Cell. Cardiol.* (1998)). Ex vivo AAV vector transfer followed by syngeneic heart transplantation was reported to achieve high efficiency marker gene expression (Svensson et al., *Circulation.* (1999)). Methods of achieving a high level of in vivo cardiotopic gene transfer with high consistency (average 60-70% of cardiac myocytes) are described, e.g., in US Published Application 20020032167. Other methods for the preparation and use of viral vectors are described in WO 96/13597, WO 96/33281, WO 97/15679, and Trapnell, et al., *Curr. Opin. Biotechnol.* (1994); Ardehali, et al., *J. Thorac. Cardiovasc. Surg.* (1995); Dalesandro, et al., *J. Thorac. Cardiovasc. Surg.* (1996); Sawa, et al., *Circ* (1995); Lee, et al., *J. Thorac. Cardiovasc. Surg.* (1996); Yap, et al., *Circ.* (1996); and Pellegrini, et al., *Transpl. Int.* (1998).

A subject polynucleotide can also be administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel, et al. *Am. J. Respir. Cell Mol. Biol.* (1992)). Thus "non-viral delivery vehicle" can include vectors composed of polynucleotides plus viral particles where the viral particles do not contain the polynucleotide of interest.

"Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed by Felgner, et al (U.S. Pat. Nos. 5,264,618 and 5,459,127; *PNAS* 84:7413-7417, (1987); *Annals N.Y. Acad. Sci.* (1995); they may also consist of neutral or negatively charged phospholipids or mixtures thereof including artificial viral envelopes as disclosed by Schreier, et al. (U.S. Pat. Nos. 5,252,348 and 5,766,625).

Non-viral delivery vehicles include polymer-based carriers. Polymer-based carriers may include natural and synthetic polymers and co-polymers. Preferably, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif, et al., *PNAS* 92:7297-7301, (1995)), which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

A preparation that includes units of a viral delivery system can be delivered to heart cells of a subject (in vivo or ex vivo) by any of a variety of methods known in the art.

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen, et al. *PNAS* 91: 3054-3057 (1994)).

Administration routes include intravenous, intradermal, subcutaneous, oral (e.g., inhalation or ingestion), transdermal (topical), and transmucosal. Also contemplated is injection, e.g., intra-arterially, intramuscularly, intra-pericardially, or intravenously.

In one exemplary implementation, the preparation is directly injected into heart tissue. U.S. Ser. No. 10/914,829 describes a protocol for direct injection. Direct injection or application of a viral vector into the myocardium can restrict expression of the transferred genes to the heart (Gutzman et al, *Cric. Res.* (1993); French et al., *Circulation.* (1994)). The preparation may also be provided to cells ex vivo. Cells containing the protein of interest (e.g., mutant I-1) are then administered to the patient.

In another exemplary implementation, the preparation is introduced into the lumen of one or more coronary arteries. Passage of blood out of the coronary arteries can be restricted. The preparation can be delivered antegrade and allowed to reside in the arteries for between one to five minutes, e.g., between one to three minutes.

In another exemplary implementation, the preparation is affixed to support matrices (e.g., sutures, surgically implanted materials, grafts, and the like) to provide controlled or uncontrolled release into the local tissue and/or vascular environment, as described in WO 01/091803.

Non-viral vehicles may be delivered by similar methods.

Pharmaceutical Compositions

An isolated nucleic acid molecule or polypeptide according to the invention can be incorporated into pharmaceutical compositions suitable for administration to a subject, e.g., a human. Such compositions typically include the polypeptide or nucleic acid molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the optimal particle size in the case of dispersion and by the use of surfactants. Prevention of the action of microorganisms can be achieved by various antibacterial and anti-fungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an isolated nucleic acid molecule as described herein) in the optimal amount in an appropriate solvent with one or a combination of ingredients enumerated above, followed by filtered sterilization. Generally, dispersions are prepared by incorporating the therapeutic agent into a sterile vehicle which contains a basic dispersion medium and other ingredients from those enumerated above. In the case of sterile powders for the preparation of sterile injectable solutions, preferred methods of preparation are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The therapeutic agent can be prepared with a carrier(s) that will protect it against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

The pharmaceutical preparation of the gene therapy construct can also comprise a slow release matrix in which the gene delivery vehicle is imbedded. Recombinant parvoviruses, and in particular, recombinant adeno-associated virus (rAAV), for example, can be used to deliver nucleic acid sequences (i.e., genes and DNA sequences) for gene therapy (as described above) following a dehydration or drying step (i.e., partial or complete desiccation, lyophilization), in which the therapeutic virus vector is dried onto (i.e., affixed to) a support matrix. Useful support matrices include surgically implantable materials (i.e., sutures, surgical graft material, implantable devices and the like) for packaging and transport to a subject, thus allowing delivery of gene therapy via the rAAV affixed to the support matrixes. This is described further in WO 01/091803. Alternatively, where the complete gene delivery system can be produced intact from recombinant cells, e.g. retroviral vectors, the pharmaceutical preparation can comprise one or more cells which produce the gene delivery system.

The nucleic acid molecule to be delivered can also be formulated as a DNA- or RNA-liposome complex formulation. Such complexes comprise a mixture of lipids that bind to genetic material (DNA or RNA) by means of cationic charge (electrostatic interaction). Cationic liposomes which may be used in the present invention include 3.beta.-[N—(N',N'-dimethyl-aminoethane)-carbamoyl]-cholesterol (DC-Chol), 1,2-bis(oleoyloxy-3-trimethylammonio-p-ropane (DOTAP) (see, for example, WO 98/07408), lysinylphosphatidyletha-nol-a-mine (L-PE), lipopolyamines such as lipospermine, N-(2-hydroxyethyl)-N,N-d-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy)propyl-N,N,N-triethylammonium (DOTMA), DOSPA, DMRIE, GL-67, GL-89, Lipofectin, and Lipofectamine (Thiery, et al. *Gene Ther.* (1997); Felgner, et al., *Annals N.Y. Acad. Sci.* (1995); Eastman, et al., *Hum. Gene Ther.* (1997)). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids that may be used include phosphatidylcholine, phosphatidylserine, phosphatidylethanolamine, sphingomyelin, phosphatidylinositol, and the like. Cholesterol may also be included.

Administration

A pharmaceutical composition as described above can be injected into an affected vessel, e.g., an artery, or an organ, e.g., the heart. In one method of treatment embodiment, flow of blood through coronary vessels of a heart is restricted and a viral delivery system is introduced into the lumen of a coronary artery. In a specific embodiment, the heart is permitted to pump while coronary vein outflow is restricted. In another specific embodiment, the viral delivery system is injected into the heart while restricting aortic flow of blood out of the heart, thereby allowing the viral delivery system to flow in to and be delivered to the heart. In other embodiments, the flow of blood through the coronary vessels is completely restricted, and in specific such embodiments, the restricted coronary vessels comprise: the left anterior descending artery (LAD, the distal circumflex artery (LCX), the great coronary vein (GCV), the middle cardiac vein (MCV), or the anterior interventricular vein (AIV). In certain embodiments, the introduction of the viral delivery system occurs after ischemic preconditioning of the coronary vessels.

In another embodiment, the viral delivery system comprising a vector is injected into the heart by a method comprising the steps of: restricting aortic flow of blood out of the heart, such that blood flow is re-directed to coronary arteries; injecting the vector into lumen of the heart, aorta or coronary ostia such that the vector flows into the coronary arteries; permitting the heart to pump while the aortic flow of blood out of the heart is restricted; and reestablishing the aortic flow of blood. In a more specific embodiment, the vector is injected into the heart with a catheter, and in an even more specific embodiment, the vector is directly injected into a muscle of the heart.

PKC-α inhibition constitutes a pharmacological target for treatment of heart failure, given that PKC-α activity is increased in the pathological state of heart failure. Hence, the administration of PKC-α antagonists or any agent which acts to inhibit PKC-α activity in combination with the nucleic acids or the polypeptides of the present invention. In conditions where it may be desirable to decrease cardiac contractility, administration of pharmacological agents which act as PKC-α agonists is additionally indicated.

Evaluation of Treatment

A treatment method of the invention can be evaluated by assessing the effect of the treatment on a parameter related to cardiac function or cardiac cellular function, e.g., without limitation, heart rate, cardiac metabolism, heart contractility, ventricular function, Ca2+ metabolism, and sarcoplasmic reticulum Ca2+ ATPase activity.

A treatment can also be evaluated by its effect on a subject, e.g., according to parameters that one skilled in the art of treatment would recognize as relevant for the particular treatment. For example, in treating heart failure, exemplary parameters may relate to cardiac and/or pulmonary function. Cardiac parameters include pulse, EKG signals, lumen loss, heart rate, heart contractility, ventricular function, e.g., left ventricular end-diastolic pressure (LVEDP), left ventricular systolic pressure (LVSP), $Ca^{2+}$ metabolism, e.g., intracellular $Ca^{2+}$ concentration or peak or resting $Ca^{2+}$, force generation, relaxation and pressure of the heart, a force frequency relationship, cardiocyte survival or apoptosis or ion channel activity, e.g., sodium calcium exchange, sodium channel activity, calcium channel activity, sodium potassium ATPase pump activity, activity of myosin heavy chain, troponin I, troponin C, troponin T, tropomyosin, actin, myosin light chain kinase, myosin light chain 1, myosin light chain 2 or myosin light chain 3, IGF-1 receptor, PI3 kinase, AKT kinase, sodium-calcium exchanger, calcium channel (L and T), calsequestrin or calreticulin. The evaluation can include performing angiography (e.g., quantitative angiography) and/or intravascular ultrasound (IVUS), e.g., before, after, or during the treatment.

Methods of Diagnosing/Prognosing Heart Failure

Additionally contemplated herein is diagnosing or prognosing heart failure in a subject by obtaining a sample of cardiac phosphatase inhibitor-1 protein from the subject and detecting the presence of at least one phosphorylated PKC alpha phosphorylation site, more specifically, wherein at least one phosphorylated PKC alpha phosphorylation site comprises T75 or S67. The diagnostic reagent may comprise the inventive isolated nucleic acid, or a complement or fragment thereof.

Kits

The isolated nucleic acid molecule or polypeptide of the invention can be provided in a kit. The kit may include, without limitation, (a) the nucleic acid molecule or polypeptide, e.g., a composition that includes the nucleic acid molecule or polypeptide, and (b) informational material. The informational material can be descriptive, instructional, marketing or other material that relates to the methods described herein and/or the use of the nucleic acid molecule or polypeptide of the invention for the methods described herein. For example, the informational material may relates to heart failure.

In one embodiment, the informational material can include instructions to administer the nucleic acid molecule or polypeptide of the invention in a suitable manner to perform the methods described herein, e.g., in a suitable dose, dosage form, or mode of administration (e.g., a dose, dosage form, or mode of administration described herein). In another embodiment, the informational material can include instructions to administer the nucleic acid molecule or polypeptide of the invention to a suitable subject, e.g., a human, e.g., a human having, or at risk for, heart failure. For example, the material can include instructions to administer the nucleic acid molecule or polypeptide of the invention to a subject who has or is at risk for having cardiomyopathy.

In addition to the isolated nucleic acid molecule or polypeptide of the invention, the composition of the kit can include other ingredients, such as a solvent or buffer, a stabilizer, a preservative, and/or a second agent for treating heart failure. Alternatively, the other ingredients can be included in the kit, but in different compositions or containers than the nucleic acid molecule or polypeptide of the invention. In such embodiments, the kit can include instructions for admixing the nucleic acid molecule or polypeptide of the invention and the other ingredients, or for using the nucleic acid molecule or polypeptide of the invention together with the other ingredients.

The nucleic acid molecule or polypeptide of the invention can be provided in any form, e.g., liquid, dried or lyophilized form. It is preferred that the nucleic acid molecule or polypeptide of the invention be substantially pure and/or sterile. When the nucleic acid molecule or polypeptide of the invention is provided in a liquid solution, the liquid solution preferably is an aqueous solution, with a sterile aqueous solution being preferred. When the nucleic acid molecule or polypeptide of the invention is provided as a dried form, reconstitution generally is by the addition of a suitable solvent. The solvent, e.g., sterile water or buffer, can optionally be provided in the kit.

The kit can include one or more containers for the composition containing the nucleic acid molecule or polypeptide of the invention. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent. For example, the kit includes a plurality of syringes, ampules, foil packets, or blister packs, each containing a single unit dose of the nucleic acid molecule or polypeptide of the invention. The containers of the kits can be air tight and/or waterproof. The kit optionally includes a device suitable for administration of the composition, e.g., a stent, syringe, or any useful delivery device.

Antibodies

Antibodies that selectively bind an isolated polypeptide comprising the amino acid sequence of SEQ ID NO: 5 or 6, or a constitutively unphosphorylated fragment thereof, are likewise contemplated. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

In one embodiment, an antibody that binds an isolated polypeptide comprising the amino acid sequence of SEQ ID NO: 5 or 6, or a constitutively unphosphorylated fragment thereof, is monoclonal. Alternatively, the antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "$F(ab')_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing an isolated polypeptide comprising the amino acid sequence of SEQ ID NO: 5 or 6, or a constitutively unphosphorylated fragment thereof, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an isolated polypeptide comprising the amino acid sequence of SEQ ID NO: 5 or 6, or a constitutively unphosphorylated fragment thereof, or immunogenic fragments thereof, can be provided to the host in a delivery vehicle that is taken up by immune cells of the host. The cells will, in turn, express the receptor on the cell surface generating an immunogenic response in the host. Alternatively, nucleic acid sequences encoding an isolated polypeptide comprising the amino acid sequence of SEQ ID NO: 5 or 6, or a constitutively unphosphorylated fragment thereof, or immunogenic fragments thereof, can be expressed in cells in vitro, followed by isolation of the receptor and administration of the receptor to a suitable host in which antibodies are raised.

Alternatively, antibodies against an isolated polypeptide comprising the amino acid sequence of SEQ ID NO: 5 or 6, or a constitutively unphosphorylated fragment thereof, may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

The present invention may be more fully understood by reference to the following supporting experiments and examples. However, it is understood that the examples are intended to elucidate certain aspects of the present invention, and should not be construed as limiting the scope of the invention as defined by the claims.

EXAMPLES

The present inventors undertook examination of PKC-α mediated phosphorylation of I-1, using purified proteins. cDNAs, encoding human I-1 or an I-1 mutant with alanine substitution at Ser-67 were cloned and expressed. The obtained recombinant proteins were purified and the GST-tag was removed. PKC-α phosphorylation of the pure proteins indicated that $^{32}$P-incorporation into the mutant is decreased but not completely abolished in comparison to the I-1 wild type, suggesting that there may be another PKC-α phosphorylation site. For identification of this putative PKC-α site, phosphorylated human I-1 was subjected to matrix-assisted laser desorption ionization mass spectrometry in combination with Edman degradation. These analyses revealed threonine-75 as a new PKC-α site on human I-1. To confirm this data, I-1 mutants with alanine substitutions at Thr-75 (T75A), and Ser-67 plus Thr-75 (S67A/T75A) were generated.

PKC-α treatment of I-1 and its mutants showed reduced $^{32}$P-incorporation into either S67A or T75A and none in the S67A/T75A mutant. Further analysis by two-dimensional electrophoresis corroborated that: 1) Thr-75 is a PKC-α site; and 2) Ser-67 and Thr-75 are the only residues phosphorylated by PKC-α on human I-1. To determine the functional significance of Thr-75 phosphorylation, protein phosphatase assays were performed. Phosphorylation of I-1 or I-1 mutants by PKA was associated with inhibition of PP1. However, PKC-α phosphorylation of I-1 had no effect on its activity. Furthermore, PKC-α phosphorylation had no effect on the PKA-mediated inhibitory function of I-1.

Materials

PKC-α, PKA and cAMP were purchased from Upstate Biotechnology. Phosphatidylserine was obtained from Avanti Polar-Lipids. The pGEX 6P-3 plasmid, Gluthathione Sepharose 4B, PreScission Protease and Immobiline DryStrips, IPG Buffer pH 4-7 were obtained from Amersham Biosciences. Quick-Change II site-directed mutagenesis kits and BL21 CodonPlus (DE3)-RIPL Competent Cells were obtained from Stratagene. Diacylglycerol, ampicillin and IPTG were obtained from Sigma-Aldrich. SYPRO Ruby Protein Gel Stain was obtained from Cambrex. T4 ligase, EcoRI and Not I restriction enzymes were purchased from New England Biolabs. Protein Desalting Spin Columns and B-PER GST Fusion Protein Purification Kit were purchased from Pierce. [γ-$^{32}$P] ATP was obtained from Perkin Elmer. Anti-AC1 was a custom-made (Affinity Bioreagents) rabbit polyclonal affinity-purified antibody against the N-terminal sequence of mouse I-1 ($^1$MEPDNSPRKIQFTVP$^{15}$) (SEQ ID NO: 24). Anti-GST rabbit polyclonal antibody was obtained from Affinity Bioreagents.

Methods

Generation of Inhibitor-1 Mutant Proteins

The human I-1 cDNA (GenBank Accession #U48707) was cloned into the pGEX-6P-3 vector in-frame with and on the C-terminal side of the Glutathione-S-Transferase (GST) gene (FIG. 1A). The forward cloning primer was: 5'-CAGA GAATTC C ATG GAG CAA GAC AAC AGC CC-3' (SEQ ID NO: 25) (EcoR I restriction enzyme site underlined; spacer nucleotide for in-frame expression shaded; start codon italicized), and the reverse cloning primer was: 5'-CAGA GCGGCCGC TCA GAC CGA GTT GGC TCC CT-3' (SEQ ID NO: 26) (Not I restriction enzyme site underlined; stop codon italicized). The PreScission Protease cleavage site was located between the GST and I-1 genes to facilitate subsequent removal of the GST tag. Mutations of the I-1 cDNA were obtained in the pGEX-6P3 vector; using the QuikChange II Site-Directed Mutagenesis Kit.

The primers used for mutagenesis of Ser-67 to Ala were: 5'-TCC ACT TTG GCA ATG GCA CCA CGG CAA CGG AAG AA-3' (SEQ ID NO: 27) (alanine codon underlined) and its complement (FIG. 1B). For mutagenesis of Thr-75 to Ala, the primers were: 5'-COG CAA AAG AAG ATG GCA AGO ATC ACA CCC AC-3' (SEQ ID NO: 28) (alanine codon underlined) and its complement. I-1 (S67A/T75A) was generated by using I-1 (S67A) as a template for mutagenesis of Thr-75 to Ala; the same set of primers described above for I-1 (T75A) was used (FIG. 1B). The primers used for mutagenesis of Ser-67 to Asp were: 5'-TCC ACT TTG GCA ATG GAC CCA CGG CAA CGG AAG AA-3' (SEQ ID NO: 29) (asparatate codon underlined) and its complement (FIG. 1C). For mutagenesis of Thr-75 to Asp, the primers were: 5'-CGG CAA CGG AAG AA ATG GAC AGG ATC ACA CCC AC-3' SEQ ID NO: 30) (aspartate codon underlined) and its complement (FIG. 1C). I-1 (S67D/T75D) was generated in a stepwise manner, as described above (FIG. 1C).

Each of these plasmids was transfected into BL21 Codon-Plus (DE3)-RIPL competent cells and grown on the LB-agar ampicillin (150 μg/ml) plates. Individual colonies were inoculated into 3-ml LB-ampicillin (50 μg/ml) starter cultures and grown at 37° C. for 16 hours. 1 ml of these cultures was inoculated into 100 ml of LB-ampicillin and grown at 25° C. for 2 hours. At this point, sterile IPTG was added to a final concentration of 0.1 uM and the cultures were grown for an additional 4 hours at 25° C. The cells were then pelleted, and the GST-I-1 fusion proteins were purified using the B-PER GST Fusion Protein Purification Kit. GST fusion proteins were extensively dialyzed against 50 mM Tris-HCl (pH 7.0) and incubated with PreScission Protease for 4 hours at 4° C. After proteolytic cleavage, the PreScission enzyme and GST tag were removed from the medium, using pre-washed Glutathione Sepharose 4B for 4 hours or overnight at 4° C. Samples were analyzed by SDS-PAGE using 15% polyacrylamide gels as described by Laemmli (24) to estimate the extent of cleavage and protein yield after purification. Protein concentration was determined by Micro BC assay (Pierce).

In Vitro Phosphorylation Assays

Reactions were conducted at 35° C. in 150 μl of buffer containing 7 μg of I-1 or I-1 mutant proteins. Recombinant I-1 or I-1 (S67A), I-1 (T75A), I-1 (S67A/T75A) mutants were phosphorylated by PKC-α. For PKC-α (3 μg/ml) phosphorylation, the final concentrations were 50 mM Tris-HCl (pH 7.0), 5 mM MgCl$_2$, 5 mM NaF, 0.5 mM CaCl$_2$, 0.3 mM phosphatidylserine and 0.02 mM 1,2-Diacyl-sn-glycero-3-phospho-L-serine. The phosphorylation reactions were initiated by the addition of 0.25 mM [γ-$^{32}$P] ATP (0.4 mCi/nmol). At indicated times, 20 ul was withdrawn from each mixture and the reactions were stopped by adding 4 ul of SDS sample buffer (5-strength) to the medium. For two-dimensional electrophoresis, 25 μg (35 μg in some cases) of protein were phosphorylated by PKC-α (4 ug/ml) in 100 μl of buffer at 35° C. for 45 minutes (or overnight in some cases), as described above. Reactions were initiated by the addition of 400 μM ATP. In all cases, Ca$^{2+}$ (1 mM EGTA present), Phosphatidylserine, diacylglycerol and PKC-α were omitted from the mixture for control samples.

Recombinant I-1 or I-1 (S67D/T75D) mutant (7 μg) were phosphorylated by PKA. PKA (0.1 μg) phosphorylation was performed in the presence of 50 mM Tris-HCl (pH 7.0), 5 mM MgCl$_2$, 5 mM NaF, 1 mM EGTA, 1 μM cAMP and 0.25 mM [γ-$^{32}$P] ATP (0.4 mCi/nmol) or 400 μM ATP. After 1 hour, the reactions were stopped by adding SDS sample buffer to the medium. For the control samples, PKA and cAMP were omitted from the reaction medium. The amount of [$^{32}$P]-phosphate into I-1 species was determined via SDS-PAGE and autoradiography or by trichloroacetic acid (20%, w/v) precipitation followed by dialysis. Densitometric analysis of the data was conducted using ImageQuant 5.2 software.

In initial experiments, PKC-α phosphorylated I-1 was observed to migrate as a doublet of phosphoproteins on autoradiographs. Further studies revealed that this occurred only upon PKC-α but not PKA phosphorylation (FIG. 2). This doublet was still observed when each of the two PKC-α phosphorylation sites was mutated to Ala (FIGS. 4 and 6). Interestingly, the doublet was related to the presence of the PKC-α activator, 1,2-diacyl-sn-glycero-3-phospho-L-serine (DAG), in the phosphorylation buffer (data not shown). This fact may be due to the alteration of the protein's net charge and, thus, reducing the binding of SDS.

Identification of Additional Phosphorylation Sites on Inhibitor-1

To identify novel PKC-α phosphorylation sites, 10 ug of GST-I-1 (purified I-1) were incubated in 50 µl of PKC-α phosphorylation buffer as described above in the presence of trace [$\gamma$-$^{32}$P] ATP for 4 h at 37° C. The reaction mixture was subjected to 12% SDS-PAGE and the gel was stained with SYPO Ruby overnight at room temperature. The $^{32}$P-labeled GST-I-1 band was identified, excised from the gel and subjected to trypsin digestion. Tryptic peptides were separated using a Vydac C18 reverse-phase HPLC column, and the fractions were immediately assayed for $^{32}$P by Cerenkov counting. Radioactive peaks were subjected to matrix-assisted laser desorption ionization/time-of-flight (MALDI-TOF) mass spectrometry and Edman degradation. The GPMAW program was used to match experimental peptide masses against the predicted peptides derived from the I-1 human sequence.

Immunoblot Analysis

I-1 species were separated by SDS-PAGE using 12% polyacrylamide gels. Following separation, proteins were transferred to nitrocellulose membranes (pore size 0.1 um) (Schleicher & Schuell Bioscience) by wet transfer (180 mA for 3 h). Nonspecific binding sites were blocked for 1-2 h at room temperature, using 5% dried milk in Tris-buffered saline (pH 7.4) containing 0.1% Tween 20. Membranes were probed for 3 h at room temperature or overnight at 4° C. with primary antibodies ACI (1:1000) for I-1 or anti-GST (1:1000). A secondary peroxidase-labelled antibody (Amersham Biosciences) was used in combination with an enhanced chemiluminescent detection system (Supersignal West Pico Chemiluminescent, Pierce) to visualize the primary antibodies. The optical density of the bands was analyzed by ImageQuant 5.2 software.

Two-Dimensional Electrophoresis

Purified I-1 or PKC-α- or PKA-phosphorylated I-1 and mutants were (once desalted using Protein Desalting Spin Columns) solubilized in rehydration buffer consisting of 7 M Urea, 2 M Thiourea, 4% CHAPS, 10 mM DTT, 1% IPG 4-7 Buffer and 0.01% bromophenol blue. The solubilized proteins were applied to 18 cm Immobiline™ Drystrips (pH 4-7NL) and incubated overnight at room temperature. The rehydration isoelectric focusing (IEF) was carried out for 60,000 volt-hours at 50 mA per strip on a Genomic Solutions Investigator 2-D Electrophoresis System. The second dimension was run on 12.5% slab gels for 14 hours at 500 V. The gels were fixed and stained with a fluorescent stain (SYRPO Ruby) overnight at room temperature. SYPRO stained gels were scanned using an FLA-3000 Imager (Fuji Medical Systems, Stamford, Conn.) with 475 nm fluorescent laser and a yellow 520 nm filter. For comparison purposes, 2-D gels were processed in parallel and subsequently, ProImage software was used to localize the spots to a standard set of coordinates. Therefore, gels can be compared to each other, and changes in the migration pattern of protein spots upon experimental manipulation can be easily detected.

Trichloroacetic acid precipitated protein samples from mouse cardiac homogenates were solubilized in DeSteak Solubilization buffer and subsequently applied to 11 cm IPG strips (pH 3-10) for isoelectric focusing. After protein separation in the second dimension using SDS-PAGE 12.5% proteins were transferred to nitrocellulose membranes (pore size 0.1 um) by wet transfer (180 mA for 3 h). The same procedure described above for immunoblot analysis of I-D gels was applied here.

Isolation of Inhibitor-1

I-1 was isolated from mouse cardiac muscle according to the procedure described by Shenolikar et al. (25) with modifications. Briefly, frozen tissues (1.5 g) was pulverized with a mortar in liquid nitrogen and homogenized with a Polytron homogenizer in 2 ml of ice-cold phosphate-buffered saline (pH 7.2). Immediately, 5 ml of 1.5% (w/v) trichloroacetic acid were added and the homogenate was rotated for 1 h at 4° C., before subjecting to centrifugation at 9,000 rpm for 30 min. The supernatant was adjusted to 15% (w/v) trichloroacetic acid, rotated at 4° C. overnight, and centrifuged at 18,000 rpm for 30 min. The pellet was resuspended in 0.5 M Tri-HCl, pH 8.0 (1/20 of the original extract volume), boiled for 10 min and centrifuged as above. The pH of the supernatant was adjusted to ~7, using IM NaOH, and the sample was subjected to 2-D gel electrophoresis.

Protein Phosphatase Activity Assays

Assays for protein phosphatase activity were performed in a 50 µl reaction mixture containing 50 mM Tris-HCl (pH 7.0), 0.1 mM Na$_2$EDTA, 5 mM DTT, 0.01% Brij 35, and, optionally, 0.5 ng of PP1 (New England BioLabs). The reaction was initiated by adding 10 ul of a standard substrate $^{32}$P-labeled Myelin Basic Protein (MyBP) (final concentration of 50 µM). To generate the $^{32}$P-MyBP substrate, commercially purified MyBP was previously phosphorylated by PKA to a stoichiometry of 2-4 mol phosphate per mol, following manufacturer's instructions (New England BioLabs) and stored at 4° C. After 10 min at 30° C., the reaction was terminated by adding 200 ul of 20% trichloroacetic acid, cooled on ice and centrifuged. The amount released [$^{32}$P] in the assay was determined by scintillation counting 200 ul from the supernatant. A blank reaction in which PP1 was omitted from the mixture was carried out in parallel.

To measure the I-1 inhibitory activity on PP1, I-1 wild type and its mutants (0.1 mg/ml) were phosphorylated prior to addition to the PP1 activity assay by PKC-α or PKA for the 1 h or overnight at 30° C. in the presence of 400 uM ATP as described above, omitting NaF from the assay medium. Dual phosphorylation by both kinases, PKA and PKC-α, was carried out stepwise as follows. After PKC-α incubation, an aliquot was withdrawn from the mixture and EGTA (a mM), cAMP (1 uM), PKA (0.1 ug) and ATP (400 uM) were added to the medium. The PKA phosphorylation reaction was incubated at 30° C. for the same time employed for PKC-α treatment. Subsequently, dephosphorylation of [$^{32}$P] MyBP by PP1 was monitored in the presence of dephosphorylated or phosphorylated I-1 or several I-1 mutants.

Generation of the I-1 Adenoviridae

Figure 3:
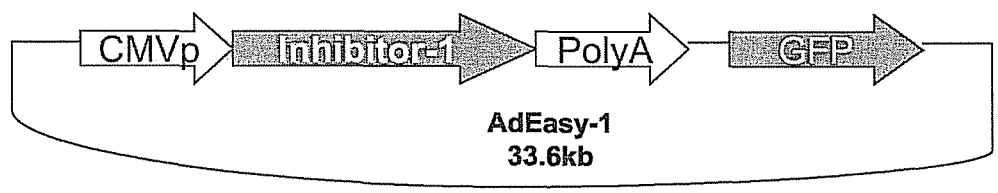
FIG. 3. Recombinant adenoviral vectors—Schematic diagram of recombinant adenoviridae expressing I-1. cDNAs were subcloned from the pGEX-6P-3 vector into the pSHUTTLE-IRES-hrGFP-1 vector and inserted into the AdEasy-1 viral backbone by homologous recombination.

To generate an ex vivo expression vector for assessment of the functional effects of phosphorylation of I-1 at a specific site, the I-1 cDNA bearing the specific mutation (for example, Thr-75 to Asp mutation (T75D)) was first cloned into the pShuttle-IRES-hrGFP-1 vector. This vector was allowed to homologously recombine with the AdEasy-1 adenovirus backbone vector (FIG. 3). Thus, the Ad-Easy XL system was used to generate adenoviruses encoding I-1 wild-type (Ad. I-1WT), I-1 mutants I-1(S67D), I-1(T75D), I-1 (S67D/T75D), or green fluorescent protein (Ad.GFP) in Ad-293 cells. This resulted in a replication-deficient recombinant adenovirus, which can express both I-1 (for example, the T75D mutant) and green fluorescent protein (GFP). The adenoviridae were amplified, purified (using the Adenovirus Mini Purification Kit (Virapur)), and titered (using the Adeno-X Rapid Titer Kit (Clontech)) according to standard procedures.

Adenovirus-Mediated Gene Transfer and Myocyte Contractility

To characterize the effects of phosphorylation of Inhibitor-1 at specific sites on cardiac contractility, ventricular myocytes from adult male Sprague-Dawley rats ($\approx$300 grams) were isolated by collagenase digestion as previously detailed (Fan et al. Circ. Res. (2004)). Rats were handled as approved by the Institutional Animal Care and Use Committee at the University of Cincinnati. Myocytes were resuspended in modified culture medium (M199, Gibco), counted, plated on laminin-coated glass coverslips or dishes, and infected with adenoviruses at a multiplicity of infection of 500 for 2 h, at 37° C. in a humidified 5% $CO_2$ incubator. Myocyte contraction at basal level and, optionally, under Forskolin (100 nM) (Sigma-Aldrich) treatment, was performed by using a Grass S5 stimulator (0.5 Hz, square waves) 24 h after infection. Fractional shortening (FS %), time to 90% relaxation (% of baseline) and maximal rates of contraction and relaxation ($dL/dT_{max}$) were calculated using a video edge motion detector (Crescent Electronics). For immunoblotting, cultured cardiomyocytes were harvested and lysed for 30 minutes at 4° C. in lysis buffer as described previously (Fan et al. Circ. Res. (2004)).

For immunoblotting, cultured cardiomyocytes were harvested and homogenized using a Polytron in solubilization buffer containing 50 mM Tris-HCl (pH 7.0), 10 mM NaF, 1 mM EDTA, 0.3 mM sucrose, 0.3 mM PMSF, 0.5 mM DL-Dithiothreitol (DTT) and protease inhibitor cocktail (1 ml per 20 grain of tissue) (Sigma). For measurement of protein phosphatase activity, NaF was omitted from the buffer.

Sarcoplasmic Reticulum $Ca^{2-}$ Uptake in Cultured Rat Cardiomyocytes

After 24 h infection of isolated rat cardiomyocytes, cells were washed twice with PBS, harvested and homogenized at 4° C. in 50 mM potassium phosphate buffer (pH=7.0), 10 mM NaF, 1 mM EDTA, 0.3 M sucrose, 0.3 mM PMSF and 0.5 mM DTT. Initial SR $Ca^{2+}$ uptake rates were determined in homogenates using the Millipore filtration technique and $^{45}CaCl_2$, as previously described (Kiss et al. Circ. Res. (1995)). Briefly, 100-250 μg of homogenate were incubated at 37° C. in reaction buffer containing 40 mM Imidazole (pH=7.0), 95 mM KCl, 5 mM $NaN_3$, 5 mM $MgCl_2$, 0.5 mM EGTA, and 5 mM $K_2C_2O_4$. The initial uptake rates were determined over a wide range of calcium values (pCa 5 to 8). Calcium uptake into cardiomyocytes was initiated by addition of 5 mM ATP, and aliquots were filtered through a 0.45 μm Millipore filter after 0, 30, 60 and 90 seconds to terminate the reaction. The specific $^{45}Ca^{2+}$ uptake values (maximum $Ca^{2+}$ uptake rate, $V_{max}$, and concentration of half-maximal Ca-uptake, $EC_{50}$) were analyzed using the OriginLab 5.1 program.

Autoradiography and Data Analysis

As mentioned briefly, above, the amount of $^{32}P$ incorporation into the I-1 species was determined by autoradiography. After wet transfer, nitrocellulose membranes were exposed to Blue Lite Autorad Films (IscBioExpress) for 24 or 48 h, and densitometric analysis of the data was conducted using Image Quant 5.2 software.

Statistics

All the values are expressed as mean±SEM for n experiments. Comparisons were evaluated by Student's t-Test for unpaired data or one-way ANOVA, as appropriate. *, $p<0.05$; , $p<0.01$; *, $p<0.001$.

Example 1

Phosphorylation of I-1 and I-1 Mutants by PKC-α

Figure 4A:
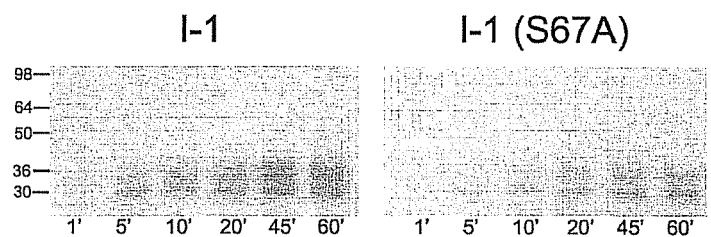
FIG. 4. Time course of phosphorylation of I-1 and I-1 (S67A) by PKC-α—PKC-α was used to phosphorylate I-1 and I-1 (S67A) in vitro. At the indicated times, 20 μl was withdrawn from each mixture, separated on 12% SDS-PAGE gels and transferred to nitrocellulose membranes. A) Autoradiograph depicting radiolabeled phosphoproteins. B) The same membranes were probed with AC1 antibody (1:1000) for detection of total I-1 and I-1 (S67A) proteins. C) Plot showing the ratio of $^{32}$P-incorporated (in both bands of A) per protein (in both bands, when present in B) at different times, quantified by densitometry and corrected for background. Data represent mean±S.D. of four independent experiments. In some cases, S.D. is smaller than the symbol size. , $p<0.01$; *, $p<0.001$.
Figure 4B:
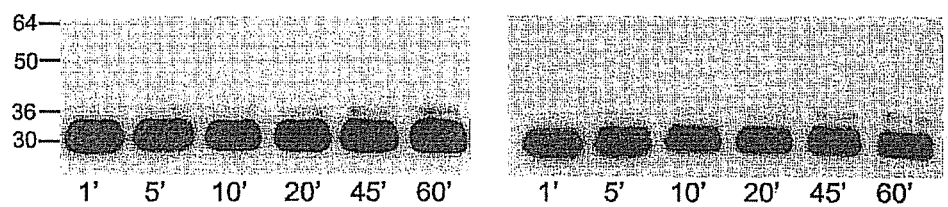
Figure 4C:
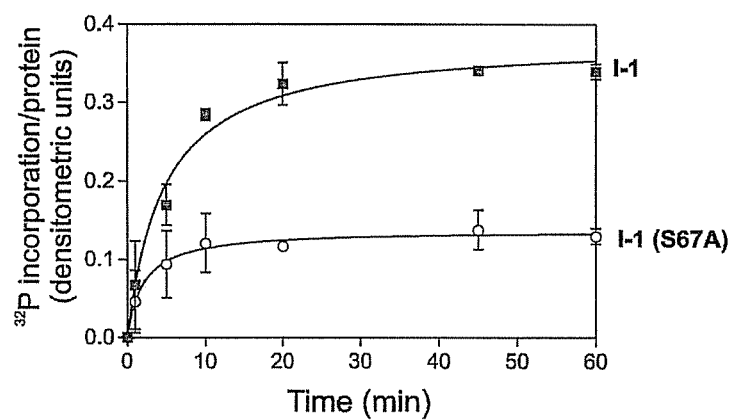

As noted, previous work showed that PKC-α phosphorylates inhibitor-1 (I-1) at Ser-67. To examine whether additional PKC-α phosphorylation sites may exist on I-1, an I-1 mutant in which Ser-67 was substituted with alanine was phosphorylated in vitro by PKC-α as described above. FIG. 4A shows that although PKC-α phosphorylation of the mutant I-1 (S67A) is greatly decreased in comparison to wild type I-1, it is not completely abolished. Densitometric analysis of $^{32}P$-incorporated per protein revealed that at steady-state (20-45 min), I-1 (S67A) incorporated 40±8.6% of the radioactivity levels present in wild types (100%) (FIG. 4C). In some of the experiments, a single additional band appeared at 78 Kda, which correspond to PKC-α autophosphorylation. No other radioactive bands were detected in any of the experiments. A specific antibody (AC1, 1:1000) recognized the phospho-bands as inhibitor-1 (FIG. 4B). Thus, these results indicate that at least one additional PKC-α phosphorylation site exists on I-1.

Example 2

Phosphorylation Site Determination

Figure 5A:
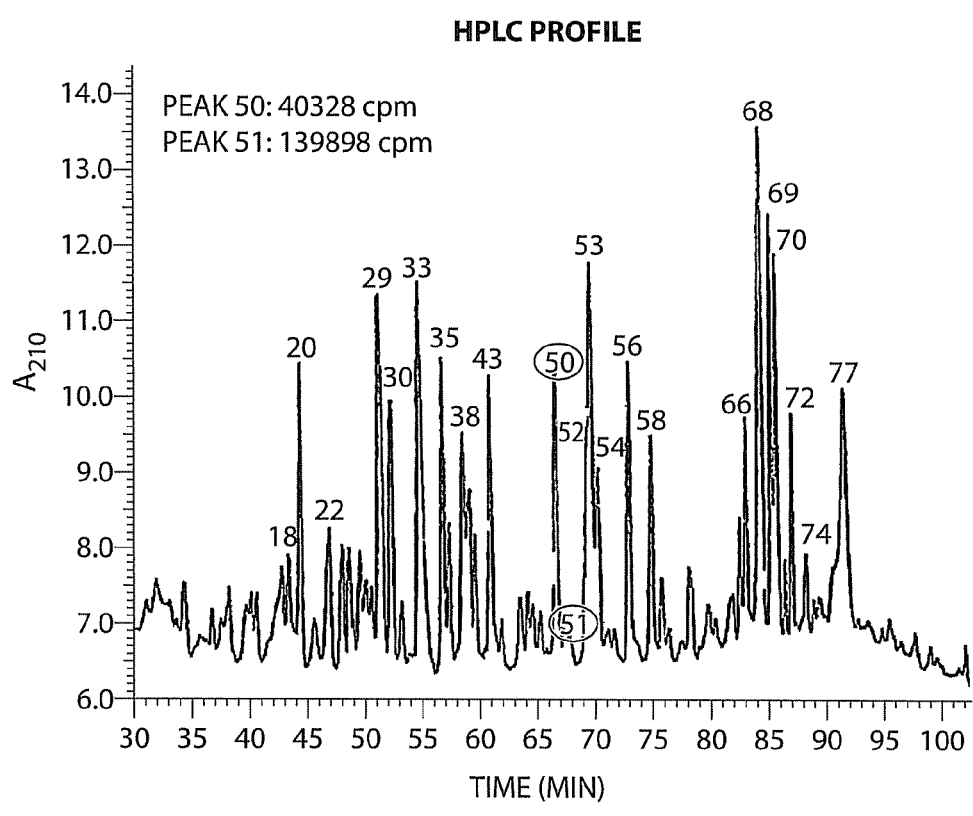
FIG. 5. Determination of phosphorylation sites—(A) Reverse-phase HPLC showing separation of the tryptic peptides numbered by HPLC fractions, with peaks 50 and 51 containing the majority of the radioactivity eluting from the column. (B) MALDI-TOF MS spectra showing a phosphorylated peptide with a mass of 1366.90 Da, corresponding to amino acids 73-82 of the human I-1 sequence (SEQ ID NO: 33). (C) A plot of the radioactivity eluted versus the amino acid position in each cycle of Edman degradation, showing that the majority of the isotope eluted with the fourth amino acid. This matches to the peptide $^{72}$KKMTRITPTMK$^{82}$ (SEQ ID NO: 23) detected in the MALDI-TOF data. The line graph shows mean±S.D. (n=three rounds of cpm counted). In most of the cases, S.D. is smaller than the symbol size. (D) Edman degradation detection of the isotope in the third amino acid of the identified sequence (SEQ ID NO: 33).

To determine the location of the additional PKC-α site (s) on I-1, recombinant purified I-1 was purified and subjected to in vitro phosphorylation by PKC-α in the presence of $[\gamma-^{32}P]$ ATP. The $^{32}P$-labeled I-1 was purified by SDS-PAGE, and digested with trypsin. After purification of the tryptic peptides by reverse-phase HPLC, two peaks, 50 and 51 (FIG. 5A), contained 62% of the radioactivity eluting from the Vydac column. Both fractions were subjected to MALDI-TOF mass spectrometry analysis. Mass matching analysis from fraction 51 yielded three potential phosphorylated peptides. The detected masses (predicted mass plus phosphate group) were 1226.44, 1494.45, and 1572.68 Da, which corresponded to each of the following I-1 sequences: $^{62}$STLAMSPRQR$^{71}$ (SEQ ID NO: 31), $^{72}$KKMTRITPTMK$^{82}$ (SEQ ID NO: 23), and $^{135}$KTAECIPKTHER$^{146}$ (SEQ ID NO: 32) (data not shown). In parallel, analysis of peak 50 detected a peptide of mass 1366.46 Da, which corresponded to the sequence $^{73}$KMTRITPTMK$^{82}$ (SEQ ID NO: 33) (same sequence found in peak 51 minus the first lysine) (data not shown).

Figure 5B:
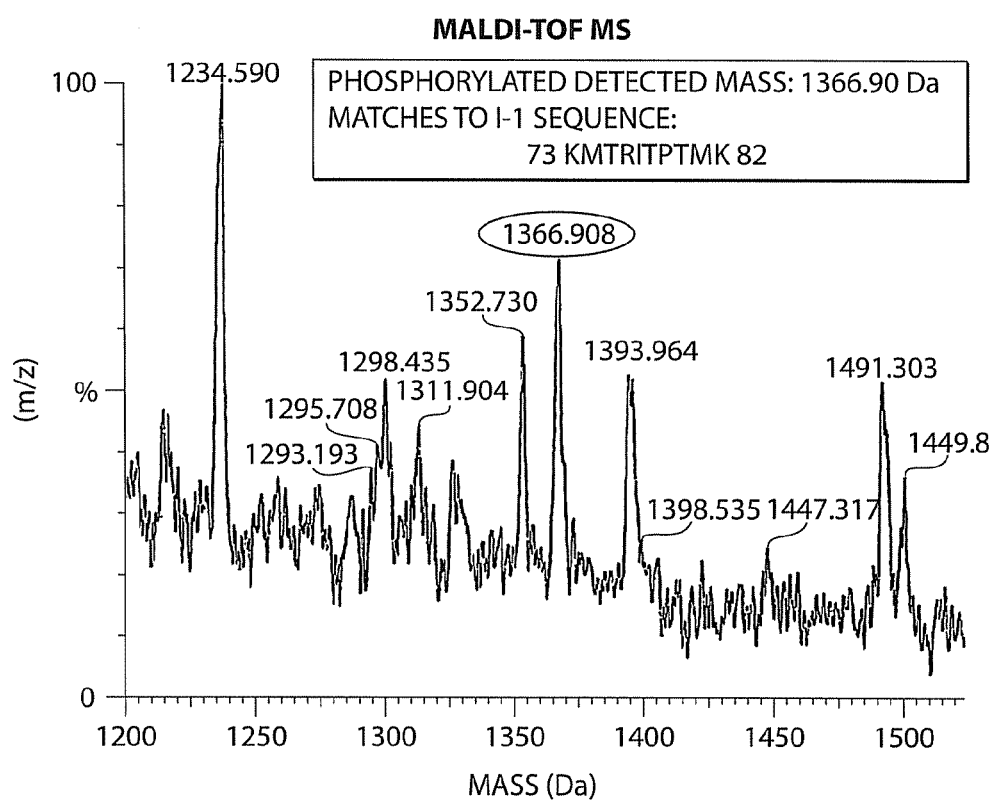
Figure 5C:
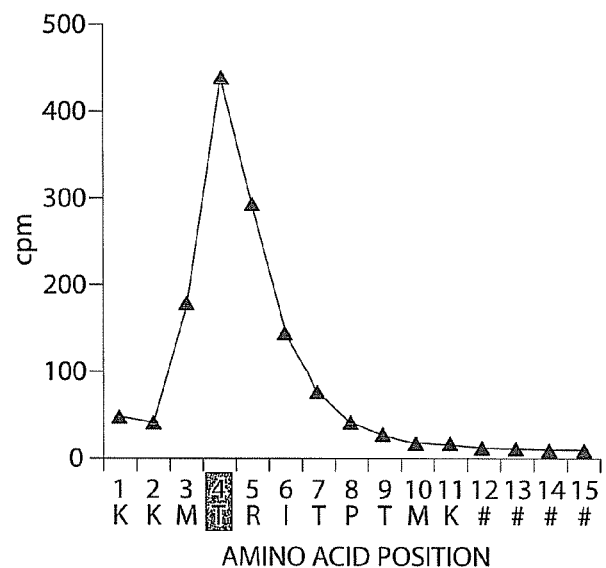
Figure 5D:
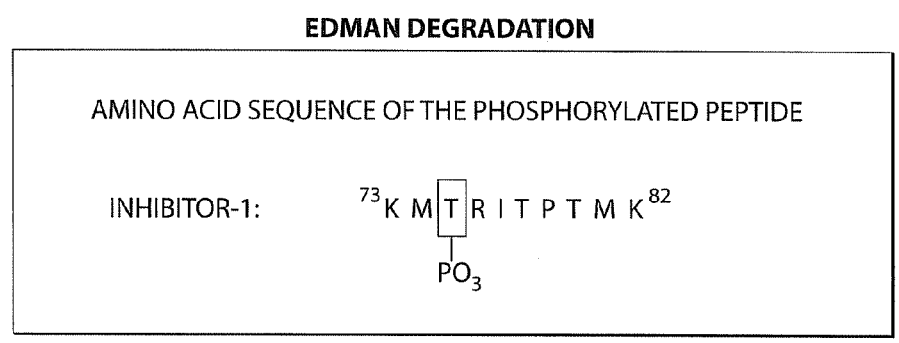

For the purpose of identifying the amino acid position of the phosphate group, Edman degradation was performed on fraction 51, since it contained more radioactivity compared to peak 50. The fifteen cycles of radio-sequencing carried out on this fraction, showed that the majority of the radioactive signal eluted with the fourth amino acid (approximately 370 cpm above background) (FIG. 5C). Subsequent reading of this result against the MALDI mass matches, showed that only the peptide $^{72}$KKMTRITPTMK$^{82}$ (SEQ ID NO: 23) possessed a phosphorylatable amino acid at position four (FIGS. 5B and 5C; phosphoamino is highlighted in a shaded box). A small amount of isotope eluted with the third amino acid (120 cpm), but this was likely due to an alternative trypsin cleavage between lysine 72 and 73 of I-1 ($^{73}$KMTRITPTMK$^{82}$ (SEQ ID NO: 33)). The amount of isotope detected in position 5 was due to the carryover of the previous site, a common artifact of this technique (usually about 50%). After cycle 4, the cpm decreased from cycle to cycle by roughly the same percentage. The peptide, corresponding to the sequence $^{73}$KMTRITPTMK$^{82}$ (SEQ ID NO: 33), was found to be phosphorylated at its third amino acid, Thr-75 (FIG. 5D). Thus, threonine-75 (Thr-75) was identified as a novel PKC-α phosphorylation site on human I-1.

Figure 6A:
FIG. 6. PKC-α phosphorylation in vitro showed that Ser-67 and Thr-75 are the primary PKC-α sites on purified human I-1—Purified human I-1, I-1 (S67A), I-1 (T75A) and I-1 (S67A/T75A) proteins were phosphorylated by exogenous PKC-α at different times. (A) Autoradiographs depicting radiolabeled phosphoproteins. (B) The same membranes were used to detect I-1 and I-1 mutant proteins by using AC1 antibody (1:1000). (C) Plot showing amount of $^{32}$P-incorporated into I-1 and I-1 mutant proteins, as quantified by densitometry and corrected for background at the corresponding phosphorylation time points shown in A. (D) Bar graph depicting the radioactivity associated with I-1 and its mutants at 45 min, as quantified by densitometry and expressed normalized to I-1 levels. The bars show mean±S.D. of three independent experiments. , $p<0.01$; *; $p<0.001$.
Figure 6B:
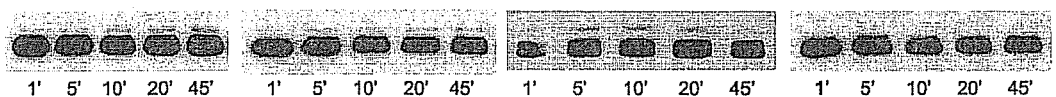
Figure 6C:
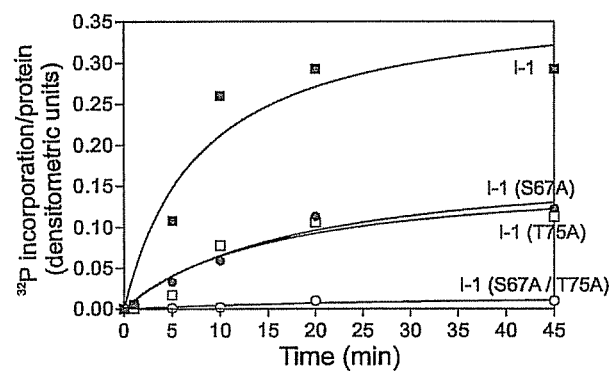
Figure 6D:
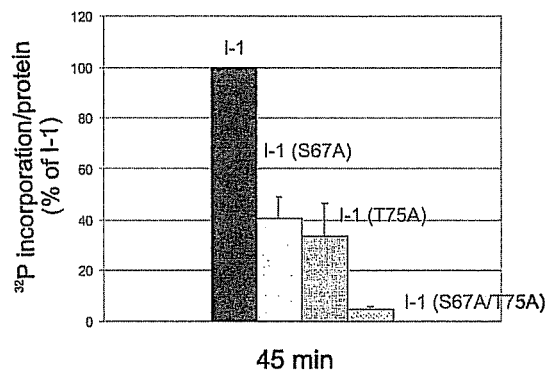

To further confirm the identity of Thr-75 as a phosphorylation site for PKC-α, and to determine whether Ser-67 and Thr-75 are the only PKC-α sites of human I-1, alanine substitution mutations at Thr-75 [I-1 (T75A)] and at Ser-67 plus Thr-75 [I-1 (S67A/T75A)] were made as described above. As shown in FIGS. 6 (A and C), the I-1 (T75A) mutant incorporated significantly less $^{32}$P upon PKC-α incubation in comparison to I-1 wild type. ACI antibody recognized all these phospho-bands as inhibitor-1 (FIG. 6B). Densitometric analysis of $^{32}$P-incorporated per protein at 45 min reveals that I-1 (T75A) incorporated 33.8±12.7% of the levels in wild type (100%) (FIG. 6D). I-1 wild-type was phosphorylated by PKC-α for 45 min to a stoichiometry of 0.88 mol Pi/mol protein, whereas the incorporation of Pi into I-1(S67A) and I-1(T75A) were reduced to 0.35 and 0.30 mol Pi/mol protein, respectively. FIGS. 6A, 6C, and 6D show incorporation of $^{32}$P into I-1 wild-type and mutants in in vitro time course reactions, expressed as densitometric units.

The results indicate that Thr-75 is, indeed, a PKC-α site on human I-1. Although the mutation of Thr-75 to Ala was associated with a greater decrease in $^{32}$P-incorporation, compared to the I-1 (S67A) mutant, this difference was not statistically significant (FIG. 6D). Therefore, PKC-α appears to phosphorylate human I-1 in vitro at Thr-75 to the same degree that it phosphorylates Ser-67. Moreover, mutation of both Ser-67 and Thr-75 to Ala abolishes $^{32}$P-incorporation into I-1 (FIGS. 6A, 6C, and 6D). These data indicate that, under the conditions described herein, these are two primary PKC-α phosphorylation sites on purified human I-1 protein.

Example 3

Analysis of PKC-α Phosphorylation of I-1 by Two-Dimensional Electrophoresis

Figure 7:
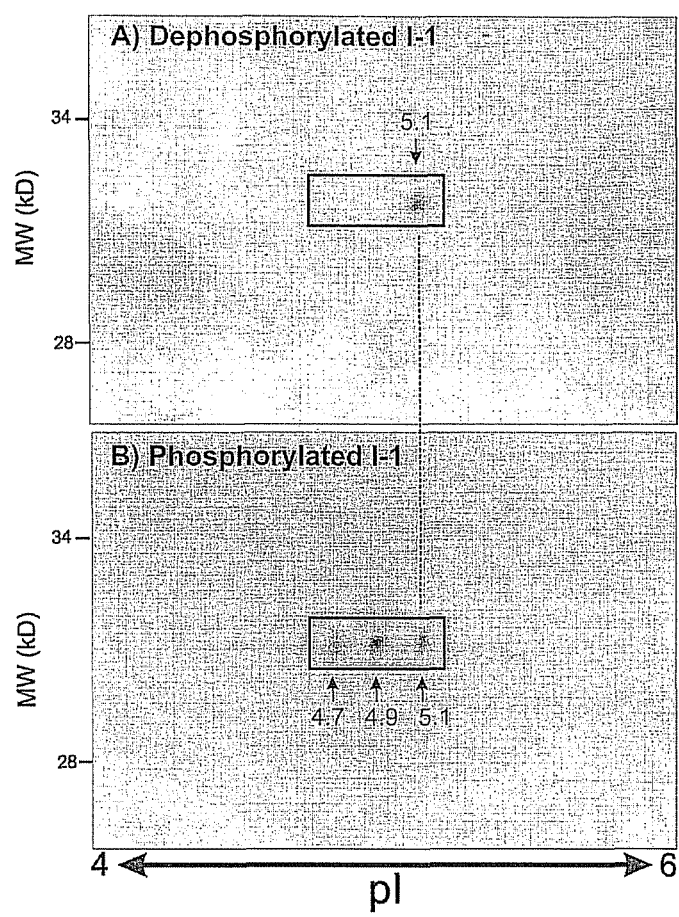
FIG. 7. Analysis of the phosphorylation status of purified human inhibitor-1 by two-dimensional electrophoresis—2-dimensional gels depicting migration shills (induced by PKC-α phosphorylation of I-1) to the left of protein spots with pI values (from right to left) of 4.9 and 4.7. The pI for I-1 dephosphorylated is 5.1 (n=3). Representative parts of 2-D gel images of I-1 samples are shown.

To further corroborate the autoradiography results, 2-D gel electrophoresis analysis was used to detect possible mobility changes in I-1 due to PKC-α phosphorylation. 2-D gel electrophoresis separates proteins based on both their isoelectric point (pI) and molecular weight. Phosphorylation causes the pI value of a protein to become more acidic, but has a negligible effect on its molecular weight. Analysis of the non-phosphorylated I-1 gel image indicated that the protein migrates in a 2-D gel as a single spot at a pI of 5.1 and molecular weight of ~30 kD (FIG. 7A). In the PKC-α phosphorylated sample, three spots were visible, with pIs of (from right to left): 5.1, 4.9 and 4.7, corresponding to non-phosphorylated, singly phosphorylated, and doubly phosphorylated protein, respectively (FIG. 7B). A higher concentration of phosphorylated I-1 (35 ug) subjected to 2D gel electrophoresis did not show any additional phosphorylation shifts (data not shown). Attempts to increase the degree of inhibitor-I phosphorylation by increasing the concentration of PKC-α, ATP or duration of the incubation time, did not reveal any additional phosphoprotein spots either. No other proteins spots were detected in the samples.

Figure 8A:
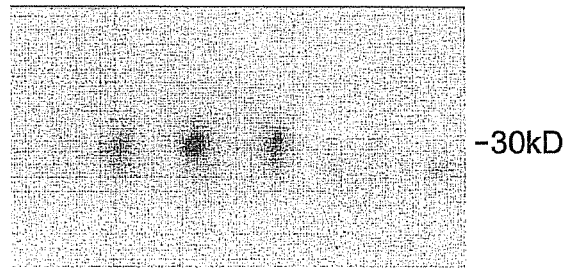
FIG. 8. 2-D gel electrophoresis corroborates that Ser-67 and Thr-75 are the two primary PKC-α phosphorylation sites on human I-1—Enlargements of relevant regions from 2-dimensional gels of I-1 samples are shown. (A) Phosphorylated I-1 wild type appears as three individual protein spots with pI values of 5.1, 4.9 and 4.7 (from right to left). (B) and (C) Two spots with pIs of 5.1 and 4.9 were observed when Ser-67 or Thr-75 on I-1 was substituted by alanine. (D) The simultaneous mutation of Ser-67 and Thr-75 abolished any pI migration shift of the protein. A single spot with a pI of 5.1 appears in the 2-D gel. Dotted circles indicate the expected location of phosphorylated species in each I-1 mutant in comparison with the wild type. Each 2-D gel was performed 3 times using purified proteins from different phosphorylations assays.
Figure 8B:
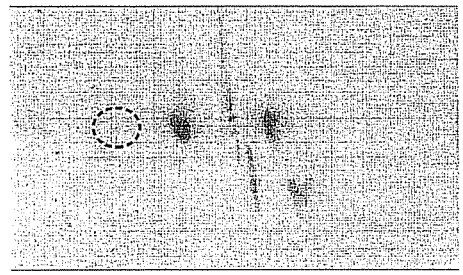
Figure 8C:
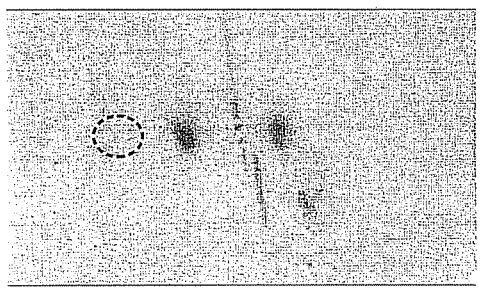
Figure 8D:
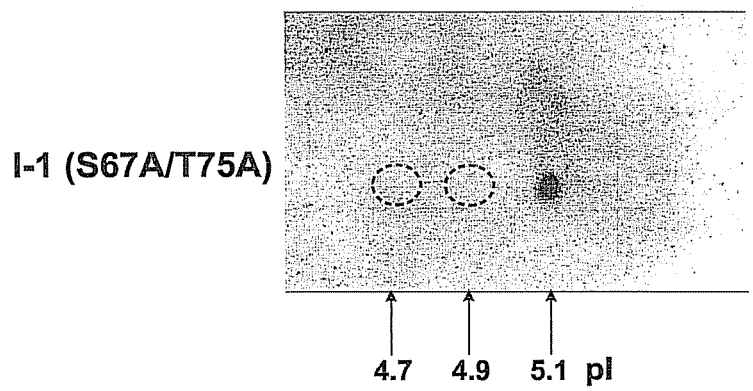

Since the studies above indicated that Thr-75 is a new phosphorylation site for PKC-α, purified human I-1 wild type, I-1 (S67A), I-1 (T75A) and I-1 (S67A T75A) proteins were incubated with PKC-α and subjected in parallel to 2-D gel electrophoresis. When either Ser-67 or Thr-75 were mutated to Ala, only two spots with pI values of 5.1 and 4.9 were detected in the gels (FIGS. 8B and 8C). These data demonstrated that blocking one of the two PKC-α sites prevented the incorporation of phosphate into the protein, resulting in a two-spot pattern in contrast to the three-spot observed in phosphorylated I-1 wild-type (FIG. 8A). Moreover, simultaneous mutation of Ser-67 and Thr-75 completely abolished any migration shift of I-1 to the left (FIG. 8D), further establishing that: 1) Thr-75 is a PKC-α site; and 2) Ser-67 and Thr-75 are the primary PKC-α sites on human I-1.

Example 4

Effects of PKC-α Phosphorylation on I-1 Function

Figure 9A:
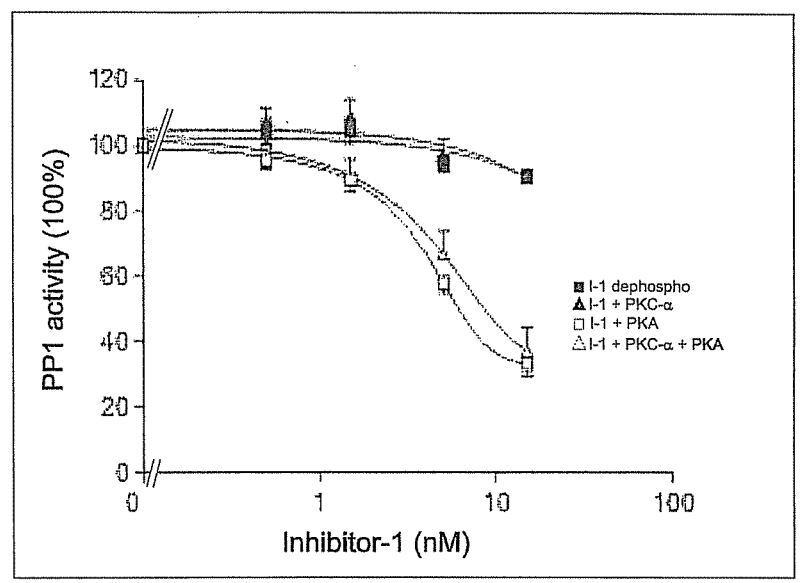
FIG. 9. Effect of PKC-α and PKC phosphorylation of I-1 or I-1 mutants on PP1 activity—Plots depicting I-1 inhibitory activity on PP1 monitored in the presence of: (A) Dephospho-I-1 (filled squares), PKC-α-phospho-I-1 (filled triangles), PKA-phospho-I-1 (open squares), and PKC-α+PKA-phospho-I-1 (open triangles); (B) PKC-α-phosphorylated: I-1 (S67A) (filled squares), I-1 (T75A) (filled triangles), and I-1 (567A/T75A) (filled circles); and PKA-phosphorylated: I-1 (S67A) (open squares), I-1 (T75A) (open triangles), and I-1 (S67A/T75A) (open circles). The activity (nmol/min/ml) associated with each I-1 species is normalized to the PP1 activity in the absence of I-1 or its mutants. Quantified values represent the average of 7 different experiments performed in duplicate (mean±S.D.).

Previous studies have reported that I-1 inhibits PP1 only upon phosphorylation by PKA (6-8). Based on the present finding that PKC-α independently phosphorylates I-1 to the same extent on two sites, Ser-67 and Thr-75, the effect of PKC-α phosphorylation on the function of I-1 was examined. In these studies, I-1 wild type untreated or I-1 wild type phosphorylated by: PKC-α, PKA or PKC-α+PKA was used in protein phosphatase assays (FIG. 9A). Neither dephospho-I-1 nor PKC-α-phospho-I-1 inhibited PP1 activity at any of the concentrations tested (0-15 nM). However, PKA-phosphoI-1 inhibited PP1 with an $IC_{50}$ value of 3.2±0.08 nM, consistent with previous reports (7-9).

Figure 9B:
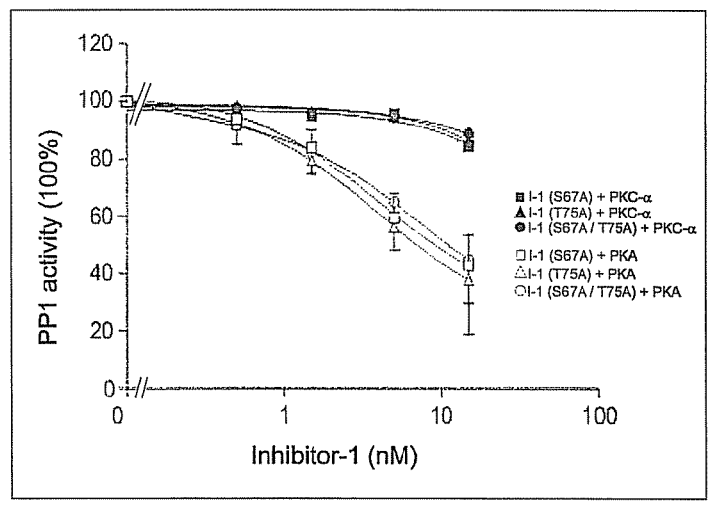

To investigate whether PKC-α phosphorylation may affect the inhibitory function of PKA-phospho-I-1, I-1 wild type was first phosphorylated by PKC-α and then by PKA as described above. As shown in FIG. 9A, pre-phosphorylation by PKC-α had no effect on the PKA-mediated inhibitory function of I-1 ($IC_{50}$ value of 4.9±0.74 nM). Furthermore, none of the following mutants: I-1(S76A), I-1 (T75A) or I-1 (S67-A/T75A) had any inhibitory effect on PP1 function following their phosphorylation by PKC-α (FIG. 9B).

To further corroborate these results, aspartate substitution mutations, which mimic phosphorylation of I-1 (9, 12), were made at Thr-75 [I-1 (T75D)] and at Ser-67 plus Thr-75 [I-1 (S67D/T75D)] as described in above. None of these mutations had any inhibitory effect on PP1 activity. Thus, although PKC-α can phosphorylate I-1 at two distinct sites, these phosphorylations do not inhibit PP1 activity. However, upon PKA phosphorylation, all of these I-1 species were capable of fully inhibiting PP1 activity (FIG. 9B).

Example 5

Analysis of the Phosphorylation Status of Inhibitor-1 from Mouse Cardiac Tissue

Figure 10:
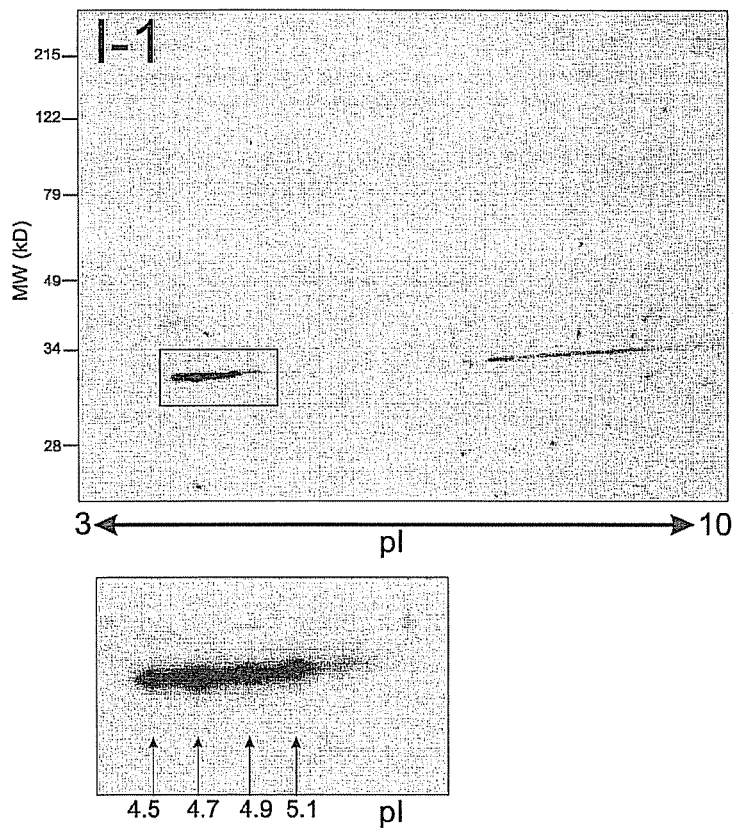
FIG. 10. Two-dimensional Western blot of I-1 in vivo—2-dimensional Western blot depicting proteins separated based on pI (isoelectric point) and molecular weight. Enlargement of the boxed region from 2-D gels is shown below the panel.

It was previously reported that inhibitor-1 is phosphorylated in vivo at only two positions, Thr-35 and Ser-67. In an effort to investigate if Thr-75 is also phosphorylated in vivo, a fraction enriched in I-1 was isolated from mouse cardiac muscle (1.5 g), as described above. The final pellet (~0.25% of the initial protein) was subjected to 2-D gel electrophoresis. After the second dimension of electrophoresis, the proteins were electroblotted onto a nitrocellulose membrane and incubated with the antibody AC1 (1:1000) for I-1. As shown in FIG. 10, four protein spots with pI values of 5.1, 4.9, 4.7 and 4.5 (from right to left) were identified. The streak detected on the right part of the membrane was due to incomplete isoelectric focusing of the protein, and it was observed due to the increased sensitivity of immunoblotting.

Analysis of this image, using ProImage software, indicated that the spot with a pI of 5.1 corresponded to dephosphorylated recombinant I-1. These results demonstrated that I-1 is post-translationally modified three times in vivo under basal conditions. Given that Thr-35 and Ser-67 are known to be phosphorylated in vivo, and that the isoelectric point shifts of I-1 are equivalent to those observed using recombinant protein, the four spots likely represent dephosphorylated I-1 and I-1 phosphorylated at one, two and three sites (Thr-35, Ser-67 and Thr-75).

Example 6

I-1 Mutations and Cardiac Contractility

Figure 11:
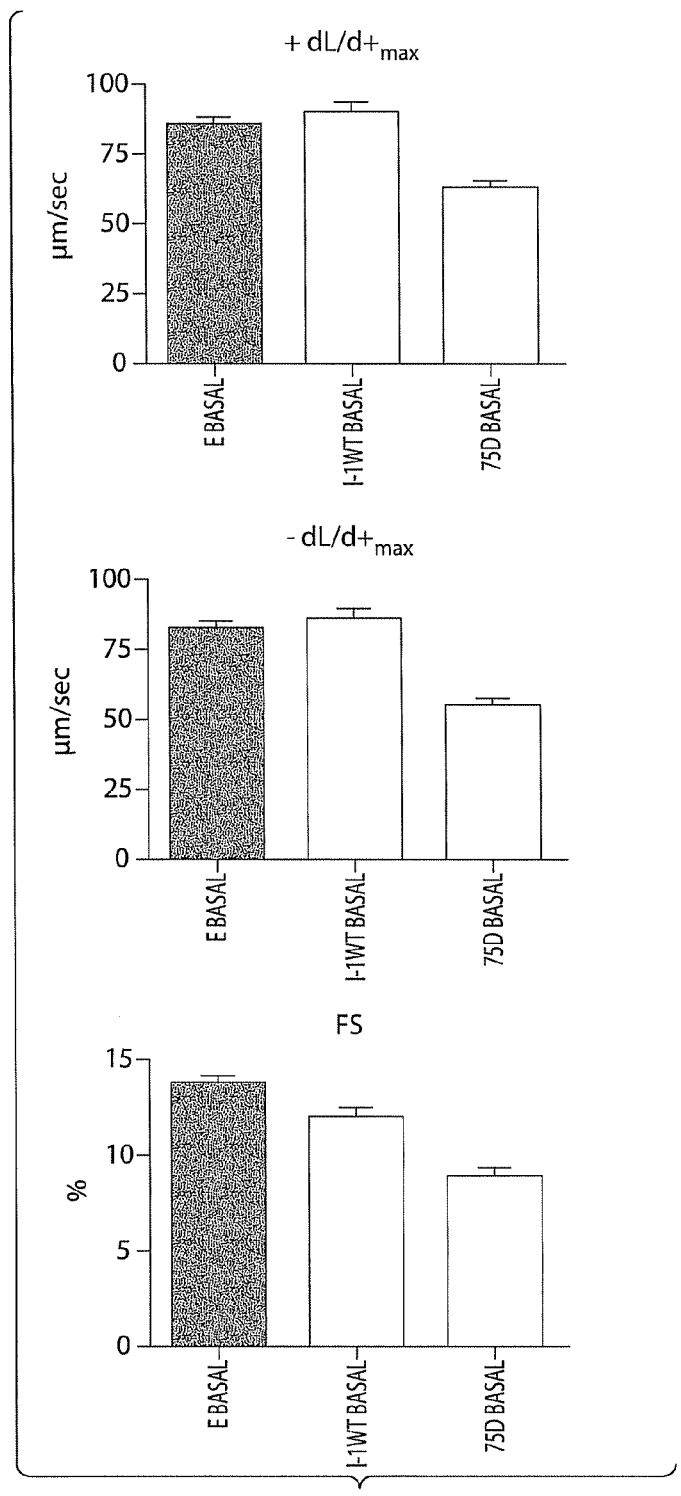
FIG. 11. Basal Cardiac Myocyte Contractility (T75D mutation)—Bar graphs depicting change in cardiac contractility (over time) as a function of the T75D mutation in I-1. Rate of myocyte contraction is referred to as +dL/dtmax; rate of myocyte relaxation is referred to as –dL/dtmax; contractile force generated is referred to as FS.

To test the effect of I-1 mutations on cardiac contractility, adult rat cardiomyocytes were infected with recombinant adenovirus expressing either wild-type I-1, I-1 or T75D under the control of the CMV promoter. Empty vector was used as a control. The rates of myocyte contraction and myocyte lengthening were determined after stimulation by a Grass S5 stimulator (0.5 Hz, square waves). Expression of I-1 T75D significantly reduced the rates of myocyte contraction (+dL/dtmax decreased by 29%) and myocyte relaxation (−dL/dtmax decreased by 33%) (FIG. 11). Furthermore, the total contractile force generated by myocytes expressing the mutant protein was reduced 35% or more. The data indicates that phosphorylation at T75 inhibits contractile functioning in the heart.

Figure 12:
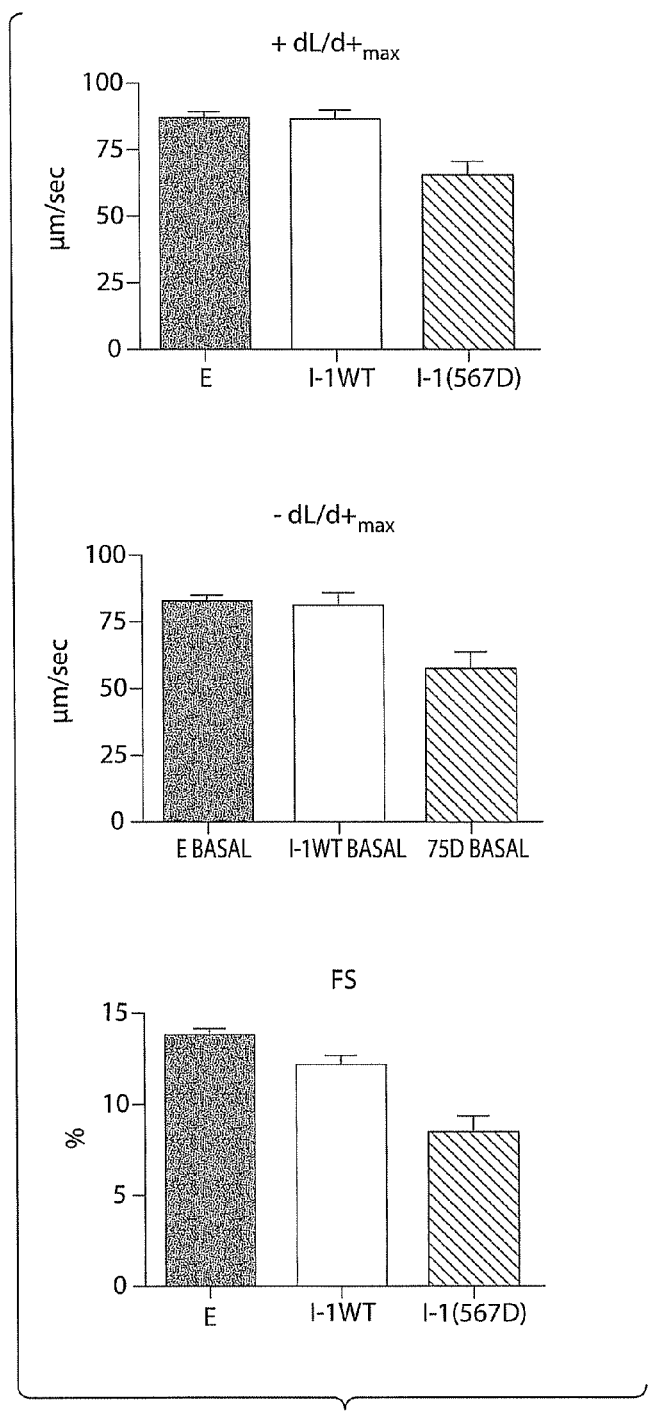
FIG. 12. Basal Cardiac Myocyte Contractility (S67D mutation)—Bar graphs depicting change in cardiac contractility (over time) as a function of the S67D mutation in I-1. Rate of myocyte contraction is referred to as +dL/dtmax; rate of myocyte relaxation is referred to as –dL/dtmax; contractile force generated is referred to as FS.

To test the effect of the S67D mutation on cardiac contractility, adult rat cardiomyocytes were infected with recombinant adenovirus expressing either wild-type I-1, or I-1 S67D under the control of the CMV promoter. Empty vector was used as a control. The rates of myocyte contraction and myocyte lengthening were determined after stimulation by a Grass S5 stimulator (0.5 Hz, square waves). Expression of I-1 S67D significantly reduced the rates of myocyte contraction (+dL/dtmax decreased by 24%) and myocyte relaxation (−dL/dtmax decreased by 28%) (FIG. 12). Furthermore, the total contractile force generated by myocytes expressing this mutant protein was reduced 35% or more (38%, FIG. 12). This data indicates that phosphorylation at S67 negatively impacts contractile function in the heart.

Figure 13A:
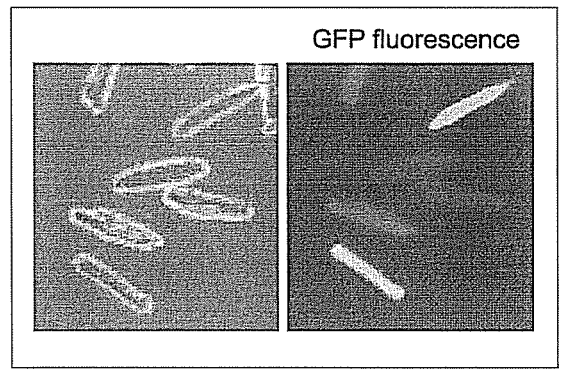
FIG. 13. PKC-α phosphorylation of I-1 at Thr-75 depresses cardiomyocyte contractility—(A) Images of rat cardiac myocytes 24 hrs after infection at a MOI of 500. Right image shows green fluorescent protein (GFP) expression. (B) I-1 antibody (AC1; 1:1000)-detected overexpression of the protein in cardiomyocyte lysates infected with Ad.I-1WT and Ad.I-1 (T75D). The same membrane was stripped and probed for PP1 (Santa Cruz, 1:1000). Coomassie-staining of the upper part of the same gel demonstrates equal protein loading and band pattern. (C) Representative traces of cardiomyocyte mechanics in Ad.GFP (continuous black line), Ad.I-1WT (discontinuous line), and Ad.I-1(T75D) (continuous grey line). Time to 90% relaxation, fractional shortening (FS %), and maximal rates of contraction and relaxation ($dL/dt_{max}$) are shown in bar graph form. Total number of cells: 121 (Ad.GFP), 90 (Ad.I-1 WT) and 91 (Ad.I-1(T75D)) from 6 hearts. Values represent means±SEM. (C-2) Fractional shortening (FS %), and maximal rates of contraction and relaxation (dL/dt.sub.max) are shown in bar graph form.
Figure 13B:
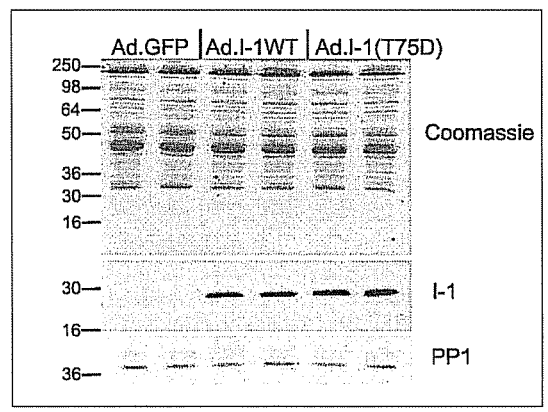

Next, adult rat cardiomyocytes were infected with either the I-1 wild-type adenovirus, Ad.I-1WT, or the constitutively phosphorylated I-1 at Thr-75, Ad.I-1(T75D). An adenovirus expressing only GFP, Ad.GFP, was used as control. Infection efficiency reached nearly 100% after 24 h, as assessed by green fluorescence (FIG. 13A). Ad.I-1WT and Ad.I-1(T75D) showed the expected overexpression of I-1, whereas endogenous I-1 was undetectable in cells infected with Ad.GFP (FIG. 13B).

Figure 13C:
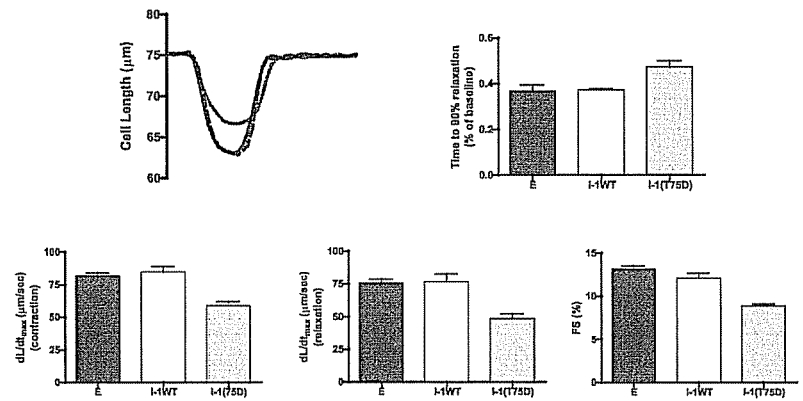
Figures 2, 13C:
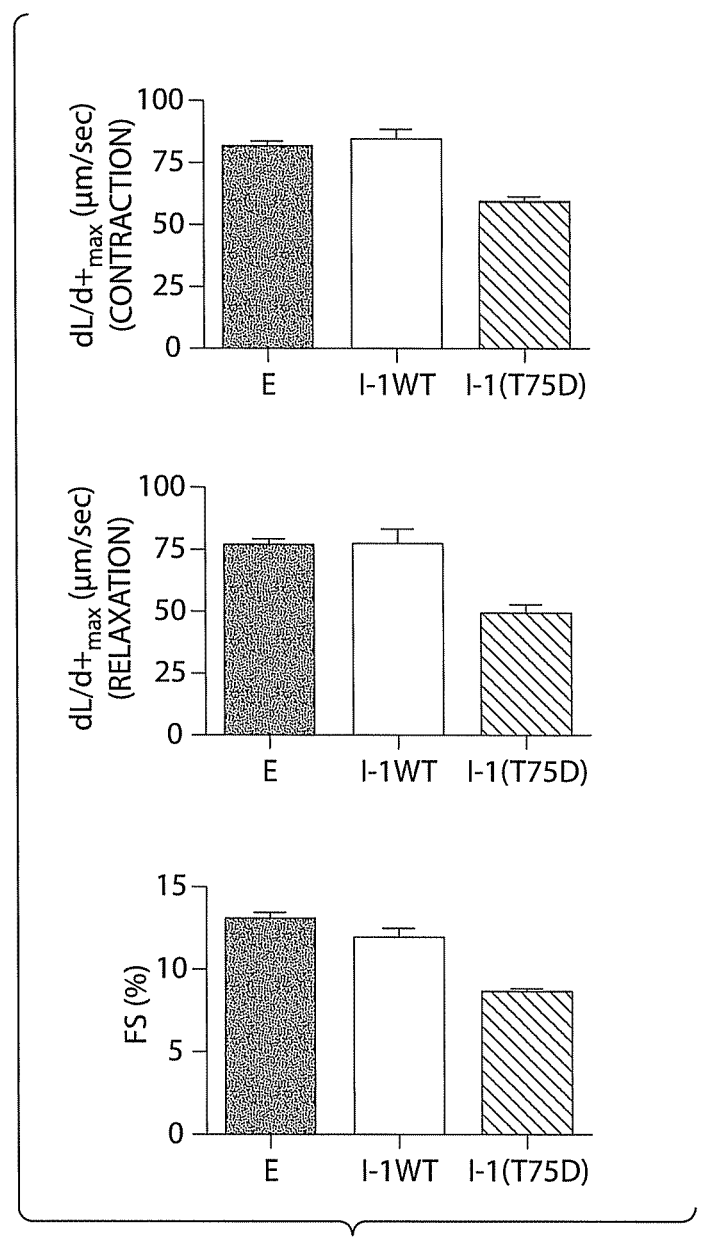

Constitutive phosphorylation of I-1 at Thr-75 induced a marked attenuation in the maximum rates of myocyte shortening ($dL/dt_{max}$; 31%) and relengthening ($dL/dt_{max}$; 36%), as well as in the fractional shortening (33%), compared with either I-1-infected wild-type or GFP-infected cells (FIG. 13C). Time to 90% relaxation was significantly increased (by 22%) in Ad.I-1(T75D) infected myocytes. These findings indicate that phosphorylation of I-1 at Thr-75 significantly depresses myocyte contractility.

Figure 14A:
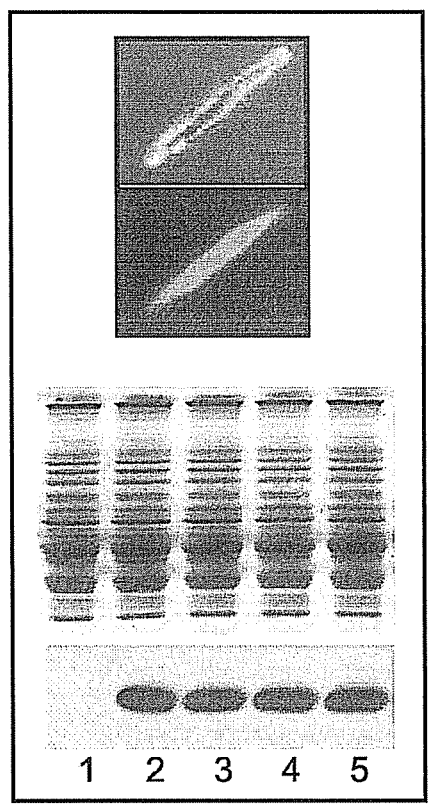
FIG. 14. Phosphorylation of I-1 at Ser-67 and/or Thr-75 depresses myocytes cardiac function—(A) Image of an adult rat cardiomyocyte 24 hrs after adenoviral infection at a MOI of 500. An antibody specific for I-1 (AC1; 1:1000) was used to detect overexpression of the protein in myocytes infected with: 1) GFP; 2) I-1WT; 3) I-1(S67D); 4) I-1(T75D); and 5) I-1(S67D/T75D). The upper part of the gel was stained with Coomassie-blue to demonstrate equal protein loading. (B) Fractional shortening (FS %) and maximal rates of contraction and relaxation ($dL/dt_{max}$, µm/sec) of adenoviral infected-cardiomyocytes are shown in bar graph form.

Next, adult rat cardiomyocytes were infected with Ad.GFP, Ad.I-1WT, Ad.I-1(S67D), Ad.I-1(T75D) and Ad.I-1(S67D/T75D). Adenoviral transfection efficiency was assessed after 24 hours by green fluorescence and Western blot immunodetection. As shown in FIG. 14A, the levels of I-1 expression were similar in all the groups, whereas endogenous was undetectable in cells infected with Ad.GFP, similar to previous observations (Rodriguez et al. *J. Biol. Chem.* (2006), El-Armouche et al. *Cardiovasc. Res.* (2001)). Consistent with recent findings (Rodriguez et al. *J. Biol. Chem.* (2006)), expression of the Ad.I-1 (T75D) in cultured myocytes significantly reduced the rates of contraction and relaxation (29% and 35.5%, respectively), as well as fractional shortening (29%), compared to myocytes expressing Ad.I-1WT (FIG. 14B). 15-20 myocytes/heart were analyzed with a total number of hearts per group of: 12 (Ad.GFP), 6 (Ad.I-1 WT), 5 (Ad.I-1(S67D)), 8 (Ad.I-1(T75D)); and 5 (Ad.I-1(S67D/T75D)).

Figure 14B:
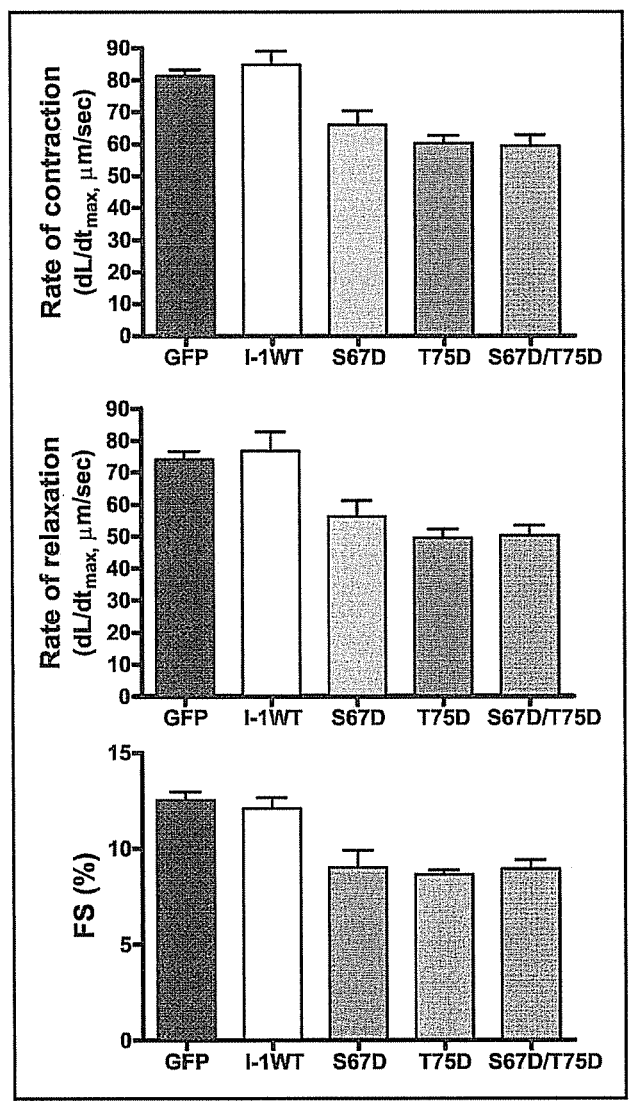

Expression of the Ad.I-1(S67D) induced similar decreases in the rates of myocyte contraction (22.1%) and relaxation (27%), as well as fractional shortening (25.3%) (FIG. 14B). Although the functional performance of myocytes expressing Ad.I-1 (T75D) tended to be more attenuated than those expressing Ad.I-1 (S67D), the values were not different statistically. Interestingly, expression of the constitutively dual phosphorylated I-1 at S67D and T75D, Ad.I-1(S67D/T75D), yielded similar results to those elicited by each of the single mutants. Ad.I-1 (S67D/T75D) reduced the maximal velocities of contraction and relaxation by 30% and 34.5%, respectively. Fractional shortening was reduced by 26.1%, compared to Ad.I-1WT (FIG. 2B). These results indicate that phosphorylation of either Ser-67 or Thr-75 on I-1 exerts similar decrease on myocyte contractility, resulting in no further depression of the contractile parameters, when both sites are simultaneously phosphorylated.

Figure 15:
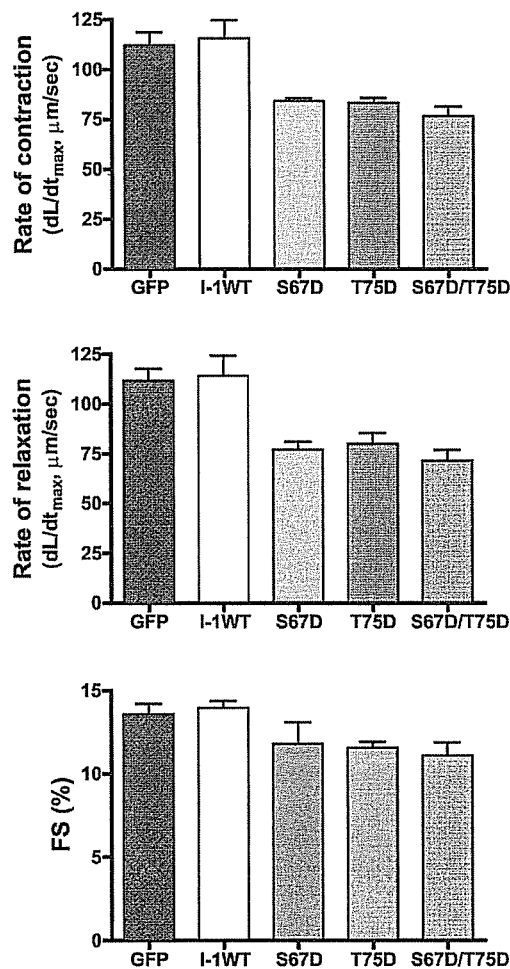
FIG. 15. Effect of PKA activation on myocytes infected with Ad.I-1(S67D), Ad.I-1(T75D) and Ad.I-1(S67D/T75D)—Fractional shortening (FS %) and maximal rates of contraction and relaxation ($dL/dt_{max}$, µm/sec) of infected-cardiomyocytes treated with 0.1 µM forskolin are shown in bar graph form.

To assess whether stimulation of the cAMP-dependent kinase pathway is capable of reversing the depressed function of myocytes expressing constitutively phosphorylated I-1 mutants, adenoviruses infected cardiomyocytes were treated with a range of forskolin concentrations from 10 nM to 1 µM. Surprisingly, high doses of forskolin elicited arrhythmias only in myocytes expressing the constitutively phosphorylation sites (Ser-67 and/or Thr-75) but not I-1 WT or GFP. Therefore, 0.1 µM was established as the highest concentration that induced stimulation of contractility without eliciting arrhythmias. Forskolin treatment of myocytes expressing Ad.GFP caused dramatic increases in the velocities of contraction (38%) and relaxation (51%), as well as in fractional shortening (8.5%), compare to the basal levels (FIG. 15). The total number of hearts was as follows: 10 (Ad.GFP), 5 (Ad.I-1 WT), 5 (Ad.I-1(S67D)), 6 (Ad.I-1(T75D)), and 6 (Ad.I-1 (S67D/T75D)), with 15-20 myocytes/heart.

The increases in performance in cells expressing Ad.I-1WT were similar to the control cells (36.5%, 49% and 15.5% for the velocities of contraction and relaxation, respectively, and fractional shortening). Importantly, cardiac function of myocytes infected with Ad.I-1(S67D), Ad.I-1(T75D) or Ad.I-1(S67D/T75D) also improved upon drug treatment, but the cardiac parameters did not reach the maximal effect observed either in the Ad.I-1WT or Ad.GFP (FIG. 15). Of note, the percent increases in the rates of contraction upon forskolin for the constitutively phosphorylated I-1 infected myocytes, approximated the percent increases found for the Ad.GFP and Ad.I-1WT infections, indicating no alterations in the PKA-signaling pathway. Thus, although cardiac contractility of myocytes expressing the phosphorylated I-1 mutants can be improved by similar increments as I-1WT and GFP infected cells upon forskolin treatment, the overall function remains depressed in comparison to the control cells.

Example 7

Sarcoplasmic Reticulum $Ca^{2+}$ Uptake in Adenoviral-Infected Cardiomyocytes

Figure 16A:
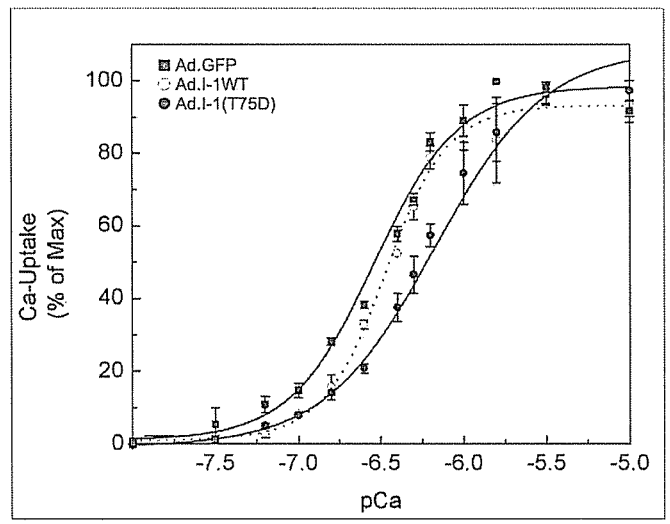
FIG. 16. Effect of phosphorylation of I-1 at Thr-75 on the $Ca^{2+}$ affinity of SR $Ca^{2+}$-transport—(A) Plot depicting the initial rates of SR $Ca^{2+}$-transport over a wide range of $[Ca^{2+}]$ measured for I-1 wild-type, I-1(T75D) and GFP proteins expressed in cultured cardiomyocytes. The data were normalized to the calculated $V_{max}$ for Ad.I-1WT, Ad.I-1(T75D) and Ad.GFP samples. Curves represent sigmoidal fit obtained by the OriginLab 5.1 program. Symbols represent the average of three individual homogenized myocytes infected with Ad.GFP (solid squares), Ad.I-1WT (empty circles) and Ad.I-1(T75D) (solid circles), assayed per duplicate. (B) Immunoblot depicting total SERCA2a (Affinity Bioreagents, 1:1000), total PLN, and calsequestrin (as an internal loading control (Affinity Bioreagents; 1:1000)).
Figure 16B:
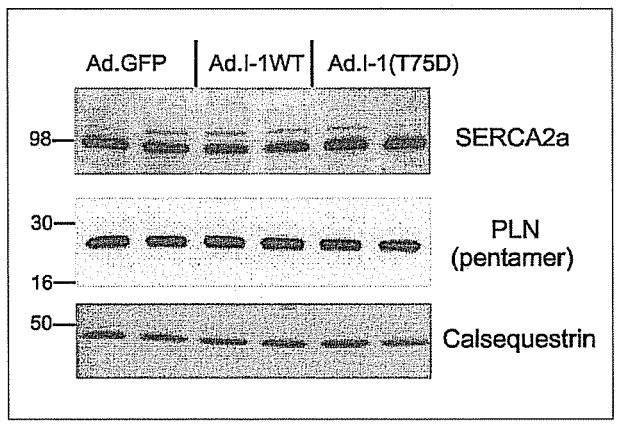

To determine whether the depressed contractility associated with phosphorylation of I-1 at Thr-75 corresponded to alterations in the sarcoplasmic reticulum calcium transport function, the initial rates of $Ca^{2+}$ transport were assessed over a wide range of $[Ca^{2+}]$, similar to those present in vivo during relaxation and contraction. The reaction conditions were as follows: 37° C. using 5 mM ATP in 40 mM Imidazole (pH=7.0), 95 mM KCl, 5 mM $NaN_3$, 5 mM $MgCl_2$, 0.5 mM EGTA, and 5 mM $K_2C_2O_4$. The apparent affinity of the transport system for $Ca^{2+}$ decreased significantly in myocytes infected with the Ad.I-1 (T75D) ($EC_{50}$ value=0.67±0.01 µM; n=3; ***p<0.001), compared to either Ad.I-1WT (0.33±0.01 µM; n=3) or Ad.GFP (0.28±0.006 µM; n=3) (FIG. 16A). However, the $V_{max}$ of $Ca^{2+}$ uptake was similar among all the three groups. Furthermore, there were no differences in the sarcoplasmic calcium pump (SERCA2a) and phospholamban (PLN) protein levels in these groups (FIG. 16B). These data indicate that phosphorylation of I-1 by PKC-α at Thr-75, may elicit depressed cardiac contractility by reducing the $Ca^{2+}$ affinity of SERCA2a.

Figure 17A:
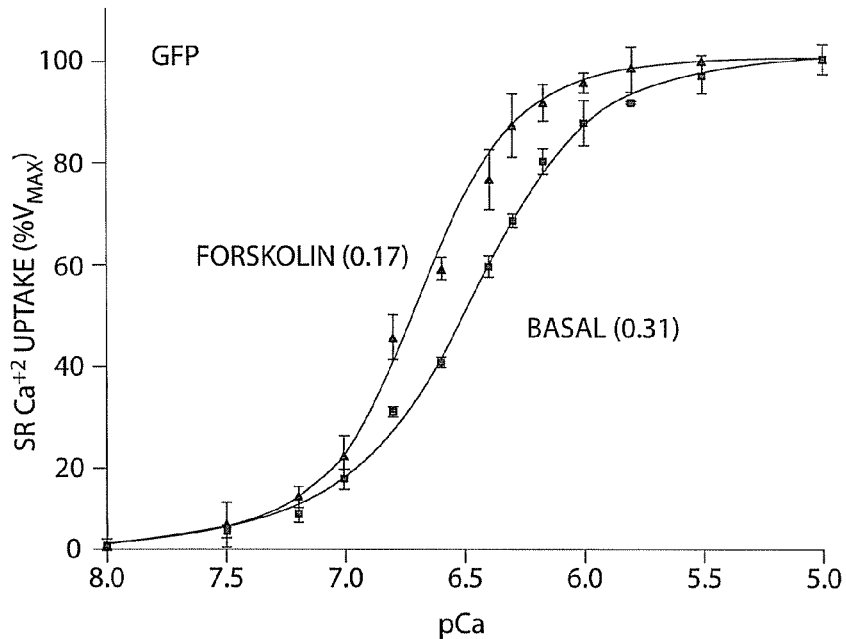
FIG. 17. Effect of phosphorylation of inhibitor-1 at Ser-67 and/or Thr-75 on the $Ca^{2+}$ affinity of SR $Ca^{2+}$-transport—plots showing results of assessment of the initial rates of SERCA $Ca^{2+}$-transport in cardiomyocytes infected with: (A) Ad.GFP; (B) Ad.I-1WT; (C) Ad.I-1(S67D); (D) Ad.I-1 (T75D); and (E) Ad.I-1(S67D/T75D). Symbols represent the average of three homogenized myocytes from individual hearts under basal or forskolin treatment, assayed per duplicate. (F) Graph showing the $EC_{50}$ average values under basal and forskolin treatment for each group. ***, p<0.001 represents comparison of each group vs. GFP, under basal. #, p<0.05; ##, p<0.01, represent comparison of each group vs. GFP, under forskolin.
Figure 17B:
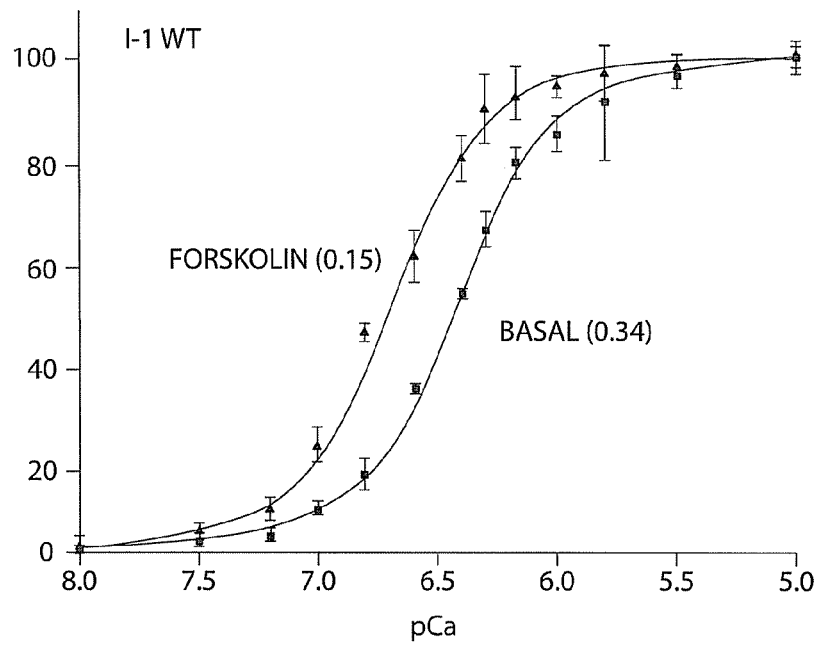
Figure 17C:
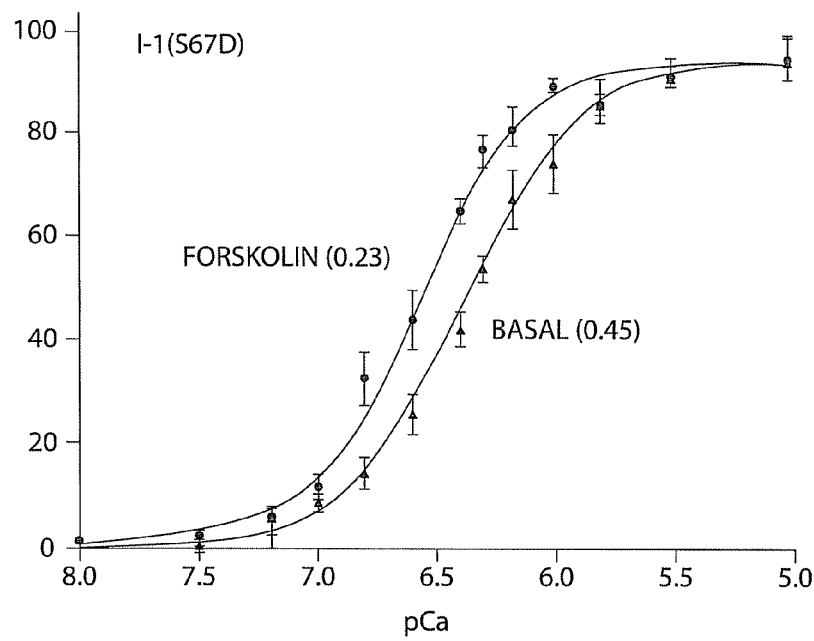
Figure 17D:
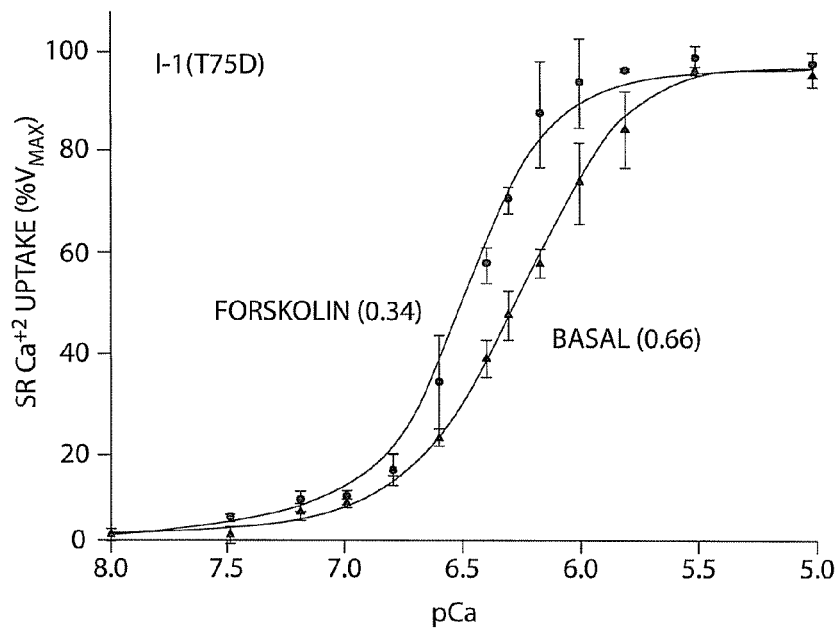
Figure 17E:
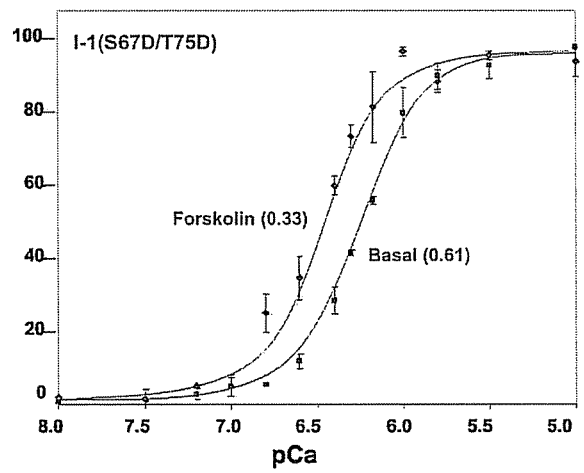
Figure 17F:
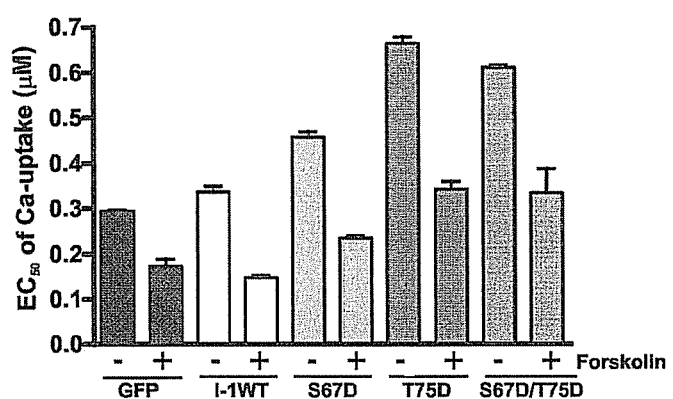

The basal SR $Ca^{2+}$ uptake rates were assessed in homogenates generated from myocytes infected with adenoviruses expressing GFP, as a control, and the I-1 species: I-1WT, I-1(S67D), I-1(T75D) or I-1(S67D/T75D), under conditions which restrict Ca-uptake to SR. Consistent with a recent study [10], infection with an adenovirus expressing GFP or wild-type I-1 exhibited similar SERCA $EC_{50}$ values (0.294±0.001 µM and 0.336±0.013 µM, respectively) (FIGS. 17A and 17C). However, the apparent affinity of SERCA for calcium was significantly lower in myocytes expressing the I-1 (S67D), I-1(T75D) and I-1(S67D/T75D) mutants (0.457±0.012 µM, 0.664±0.014 µM and 0.611±0.005 µM, respectively) (FIGS. 17A and 17C). The data shown in FIG. 17 were normalized to the calculated $V_{max}$ for each group, and fit to a sigmoidal curve by using OriginLab 5.1 program.

It has, thus, been shown that phosphorylation of Ser-67 and/or Thr-75 on the human I-1 isoform mitigates the effects of subsequent PKA stimulation in cardiomyocytes. Phosphorylation of either or both sites simultaneously decrease the ability of I-1 to fully inhibit PP1 activity following PKA activation, resulting in an overall impaired SERCA 2a transport function and cardiac contractility.

As expected, PKA stimulation by forskolin was associated with a significant decrease in the SR $Ca^{+2}$-uptake $EC_{50}$ for $Ca^{+2}$ in myocytes expressing GFP ($EC_{50}$=0.17±0.029 µM), and this decrease was similar to that observed in cardiomyocytes expressing wild-type I-1 ($EC_{50}$=0.147±0.005 µM). (FIGS. 17B and 17C). However, although forskolin treatment of cardiomyocytes expressing the constitutively phosphorylated I-1 mutants was capable of improving $EC_{50}$ values from their respective basal values, the calcium uptake rates remained depressed compare to the I-1WT and GFP infected cells. The $EC_{50}$ values for cardiomyocytes expressing I-1 (S67D), I-1(T75D) and I-1(S67D/T75D) following forskolin treatment were: 0.234±0.005 µM, 0.342±0.016 µM, and 0.334±0.053 µM, respectively (FIGS. 17A and 17C).

Thus, the consequences of constitutive phosphorylation of I-1 at Ser-67 and/or Thr-75 were associated with depressed SR calcium uptake rates and cardiomyocyte function. Depressed SR calcium uptake rates were reflective of significantly higher SERCA $EC_{50}$ values under both basal and forskolin stimulated conditions. Although PKA activation by Forskolin did not improve the $Ca^{2+}$-ATPase function in myocytes expressing phosphorylated Ser-67 and/or Thr-75 I-1 to the same extent than myocytes expressing I-1WT or GFP, the percentage decreases of the $EC_{50}$ values appeared similar in all the groups, indicating that the PKA-signaling pathway is not altered.

Since calcium uptake into the SR represents a nodal point at which cardiomyocyte contractility is regulated, the mechanical performance of the cardiomyocytes infected with phosphorylated Ser-67 and/or Thr75 I-1 mirrored SR calcium uptake measurements. Phosphorylation of I-1 at either Ser-67 and/or Thr-75 elicited significant depression of SERCA transport function, and these values remained depressed even after forskolin treatment. Indeed, stimulation of PKA in these groups of infected myocytes only improved SR $Ca^{+2}$ uptake values to the basal levels of the I-1WT group. These findings indicate that the effects of PKA are blunted in cardiomyocytes by the constitutively phosphorylated mutants at either Ser-67 or Thr-75. Similar values for the maximum velocity ($V_{max}$) of $Ca^{+2}$ uptake were obtained in all samples.

Example 8

Protein Phosphatase Activity in Infected Cardiomyocytes

Figure 18A:
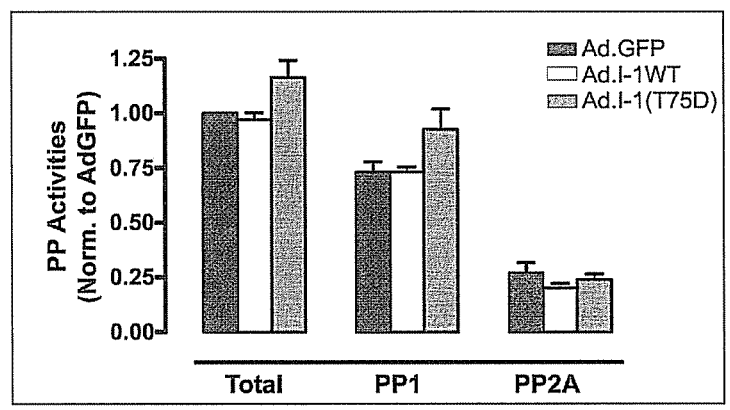
FIG. 18. PKC-α phosphorylation of I-1 at Thr-75 enhances PP1 activity—(A) Bar graph depicting total phosphatase activity assayed in cardiomyocyte lysates (1 µg) infected with Ad.GFP (solid bar), Ad.I-1WT (open bar) or Ad.I-1(T75D) (grey bar). Okadaic acid (10 nM) was added to cell lysates to differentiate type 1 and 2A phosphatase activities. Quantified values represent the average of 4 independent cell lysates assayed in duplicate and normalized to Ad.GFP (mean±SEM). (B) Bar graph depicting PP1c (0.5 ng) activity measured for purified recombinant I-1 wild-type (solid bar), PKC-α-phosphorylated I-1(S67A) (open bar) and I-1(T75D) (grey bar). Values are normalized to I-1 wild-type. Error bars indicate SEM values for 5 independent experiments, each per duplicate.

The decreases in cardiomyocyte contractility and the apparent affinity of the SR $Ca^{2+}$-transport system for $Ca^{2+}$ prompted investigation of the protein phosphatase activity levels in adult rat cardiomyocytes infected with Ad.I-1WT, Ad.I-1(T75D), and Ad.GFP. Total phosphatase activity was assayed in cardiomyocyte lysates (1 µg) infected with Ad.GFP, Ad.I-1 WT, or Ad.I-1(T75D). The reaction mixture contained 50 mM Tris-HCl (pH 7.0), 0.1 mM $Na_2EDTA$, 5 mM DTT, 0.01% Brij35, and radiolabeled Myelin Basic Protein (50 µM). Total phosphatase activity was increased by 16% in myocytes expressing I-1(T75D), compared to cells expressing I-1 wild-type or control cells (FIG. 18A). The relative contribution of the two major classes of cellular protein phosphatases, PP1 and PP2A, was determined in the presence of okadaic acid at a concentration (10 nM) which inhibits PP2A more potently (Neumann et al. *J. Mol Cell. Cardiol* (1997)). Cardiomyocytes infected with Ad.I-1 (T75D) showed a 27% increase in type-1 phosphatase activity compared to Ad.I-1WT and Ad.GFP, whereas there was no change in the type-2A phosphatase activity (FIG. 18A). As shown in FIG. 13B, the protein levels of PP1 were the same in all cases.

Figure 18B:
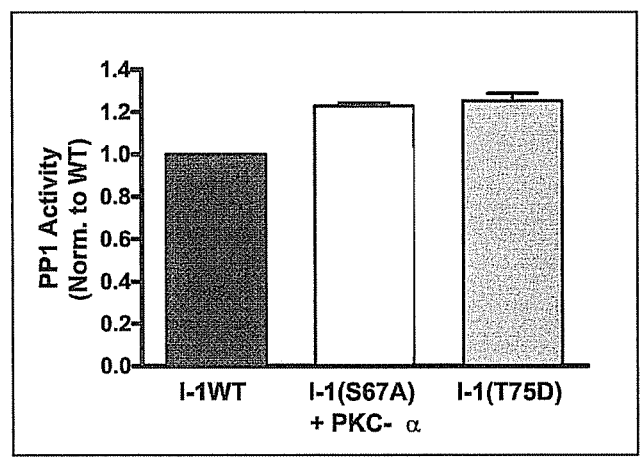

The effects of I-1 phosphorylation at Thr-75 on type-1 phosphatase activity were further confirmed by measuring the activity of the purified PP1 catalytic subunit (PP1c) in the presence of recombinant I-1 wild-type, or I-1 with either constitutively phosphorylated I-1, I-1(T75D), or I-1(S67A) pre-phosphorylated by PKC-α. Both mutant I-1 proteins significantly increased PP1c activity by 23% and 25%, respectively, compared to I-1 wild-type (FIG. 18B). Taken together, these data demonstrate that phosphorylation of I-1 at Thr-75 by PKC-α increases PP1 activity in both isolated myocytes and in vitro systems.

Figure 19:
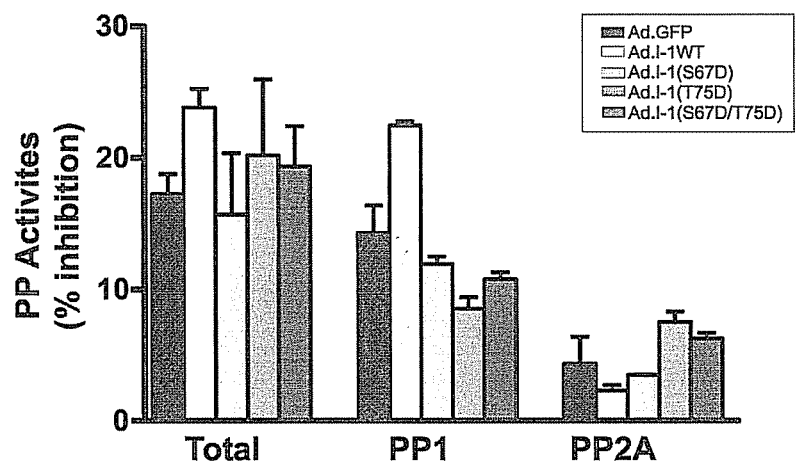
FIG. 19. Percentage of inhibition of protein phosphatase-1 activity in adenoviral infected myocytes upon PKA stimulation—Bar graph showing total phosphatase activity assayed in forskolin-treated myocyte lysates overexpressing: Ad.GFP (black bar); Ad.I-1WT (white bar); Ad.I-1(S67D) (light grey bar); Ad.I-1(T75D) (medium grey bar); and Ad.I-1(S67D/T75D) (dark grey bar). Bars represent the average of 3 independent myocytes lysates assayed per duplicate (mean±SEM).

After PKA stimulation by forskolin, although the percentage of total protein phosphatase inhibition appeared to be similar in all the groups (FIG. 19), selective PP1 inhibition, as assessed by using 10 nM Okadaic acid as a PP2A inhibitor (Rodriguez et al. *J. Biol. Chem.* (2006) Neumann et al. *J. Mol Cell Cardiol.* (1997)), by myocytes expressing Ad.I-1WT was significant higher upon forskolin treatment compared to cells infected with Ad.GFP. Okadaic acid (10 nM) was added to cell lysates to differentiate type 1 and 2A phosphatase activities. The results indicate that the levels of endogenous I-1 may not be sufficiently high to fully inhibit PP1 activity. In contrast, the three constitutively phosphorylated I-1 mutants, I-1(S67D), I-1(T75D) and I-1(S67D/T75D), presented significantly less inhibition of PP1 under forskolin, compared to either control or wild-type infected cells. Thus, constitutive phosphorylation of either Ser-67 or Thr-75 reduced the extent to which PP1 became inhibited, following PKA stimulation in cardiomyocytes.

These two sites appeared equivalent in eliciting this effect, and no additive effect was observed when both sites were phosphorylated. Indeed, constitutive phosphorylation of both or either of these sites caused PP1 activity to remain ~2-fold higher following PKA stimulation. These data indicate that, in the failing heart, attenuated β-adrenergic signaling and increased PKC signaling would serve as a double insult, favoring higher PP1 activity. The percentage of PP1 inhibition in myocytes expressing the I-1 double mutant (S67D/T75D) was similar to that exhibited by either S67D or T75D I-1 mutants, indicating that simultaneous phosphorylation of the two sites did not exhibit an additive effect in the inhibition of PP1 activity after PKA stimulation.

Example 9

Figure 20A:
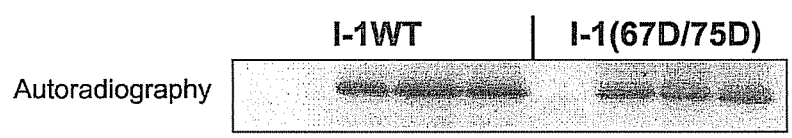
Figure 20B:
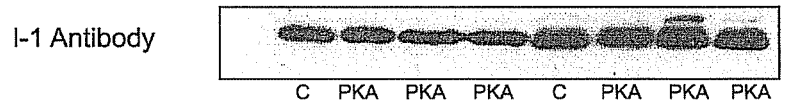
Figure 20C:
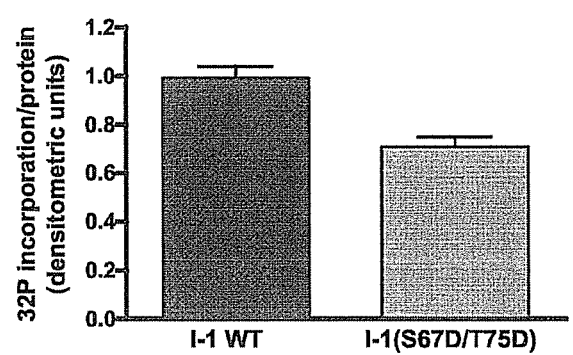

Effect of Phosphorylation of I-1 at Ser-67 and Thr-75 Upon its Ability to be a Substrate for PKA To analyze whether phosphorylation of I-1 at both Ser-67 and Thr-75 reduces the ability of PKA phosphorylation of I-1 at Thr-35, recombinant I-1 wild-type and I-1(S67D/T75D) proteins were incubated in vitro with PKA in the presence of [γ-$^{32}$P] ATP. As shown in FIG. 20, the double mutant incorporated 29% less radioactivity than the wild-type, indicating that Thr-35 can not be phosphorylated to the same extent in the mutant. Thus, the ability of I-1 to be phosphorylated by PKA is likely altered when both Ser-67 and Thr-75 are previously phosphorylated.

Taken together, the data described herein indicate that, in the heart, phosphorylation of Ser-67 and/or Thr-75 on the human I-1 isoform may work to partially suppress β-adrenergic signaling and, consequently, reduce the stimulatory effects on contractility through the maintenance of an abnormally enhance PP1 activity.

Example 10

Codon-Optimized Truncated I-1

The wild-type I-1 gene was found to use rare codons with a high frequency and to contain several negatively cis-acting motifs, which might hamper expression in animals. Thus, standard codon optimization (based on the human codon usage table, below, as published on http://bip.weizmann.ac.il/index.html and described, for example, in "Genetic Databases", M. J. Bishop ed., Academic Press, (1999) was employed to synthesize a truncated mutant human I-1 protein (T35D) encoded by SEQ ID NO: 13, below. The truncation of the I-1 cDNA is to encode the first 65 amino acids of the protein.

The codon usage was adapted to the codon bias of *Homo sapiens* genes, resulting in a high codon adaptation index (CAI) value (0.99). The codon-optimized (truncated) protein has an increased GC content (relative to the native human sequence) for more efficient AAV packaging (data not shown). Certain cis-acting sequence motifs were avoided (for example, splice sites, polyA signals). Kozak sequence was introduced to increase translational initiation. Two STOP codons were added to ensure efficient termination.

The Human Codon Usage Table

| | | | | | | | | | | | | | | | | |
|---|---|---|---|---|---|---|---|---|---|---|---|---|---|---|---|---|
| Gly | GGG | 17.08 | 0.23 | Arg | AGG | 12.09 | 0.22 | Trp | TGG | 14.74 | 1.00 | Arg | CGG | 10.40 | 0.19 |
| Gly | GGA | 19.31 | 0.26 | Arg | AGA | 11.73 | 0.21 | End | TGA | 2.64 | 0.61 | Arg | CGA | 5.63 | 0.10 |
| Gly | GGT | 13.66 | 0.18 | Ser | AGT | 10.18 | 0.14 | Cys | TGT | 9.99 | 0.42 | Arg | CGT | 5.16 | 0.09 |
| Gly | GGC | 24.94 | 0.33 | Ser | AGC | 18.54 | 0.25 | Cys | TGC | 13.86 | 0.58 | Arg | CGC | 10.82 | 0.19 |
| Glu | GAG | 38.82 | 0.59 | Lys | AAG | 33.79 | 0.60 | End | TAG | 0.73 | 0.17 | Gln | CAG | 32.95 | 0.73 |
| Glu | GAA | 27.51 | 0.41 | Lys | AAA | 22.32 | 0.40 | End | TAA | 0.95 | 0.22 | Gln | CAA | 11.94 | 0.27 |
| Asp | GAT | 21.45 | 0.44 | Asn | AAT | 16.43 | 0.44 | Tyr | TAT | 11.80 | 0.42 | His | CAT | 9.56 | 0.41 |
| Asp | GAC | 27.06 | 0.56 | Asn | AAC | 21.30 | 0.56 | Tyr | TAC | 16.48 | 0.58 | His | CAC | 14.00 | 0.59 |
| Val | GTG | 28.60 | 0.48 | Met | ATG | 21.86 | 1.00 | Leu | TTG | 11.43 | 0.12 | Leu | CTG | 39.93 | 0.43 |
| Val | GTA | 6.09 | 0.10 | Ile | ATA | 6.05 | 0.14 | Leu | TTA | 5.55 | 0.06 | Leu | CTA | 6.42 | 0.07 |
| Val | GTT | 10.30 | 0.17 | Ile | ATT | 15.03 | 0.35 | Phe | TTT | 15.36 | 0.43 | Leu | CTT | 11.24 | 0.12 |
| Val | GTC | 15.01 | 0.25 | Ile | ATC | 22.47 | 0.52 | Phe | TTC | 20.72 | 0.57 | Leu | CTC | 19.14 | 0.20 |
| Ala | GCG | 7.27 | 0.10 | Thr | ACG | 6.80 | 0.12 | Ser | TCG | 4.38 | 0.06 | Pro | CCG | 7.02 | 0.11 |

The Human Codon Usage Table

| Ala | GCA | 15.50 | 0.22 | Thr | ACA | 15.04 | 0.27 | Ser | TCA | 10.96 | 0.15 | Pro | CCA | 17.11 | 0.27 |
| --- | --- | --- | --- | --- | --- | --- | --- | --- | --- | --- | --- | --- | --- | --- | --- |
| Ala | GCT | 20.23 | 0.28 | Thr | ACT | 13.24 | 0.23 | Ser | TCT | 13.51 | 0.18 | Pro | CCT | 18.03 | 0.29 |
| Ala | GCC | 28.43 | 0.40 | Thr | ACC | 21.52 | 0.38 | Ser | TCC | 17.37 | 0.23 | Pro | CCC | 20.51 | 0.33 |

For each codon, the table displays the frequency of usage of each codon (per thousand) in human coding regions (first column) and the relative frequency of each codon among synonymous codons (second column).

SEQ ID NO: 13 reads as follows:

```
GGGCGAATTGGGTACCGCCACCATGGAACAGGACAACAGCCCCCGGAAGATCCAGTTCACCGTGCCCC

TGCTGGAACCCCACCTGGACCCCGAGGCCGCCGAGCAGATCCGGCGGAGAAGGCCCGACCCCGCCACC

CTGGTGCTGACCAGCGACCAGAGCAGCCCCGAGATCGACGAGGACCGGATCCCCAACCCCCACCTGAA

GAGCACCCTGGCCTGATGAGACCTCCAGCTTTTGTTCCC
```

The amino acid sequence encoded by SEQ ID NO: 13 is set forth as SEQ ID NO: 14, as follows:

```
MEQDNSPRKIQFTVPLLEPHLDPEAAEQIRRRRPDPATLVLTSDQSSPE

IDEDRIPNPHLKSTLA
```

The amino acid sequence encoded by SEQ ID NO: 13 is set forth as SEQ ID NO: 14.

Codon optimization for I-1 mutants described herein is likewise contemplated.

Sequence Information

It should be understood that for purposes of describing, defining, and claiming the present invention, reference to a "SEQ ID NO:" is taken to include all sequences having at least 90 percent identity therewith and retaining any specified mutation. In more specific embodiments, it is understood to include sequences having at least 95% identity therewith and retaining any specified mutation. In yet more specific embodiments, it includes sequences having between 99% and 100% identity therewith and retaining any specified mutation.

The wild type sequence for *Homo Sapiens* Protein Phosphatase I, inhibitor subunit 1A, (PP1I1A) mRNA, is set forth below (SEQ ID NO:7). Nucleotide changes for mutants occur between positions 361 and 400, according to this numbering scheme based on the cDNA. The first A in the coding sequence could be indicated as 1 (rather than 172).

```
  1 AGTGTCCCCG GAGCCGCGAG CTGGGAGCGC TGTGCCGGGA GCCGGGAGCC GAGCGCGCCG
 61 GGCTGGGGCC GGGGCCGGAG CGGAGCGGAG AGGGAGCGCG CCCGCCCCAG CCCCGAGTCC
121 CGCCGCCTTC CCTCCCGCCG CAGCGCGGGC CCACCGGCCG CCGCCCAGC CATGGAGCAA
181 GACAACAGCC CCCAAAAGAT CCAGTTCACG GTCCCGCTGC TGGAGCCGCA CCTTGACCCC
241 GAGGCGGCGG AGCAGATTCG GAGGCGCCGC CCCACCCCTG CCACCCTCGT GCTGACCAGT
301 GACCAGTCAT CCCCAGAGAT AGATGAAGAC CGGATCCCCA ACCCACATCT CAAGTCCACT
361 TTGGCAATGT CTCCACGGCA ACGGAAGAAG ATGACAAGGA TCACACCCAC AATGAAAGAG
421 CTCCAGATGA TGGTTGAACA TCACCTGGGG CAACAGCAGC AAGGAGAGGA ACCTGAGGGG
481 GCCGCTGAGA GCACAGGAAC CCAGGAGTCC CGCCCACCTG GGATCCCAGA CACAGAAGTG
541 GAGTCAAGGC TGGGCACCTC TGGGACAGCA AAAAAAACTG CAGAATGCAT CCCTAAAACT
601 CACGAAAGAG GCAGTAAGGA ACCCAGCACA AAAGAACCCT CAACCCATAT ACCACCACTG
661 GATTCCAAGG GAGCCAACTC GGTCTGAGAG AGGAGGAGGT ATCTTGGGAT CAAGACTGCA
```

The amino acid sequence encoded by SEQ ID NO: 7 is set forth as SEQ ID NO: 8, as follows:

```
  1 MEQDNSPQKIQFTVPLLEPHLDPEAAEQIRRRRPTPATLVLTSDQSSPEI
 51 DEDRIPNPHLKSTLAMSPRQRKKMTRITPTIMKELQMMVEHHLGQQQ
101 QGEEPEGAAESTGTQESRPPGIPDTEVESRLGTSGTAKKTAECIPKTHER
151 GSKEPSTKEPSTHIPPLDSKGANSV
```

Amino acid positions 35, 67, and 75 have been highlighted with bold font and underlining.

It is understood that the human wild type PP-1 exists as polymorphs, known and possibly unknown. For example, there are two polymorphs based on amino acid position 8, which may comprise either an asparagine or lysine residue. The former is known in the art as the Q variant, while the latter is known in the art as the K variant. As mentioned in the "Definitions" section, above, it will be apparent to one of ordinary skill in the art that either variant is suitable, and the variants are essentially interchangeable, for purposes of practicing and defining the present invention. It will be equally apparent that other such polymorphs may exist and are equally intended to fall within the scope of the present invention.

It should be noted that nucleotide position 172 of SEQ ID NO: 7, above, equals position 1, for the purposes of describing the sequences herein. The relevant coding sequence ends at position 688. The location of the codon corresponding to amino acid position 67 of the polypeptide encoded by the nucleotide sequence defined by positions 172-688, above, according to the present invention, is: positions 371, 372, 373, (TCT), and the location for the codon corresponding to amino acid position 75, similarly, is 394, 395, 396 (ACA).

The mutant "I-1 S67A" has the codon TCT replaced by GCA and is set forth as SEQ ID NO: 1. The mutant "I-1 S67D" has the codon TCT replaced by GAC and is set forth as SEQ ID NO: 2. The mutant "I-1 T75D" has the codon ACA replaced by GAC and is set forth as SEQ ID NO: 3. The mutant "I-1 T75A" has the codon ACA replaced by GCA and is set forth as SEQ ID NO: 4.

The amino acid sequence encoded by SEQ ID NO: 3 is set forth as SEQ ID NO: 5. The amino acid sequence encoded by SEQ ID NO: 4 is set forth as SEQ ID NO: 6. The amino acid sequence encoded by SEQ ID NO: 7 is set forth as SEQ ID NO: 8.

The mutant "I-1 S67C" has the codon TCT replaced by the codon TGT or TGC and is set forth as SEQ ID NO: 9. The mutant "I-1 T75C" has the codon ACA replaced by the codon TGT or TGC and is set forth as SEQ ID NO: 10. The amino acid sequence encoded by SEQ ID NO: 9 is set forth as SEQ ID NO: 11. The amino acid sequence encoded by SEQ ID NO: 10 is set forth as SEQ ID NO: 12.

It is also contemplated that a single nucleic acid molecule may comprise mutations at both locations. The mutant "I-1 S67A/T75A" has codon 67 (TCT) related by GCA and codon 75 (ACA) replaced by GCA and is set forth in SEQ ID NO: 15. The amino acid sequence encoded by SEQ ID NO: 15 is set forth as SEQ ID NO: 16. The mutant "I-1 S67D/T75D" has codon 67 (TCT) replaced by GAC and codon 75 (ACA) replaced by GAC and is set forth in SEQ ID NO: 17. The amino acid sequence encoded by SEQ ID NO: 17 is set forth as SEQ ID NO: 18.

The mutant "I-1 T35D" has the codon ACC replaced by the codon GAC and is set forth in SEQ ID NO: 19.

The amino acid sequence encoded by SEQ ID NO: 19 is set forth as SEQ ID NO: 20. The mutant "I-1 S67A/T35D" has the codon TCT (371-373) replaced by GCA and the codon ACC (277-279) replaced by GAC and is set forth in SEQ ID NO: 22. The amino acid sequence encoded by SEQ ID NO: 22 is set forth as SEQ ID NO: 21.

SEQ ID NO: 1:

```
                                                                  ATGGAGCAA
181 GACAACAGCC CCCAAAAGAT CCAGTTCACG GTCCCGCTGC TGGAGCCGCA CCTTGACCCC
241 GAGGCGGCGG AGCAGATTCG GAGGCGCCGC CCCACCCCTG CCACCCTCGT GCTGACCAGT
301 GACCAGTCAT CCCCAGAGAT AGATGAAGAC CGGATCCCCA ACCCACATCT CAAGTCCACT
361 TTGGCAATGG CACCACGGCA ACGGAAGAAG ATGACAAGGA TCACACCCAC AATGAAAGAG
421 CTCCAGATGA TGGTTGAACA TCACCTGGGG CAACAGCAGC AAGGAGAGGA ACCTGAGGGG
481 GCCGCTGAGA GCACAGGAAC CCAGGAGTCC CGCCCACCTG GGATCCCAGA CACAGAAGTG
541 GAGTCAAGGC TGGGCACCTC TGGGACAGCA AAAAAAACTG CAGAATGCAT CCCTAAAAGT
601 CACGAAAGAG GCAGTAAGGA ACCCAGCACA AAAGAACCCT CAACCCATAT ACCACCACTG
661 GATTCCAAGG GAGCCAACTC GGTCTGA
```

SEQ ID NO: 2:

```
                                                                  ATGGAGCAA
181 GACAACAGCC CCCAAAAGAT CCAGTTCACG GTCCCGCTGC TGGAGCCGCA CCTTGACCCC
241 GAGGCGGCGG AGCAGATTCG GAGGCGCCGC CCCACCCCTG CCACCCTCGT GCTGACCAGT
301 GACCAGTCAT CCCCAGAGAT AGATGAAGAC CGGATCCCCA ACCCACATCT CAAGTCCACT
361 TTGGCAATGG ACCCACGGCA ACGGAAGAAG ATGACAAGGA TCACACCCAC AATGAAAGAG
421 CTCCAGATGA TGGTTGAACA TCACCTGGGG CAACAGCAGC AAGGAGAGGA ACCTGAGGGG
481 GCCGCTGAGA GCACAGGAAC CCAGGAGTCC CGCCCACCTG GGATCCCAGA CACAGAAGTG
541 GAGTCAAGGC TGGGCACCTC TGGGACAGCA AAAAAAACTG CAGAATGCAT CCCTAAAACT
601 CACGAAAGAG GCAGTAAGGA ACCCAGCACA AAAGAACCCT CAACCCATAT ACCACCACTG
661 GATTCCAAGG GAGCCAACTC GGTCTGA
```

SEQ ID NO: 3:

```
                                                                  ATGGAGCAA
181 GACAACAGCC CCCAAAAGAT CCAGTTCACG GTCCCGCTGC TGGAGCCGCA CCTTGACCCC
241 GAGGCGGCGG AGCAGATTCG GAGGCGCCGC CCCACCCCTG CCACCCTCGT GCTGACCAGT
301 GACCAGTCAT CCCCAGAGAT AGATGAAGAC CGGATCCCCA ACCCACATCT CAAGTCCACT
361 TTGGCAATGT CTCCACGGCA ACGGAAGAAG ATGGACAGGA TCACACCCAC AATGAAAGAG
421 CTCCAGATGA TGGTTGAACA TCACCTGGGG CAACAGCAGC AAGGAGAGGA ACCTGAGGGG
481 GCCGCTGAGA GCACAGGAAC CCAGGAGTCC CGCCCACCTG GGATCCCAGA CACAGAAGTG
541 GAGTCAAGGC TGGGCACCTC TGGGACAGCA AAAAAAACTG CAGAATGCAT CCCTAAAACT
601 CACGAAAGAG GCAGTAAGGA ACCCAGCACA AAAGAACCCT CAACCCATAT ACCACCACTG
661 GATTCCAAGG GAGCCAACTC GGTCTGA
```

SEQ ID NO: 4:

```
                                                                  ATGGAGCAA
181 GACAACAGCC CCCAAAAGAT CCAGTTCACG GTCCCGCTGC TGGAGCCGCA CCTTGACCCC
241 GAGGCGGCGG AGCAGATTCG GAGGCGCCGC CCCACCCCTG CCACCCTCGT GCTGACCAGT
301 GACCAGTCAT CCCCAGAGAT AGATGAAGAC CGGATCCCCA ACCCACATCT CAAGTCCACT
361 TTGGCAATGT CTCCACGGCA ACGGAAGAAG ATGGCAAGGA TCACACCCAC AATGAAAGAG
421 CTCCAGATGA TGGTTGAACA TCACCTGGGG CAACAGCAGC AAGGAGAGGA ACCTGAGGGG
481 GCCGCTGAGA GCACAGGAAC CCAGGAGTCC CGCCCACCTG GGATCCCAGA CACAGAAGTG
541 GAGTCAAGGC TGGGCACCTC TGGGACAGCA AAAAAAACTG CAGAATGCAT CCCTAAAACT
```

-continued

601 CACGAAAGAG GCAGTAAGGA ACCCAGCACA AAAGAACCCT CAACCCATAT ACCACCACTG

661 GATTCCAAGG GAGCCAACTC GGTCTGA

SEQ ID NO: 5:
  1 MEQDNSPQKIQFTVPLLEPHLDPEAAEQIRRRRPTPATLVLTSDQSSPEI

51 DEDRIPNPHLKSTLAMSPRQRKKMDRITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 6:
  1 MEQDNSPQKIQFTVPLLEPHLDPEAAEQIRRRRPTPATLVLTSDQSSPEI

51 DEDRIPNPHLKSTLAMSPRQRKKMARITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 9:
                                                    ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCCACCCCTG CCACCCTCGT GCTGACCAGT

301 GACCAGTCAT CCCCAGAGAT AGATGAAGAC CGGATCCCCA ACCCACATCT CAAGTCCACT

361 TTGGCAATGT G(T/C)CCACGGCA ACGGAAGAAG ATGACAAGGA TCACACCCAC AATGAAAGAG

421 CTCCAGATGA TGGTTGAACA TCACCTGGGG CAACAGCAGC AAGGAGAGGA ACCTGAGGGG

481 GCCGCTGAGA GCACAGGAAC CCAGGAGTCC CGCCCACCTG GGATCCCAGA CACAGAAGTG

541 GAGTCAAGGC TGGGCACCTC TGGGACAGCA AAAAAAACTG CAGAATGCAT CCCTAAAACT

601 CACGAAAGAG GCAGTAAGGA ACCCAGCACA AAAGAACCCT CAACCCATAT ACCACCACTG

661 GATTCCAAGG GAGCCAACTC GGTCTGA

SEQ ID NO: 10:
                                                    ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCCACCCCTG CCACCCTCGT GCTGACCAGT

301 GACCAGTCAT CCCCAGAGAT AGATGAAGAC CGGATCCCCA ACCCACATCT CAAGTCCACT

361 TTGGCAATGT CTCCACGGCA ACGGAAGAAG ATGTG(T/C)AGGA TCACACCCAC AATGAAAGAG

421 CTCCAGATGA TGGTTGAACA TCACCTGGGG CAACAGCAGC AAGGAGAGGA ACCTGAGGGG

481 GCCGCTGAGA GCACAGGAAC CCAGGAGTCC CGCCCACCTG GGATCCCAGA CACAGAAGTG

541 GAGTCAAGGC TGGGCACCTC TGGGACAGCA AAAAAAACTG CAGAATGCAT CCCTAAAACT

601 CACGAAAGAG GCAGTAAGGA ACCCAGCACA AAAGAACCCT CAACCCATAT ACCACCACTG

661 GATTCCAAGG GAGCCAACTC GGTCTGA

SEQ ID NO: 11:
  1 MEQDNSPQKIQFTVPLLEPHLDPEAAEQTRRRRPTPATLVLTSDQSSPEI

51 DEDRIPNPHLKSTLAMCPRQRKKMTRITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 12:
  1 MEQDNSPQKIQFTVPLLEPHLDPEAAEQIRRRRPTPATLVLTSDQSSPEI

51 DEDRIPNPHLKSTLAMSPRQRKKMCRITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 15:
                                                      ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCCACCCCTG CCACCCTCGT GCTGACCAGT

301 GACCAGTCAT CCCCAGAGAT AGATGAAGAC CGGATCCCCA ACCCACATCT CAAGTCCACT

361 TTGGCAATGG CACCACGGCA ACGGAAGAAG ATGGCAAGGA TCACACCCAC AATGAAAGAG

421 CTCCAGATGA TGGTTGAACA TCACCTGGCG CAACAGCAGC ATGGACAGGA ACCTGAGGGG

481 GCCGCTGAGA GCACAGGAAC CCAGGAGTCC CGCCCACCTG GGATCCCAGA CACAGAAGTG

541 GAGTCAAGGC TGGGCACCTC TGGGACAGCA AAAAAAACTG CAGAATGCAT CCCTAAAACT

601 CACGAAAGAG GCAGTAAGGA ACCCAGCACA AAAGAACCCT CAACCCATAT ACCACCACTG

661 GATTCCAAGG GAGCCAACTC GGTCTGA

SEQ ID NO: 16:
  1 MEQDNSPQKIQFTVPLLEPHLDPEAAEQIRRRRPTPATLVLTSDQSSPEI

51 DEDRIPNPHLKSTLAMAPRQRKKMARITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 17:
                                                      ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCCACCCCTG CCACCCTCGT GCTGACCAGT

301 GACCAGTCAT CCCCAGAGAT AGATGAAGAC CGGATCCCCA ACCCACATCT CAAGTCCACT

361 TTGGCAATGG ACCCACGGCA ACGGAAGAAG ATGGACAGGA TCACACCCAC AATGAAAGAG

421 CTCCAGATGA TGGTTGAACA TCACCTGGGG CAACAGCAGC AACGAGAGGA ACCTGAGGGG

481 GCCGCTGAGA GCACAGGAAC CCAGGAGTCC CGCCCACCTG GGATCCCAGA CACAGAAGTG

541 GAGTCAAGGC TGGGCACCTC TGGGACAGCA AAAAAAACTG CAGAATGCAT CCCTAAAACT

601 CACGAAAGAG GCAGTAAGGA ACCCAGCACA AAAGAACCCT CAACCCATAT ACCACCACTG

661 GATTCCAACG GAGCCAACTC GGTCTGA

SEQ ID NO: 18:
  1 MEQDNSPQKIQFTVPLLEPHLDPEAAEQIRRRRPTPATLVLTSDQSSPEI

51 DEDRIPNPHLKSTLAMDPRQRKKMDRITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 19:
                                                      ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCCGACCCTG CCACCCTCGT GCTGACCAGT

301 GACCAGTCAT CCCCAGAGAT AGATGAAGAC CGGATCCCCA ACCCACATCT CAAGTCCACT

361 TTGGCA

SEQ ID NO: 20:
  1 MEQDNSPQKIQFTVPLLEPHLDPEAAEQTRRRRPDPATINLTSDQSSPEI

51 DEDRIPNPHLKSTLA

SEQ ID NO: 21:
  1 MEQDNSPQKIQFTVPLLEPHLDPEAAEQTRRRRPDPATLVLTSDQSSPEI

51 DEDRIPNPHLKSTLAMAPRQRKKMTRITPTMKELQMMVEHHLGQQQ

101 QGEEPEGAAESTGTQESRPPGIPDTEVESRLGTSGTAKKTAECIPKTHER

151 GSKEPSTKEPSTHIPPLDSKGANSV

SEQ ID NO: 22:

ATGGAGCAA

181 GACAACAGCC CCCAAAAGAT CCAGTTCACG GTCCCGCTGC TGGAGCCGCA CCTTGACCCC

241 GAGGCGGCGG AGCAGATTCG GAGGCGCCGC CCC<u>GAC</u>CCTG CCACCCTCGT GCTGACCAGT

301 GACCAGTCAT CCCCAGAGAT AGATGAAGAC CGGATCCCCA ACCCACATCT CAAGTCCACT

361 TTGGCAATG<u>G CA</u>CCACGGCA ACGGAAGAAG ATGACAAGGA TCACACCCAC AATGAAAGAG

421 CTCCAGATGA TGGTTGAACA TCACCTGGGG CAACAGCAGC AAGGAGAGGA ACCTGAGGGG

481 GCCGCTGAGA GCACAGGAAC CCAGGAGTCC CGCCCACCTG GGATCCCAGA CACAGAAGTG

541 GAGTCAAGGC TGGGCACCTC TGGGACAGCA AAAAAAACTG CAGAATGCAT CCCTAAAACT

601 CACGAAAGAG GCAGTAAGGA ACCCAGCACA AAGAACCCT CAACCCATAT ACCACCACTG

661 GATTCCAAGG GAGCCAACTC GGTCTGA

---

What is claimed is:

1. A method of decreasing cardiac contractility in a subject, the method comprising:

introducing, into heart cells of the subject, an effective amount of an isolated nucleic acid molecule that encodes a variant phosphatase inhibitor-1 protein, wherein the nucleic acid molecule encodes a polypeptide having at least 90% identity to:

(a) SEQ ID NO:6 or a fragment of SEQ ID NO: 6;
(b) SEQ ID NO: 21 or a fragment of SEQ ID NO: 21; or
(c) SEQ ID NO:16 or a fragment of SEQ 1D NO: 16, and wherein the polypeptide or the fragment comprises:

(i) a constitutively phosphorylated amino acid at position 35, said constitutively phosphorylated amino acid being aspartic acid or glutamic acid, and (ii) a constitutively unphosphorylated amino acid at positions 67 and/or 75, wherein, the polypeptide or fragment inhibits the activity of rabbit protein phosphatase I and wherein expression of the encoded polypeptide decreases cardiac contractility in the subject.

* * * * *

UNITED STATES PATENT AND TRADEMARK OFFICE
CERTIFICATE OF CORRECTION

| | |
|---|---|
| PATENT NO. | : 8,524,683 B2 |
| APPLICATION NO. | : 13/196450 |
| DATED | : September 3, 2013 |
| INVENTOR(S) | : Evangelia Kranias et al. |

Page 1 of 1

It is certified that error appears in the above-identified patent and that said Letters Patent is hereby corrected as shown below:

In the Specification

Line 43, add Grant No.(s) HL-57263, DK-36569, HL-07382, HL-57623 and HL-52378.

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,524,683 B2 | Page 1 of 1 |
| APPLICATION NO. | : 13/196450 | |
| DATED | : September 3, 2013 | |
| INVENTOR(S) | : Evangelia Kranias et al. | |

It is certified that error appears in the above-identified patent and that said Letters Patent is hereby corrected as shown below:

In the Specification

Column 1, Line 43, add Grant No.(s) HL-57263, DK-36569, HL-07382, HL-57623 and HL-52378.

This certificate supersedes the Certificate of Correction issued June 24, 2014.

Signed and Sealed this
Fifth Day of August, 2014

Michelle K. Lee
*Deputy Director of the United States Patent and Trademark Office*

SEQUENCE LISTING

<160> NUMBER OF SEQ ID NOS: 40

<210> SEQ ID NO 1
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggagcaag acaacagccc cgaaagatc cagttcacgg tcccgctgct ggagccgcac      60
cttgaccccg aggcggcgga gcagattcgg aggcgccgcc caccccctgc caccctcgtg   120
ctgaccagtg accagtcatc cccagagata gatgaagacc ggatccccaa cccacatctc   180
aagtccactt tggcaatggc accacggcaa cggaagaaga tgacaaggat cacacccaca   240
atgaaagagc tccagatgat ggttgaacat cacctgggc aacagcagca aggagaggaa    300
cctgaggggg ccgctgagag cacaggaacc caggagtccc gcccacctgg gatcccagac   360
acagaagtgg agtcaaggct gggcacctct gggacagcaa aaaaaactgc agaatgcatc   420
cctaaaactc acgagagagg cagtaaggaa cccagcacaa agaaccctc aacccatata    480 ccaccactgg attccaaggg agccaactcg gtctga                              516

<210> SEQ ID NO 2
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggagcaag acaacagccc cgaaagatc cagttcacgg tcccgctgct ggagccgcac      60
cttgaccccg aggcggcgga gcagattcgg aggcgccgcc caccccctgc caccctcgtg   120
ctgaccagtg accagtcatc cccagagata gatgaagacc ggatccccaa cccacatctc   180
aagtccactt tggcaatgga cccacggcaa cggaagaaga tgacaaggat cacacccaca   240

```
atgaaagagc tccagatgat ggttgaacat cacctggggc aacagcagca aggagaggaa    300 cctgagggg  ccgctgagag cacaggaacc caggagtccc gcccacctgg gatcccagac    360
acagaagtgg agtcaaggct gggcacctct gggacagcaa aaaaaactgc agaatgcatc    420
cctaaaactc acgagagagg cagtaaggaa cccagcacaa agaaccctc aacccatata    480 ccaccactgg attccaaggg agccaactcg gtctga                              516
```

```
<210> SEQ ID NO 3
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
atggagcaag acaacagccc ccgaaagatc cagttcacgg tcccgctgct ggagccgcac    60
cttgaccccg aggcggcgga gcagattcgg aggcgccgcc ccaccctgc caccctcgtg   120 ctgaccagtg accagtcatc cccagagata gatgaagacc ggatccccaa cccacatctc   180
aagtccactt tggcaatgtc tccacggcaa cggaagaaga tggacaggat cacacccaca   240
atgaaagagc tccagatgat ggttgaacat cacctggggc aacagcagca aggagaggaa   300 cctgagggg  ccgctgagag cacaggaacc caggagtccc gcccacctgg gatcccagac   360
acagaagtgg agtcaaggct gggcacctct gggacagcaa aaaaaactgc agaatgcatc   420
cctaaaactc acgagagagg cagtaaggaa cccagcacaa agaaccctc aacccatata   480 ccaccactgg attccaaggg agccaactcg gtctga                             516
```

```
<210> SEQ ID NO 4
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
```

```
atggagcaag acaacagccc ccgaaagatc cagttcacgg tcccgctgct ggagccgcac    60
cttgaccccg aggcggcgga gcagattcgg aggcgccgcc ccaccctgc caccctcgtg   120 ctgaccagtg accagtcatc cccagagata gatgaagacc ggatccccaa cccacatctc   180
aagtccactt tggcaatgtc tccacggcaa cggaagaaga tggcaaggat cacacccaca   240
atgaaagagc tccagatgat ggttgaacat cacctggggc aacagcagca aggagaggaa   300 cctgagggg  ccgctgagag cacaggaacc caggagtccc gcccacctgg gatcccagac   360
acagaagtgg agtcaaggct gggcacctct gggacagcaa aaaaaactgc agaatgcatc   420
cctaaaactc acgagagagg cagtaaggaa cccagcacaa agaaccctc aacccatata   480 ccaccactgg attccaaggg agccaactcg gtctga                             516
```

```
<210> SEQ ID NO 5
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Ser Pro Arg Gln Arg Lys Lys Met Asp Arg Ile Thr Pro Thr
65                  70                  75                  80

Met Lys Glu Leu Gln Met Met Val Glu His His Leu Gly Gln Gln Gln
            85                  90                  95

Gln Gly Glu Glu Pro Glu Gly Ala Ala Glu Ser Thr Gly Thr Gln Glu
        100                 105                 110

Ser Arg Pro Pro Gly Ile Pro Asp Thr Glu Val Glu Ser Arg Leu Gly
    115                 120                 125

Thr Ser Gly Thr Ala Lys Lys Thr Ala Glu Cys Ile Pro Lys Thr His
130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 6
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Ser Pro Arg Gln Arg Lys Lys Met Ala Arg Ile Thr Pro Thr
65                  70                  75                  80

Met Lys Glu Leu Gln Met Met Val Glu His His Leu Gly Gln Gln Gln
            85                  90                  95

Gln Gly Glu Glu Pro Glu Gly Ala Ala Glu Ser Thr Gly Thr Gln Glu
        100                 105                 110

Ser Arg Pro Pro Gly Ile Pro Asp Thr Glu Val Glu Ser Arg Leu Gly
    115                 120                 125

Thr Ser Gly Thr Ala Lys Lys Thr Ala Glu Cys Ile Pro Lys Thr His
130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 7
<211> LENGTH: 720
```

<212> TYPE: DNA
<213> ORGANISM: Homo sapiens

<400> SEQUENCE: 7

```
agagtccccg gagccgcgag ctgggagcgc tgtgccggga gccgggagcc gagcgcgccg    60
ggctggggcc ggggccggag cggagcggag agggagcgcg cccgccccag ccccgagtcc   120
cgccgccttc cctcccgccg cagcgcgggc ccaccggccg ccgccccagc catggagcaa   180
gacaacagcc cccgaaagat ccagttcacg gtcccgctgc tggagccgca ccttgacccc   240
gaggcggcgg agcagattcg gaggcgccgc cccaccctg ccaccctcgt gctgaccagt   300
gaccagtcat ccccagagat agatgaagac cggatcccca cccacatct caagtccact   360
ttggcaatgt ctccacggca acggaagaag atgacaagga tcacacccac aatgaaagag   420
ctccagatga tggttgaaca tcacctgggg caacagcagc aaggagagga acctgagggg   480
gccgctgaga gcacaggaac ccaggagtcc cgcccacctg ggatcccaga cacagaagtg   540
gagtcaaggc tgggcacctc tgggacagca aaaaaaactg cagaatgcat ccctaaaact   600
cacgagagag gcagtaagga acccagcaca aagaacccct caacccatat accaccactg   660
gattccaagg gagccaactc ggtctgagag aggaggaggt atcttgggat caagactgca   720
```

<210> SEQ ID NO 8
<211> LENGTH: 171
<212> TYPE: PRT
<213> ORGANISM: Homo sapiens

<400> SEQUENCE: 8

```
Met Glu Gln Asp Asn Ser Pro Arg Lys Ile Gln Phe Thr Val Pro Leu
 1               5                  10                  15

Leu Glu Pro His Leu Asp Pro Glu Ala Ala Glu Gln Ile Arg Arg Arg
                20                  25                  30

Arg Pro Thr Pro Ala Thr Leu Val Leu Thr Ser Asp Gln Ser Ser Pro
            35                  40                  45

Glu Ile Asp Glu Asp Arg Ile Pro Asn Pro His Leu Lys Ser Thr Leu
        50                  55                  60

Ala Met Ser Pro Arg Gln Arg Lys Lys Met Thr Arg Ile Thr Pro Thr
65                  70                  75                  80

Met Lys Glu Leu Gln Met Met Val Glu His His Leu Gly Gln Gln Gln
                85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170
```

<210> SEQ ID NO 9
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atggagcaag acaacagccc ccgaaagatc cagttcacgg tcccgctgct ggagccgcac    60
cttgaccccg aggcggcgga gcagattcgg aggcgccgcc ccaccccTGc caccctcgtg   120
ctgaccagtg accagtcatc cccagagata gatgaagacc ggatccccaa cccacatctc   180
aagtccactt tggcaatgtg yccacggcaa cggaagaaga tgacaaggat cacacccaca   240
atgaaagagc tccagatgat ggttgaacat caccTGgggc aacagcagca aggagaggaa   300 cctgagggggg ccgctgagag cacaggaacc caggagtccc gcccacctgg atcccagac   360 acagaagtgg agtcaaggct gggcacctct gggacagcaa aaaaaactgc agaatgcatc   420
cctaaaactc acgagagagg cagtaaggaa cccagcacaa agaaccctc aacccatata   480 ccaccactgg attccaaggg agccaactcg gtctga                             516
```

<210> SEQ ID NO 10
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggagcaag acaacagccc ccgaaagatc cagttcacgg tcccgctgct ggagccgcac    60
cttgaccccg aggcggcgga gcagattcgg aggcgccgcc ccaccccTGc caccctcgtg   120
ctgaccagtg accagtcatc cccagagata gatgaagacc ggatccccaa cccacatctc   180
aagtccactt tggcaatgtc tccacggcaa cggaagaaga tgtgyaggat cacacccaca   240
atgaaagagc tccagatgat ggttgaacat caccTGgggc aacagcagca aggagaggaa   300 cctgagggggg ccgctgagag cacaggaacc caggagtccc gcccacctgg atcccagac   360 acagaagtgg agtcaaggct gggcacctct gggacagcaa aaaaaactgc agaatgcatc   420
cctaaaactc acgagagagg cagtaaggaa cccagcacaa agaaccctc aacccatata   480 ccaccactgg attccaaggg agccaactcg gtctga                             516
```

<210> SEQ ID NO 11
<211> LENGTH: 171
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Cys Pro Arg Gln Arg Lys Lys Met Thr Arg Ile Thr Pro Thr
65                  70                  75                  80

Met Lys Glu Leu Gln Met Met Val Glu His His Leu Gly Gln Gln Gln
                85                  90                  95

Gln Gly Glu Glu Pro Glu Gly Ala Ala Glu Ser Thr Gly Thr Gln Glu
            100                 105                 110
```

```
Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 12
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Lys Ser Thr Leu
    50                  55                  60

Ala Met Ser Pro Arg Gln Arg Lys Lys Met Cys Arg Ile Thr Pro Thr
65                  70                  75                  80

Met Lys Glu Leu Gln Met Met Val Glu His His Leu Gly Gln Gln
                85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 13
<211> LENGTH: 243
<212> TYPE: DNA
<213> ORGANISM: Homo sapiens

<400> SEQUENCE: 13
gggcgaattg ggtaccgcca ccatggaaca ggacaacagc ccccggaaga tccagttcac      60
cgtgcccctg ctggaacccc acctggaccc cgaggccgcc gagcagatcc ggcggagaag     120
gcccgacccc gccaccctgg tgctgaccag cgaccagagc agccccgaga tcgacgagga     180
ccggatcccc aaccccacc tgaagagcac cctggcctga tgagagctcc agcttttgtt     240
ccc                                                                   243

<210> SEQ ID NO 14
<211> LENGTH: 65
<212> TYPE: PRT
<213> ORGANISM: Homo sapiens
```

<400> SEQUENCE: 14

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Asp Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala
65

<210> SEQ ID NO 15
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggagcaag acaacagccc ccgaaagatc cagttcacgg tcccgctgct ggagccgcac     60
cttgaccccg aggcggcgga gcagattcgg aggcgccgcc ccaccccntgc cacccntcgtg    120 ctgaccagtg accagtcatc cccagagata gatgaagacc ggatcccaa cccacatctc    180 aagtccactt tggcaatggc accacggcaa cggaagaaga tgcaaggat cacacccaca    240 atgaaagagc tccagatgat ggttgaacat cacctggggc aacagcagca aggagaggaa    300 cctgagggg ccgctgagag cacaggaacc caggagtccc gcccacctgg gatcccagac     360
acagaagtgg agtcaaggct gggcacctct gggacagcaa aaaaaactgc agaatgcatc    420
cctaaaactc acgagagagg cagtaaggaa cccagcacaa agaaccctc aacccatata    480 ccaccactgg attccaaggg agccaactcg gtctga                              516

<210> SEQ ID NO 16
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Ala Pro Arg Gln Arg Lys Lys Met Ala Arg Ile Thr Pro Thr
65                  70                  75                  80

Met Lys Glu Leu Gln Met Met Val Glu His His Leu Gly Gln Gln Gln
                85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

```
Thr Ser Gly Thr Ala Lys Lys Thr Ala Glu Cys Ile Pro Lys Thr His
        130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 17
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggagcaag acaacagccc ccgaaagatc cagttcacgg tcccgctgct ggagccgcac      60
cttgaccccg aggcggcgga gcagattcgg aggcgccgcc ccaccccctgc caccctcgtg    120 ctgaccagtg accagtcatc cccagagata gatgaagacc ggatccccaa cccacatctc    180
aagtccactt tggcaatgga cccacggcaa cggaagaaga tggacaggat cacacccaca    240
atgaaagagc tccagatgat ggttgaacat cacctggggc aacagcagca aggagaggaa    300 cctgagggg ccgctgagag cacaggaacc caggagtccc gcccacctgg atcccagac      360 acagaagtgg agtcaaggct gggcacctct gggacagcaa aaaaactgc agaatgcatc     420 cctaaaactc acgagagagg cagtaaggaa cccagcacaa agaaccctc aacccatata     480 ccaccactgg attccaaggg agccaactcg gtctga                              516

<210> SEQ ID NO 18
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Asp Pro Arg Gln Arg Lys Lys Met Asp Arg Ile Thr Pro Thr
65                  70                  75                  80

Met Lys Glu Leu Gln Met Met Val Glu His His Leu Gly Gln Gln Gln
                85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160
```

```
Pro Pro Leu Asp Ser Lys Gly Ala Asn Ser Val
            165                 170
```

<210> SEQ ID NO 19
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggagcaag acaacagccc ccgaaagatc cagttcacgg tcccgctgct ggagccgcac      60
cttgaccccg aggcggcgga gcagattcgg aggcgccgcc ccaccctgc caccctcgtg      120 ctgaccagtg accagtcatc cccagagata gatgaagacc ggatcccaa cccacatctc      180 aagtccactt tggca                                                       195
```

<210> SEQ ID NO 20
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Asp Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala
65
```

<210> SEQ ID NO 21
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Asp Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Ala Pro Arg Gln Arg Lys Lys Met Thr Arg Ile Thr Pro Thr
65                  70                  75                  80

Met Lys Glu Leu Gln Met Met Val Glu His Leu Gly Gln Gln Gln
            85                  90                  95

Gln Gly Glu Glu Pro Gly Gly Ala Ala Glu Ser Thr Gly Thr Gln Glu
        100                 105                 110
```

```
Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

<210> SEQ ID NO 22
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggagcaag acaacagccc ccgaaagatc cagttcacgg tcccgctgct ggagccgcac        60
cttgaccccg aggcggcgga gcagattcgg aggcgccgcc ccgaccctgc caccctcgtg       120
ctgaccagtg accagtcatc cccagagata gatgaagacc ggatcccccaa cccacatctc      180 aagtccactt tggcaatggc accacggcaa cggaagaaga tgacaaggat cacacccaca       240
atgaaagagc tccagatgat ggttgaacat cacctggggc aacagcagca aggagaggaa       300
cctgaggggg ccgctgagag cacaggaacc caggagtccc gcccacctgg gatcccagac       360
acagaagtgg agtcaaggct gggcacctct gggacagcaa aaaaaactgc agaatgcatc       420
cctaaaactc acgagagagg cagtaaggaa cccagcacaa agaaccctc aacccatata        480 ccaccactgg attccaaggg agccaactcg gtctga                                  516

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Lys Met Thr Arg Ile Thr Pro Thr Met Lys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Glu Pro Asp Asn Ser Pro Arg Lys Ile Gln Phe Thr Val Pro
1               5                   10                  15

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

-continued cagagaattc catggagcaa gacaacagcc c  31

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagagcggcc gctcagaccg agttggctcc ct  32

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccactttgg caatggcacc acggcaacgg aagaa  35

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cggcaaaaga agatggcaag gatcacaccc ac  32

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tccactttgg caatggaccc acggcaacgg aagaa  35

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cggcaacgga agaaatggac aggatcacac ccac  34

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Thr Leu Ala Met Ser Pro Arg Gln Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Thr Ala Glu Cys Ile Pro Lys Thr His Glu Arg
1               5                   10

<210> SEQ ID NO 33
<211> LENGTH: 10
<212> TYPE: PRT
<213> ORGANISM: Homo sapiens

<400> SEQUENCE: 33

Lys Met Thr Arg Ile Thr Pro Thr Met Lys
1               5                   10

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcaatgtctc cacggcaacg gaagaagatg acaaggatc                          39

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcaatggcac cacggcaacg gaagaagatg acaaggatc                          39

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcaatgtctc cacggcaacg gaagaagatg gcaaggatc                          39

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcaatggcac cacggcaacg gaagaagatg gcaaggatc                          39

<210> SEQ ID NO 38

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcaatgtctc cacggcaacg gaagaagatg gacaggatc                              39

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaatggacc cacggcaacg gaagaagatg acaaggatc                              39

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcaatggacc cacggcaacg gaagaagatg gacaggatc                              39
```